US008110389B2

(12) United States Patent
Lavigne et al.

(10) Patent No.: US 8,110,389 B2
(45) Date of Patent: Feb. 7, 2012

(54) FAMILY 6 CELLULASE WITH DECREASED INACTIVATION BY LIGNIN

(75) Inventors: James A. Lavigne, Ontario (CA); Brian R. Scott, Ontario (CA); Martine Whissel, Ontario (CA); John J. Tomashek, Ontario (CA)

(73) Assignee: Iogen Energy Corporation, Ontario (CA)

( * ) Notice: Subject to any disclaimer, the term of this patent is extended or adjusted under 35 U.S.C. 154(b) by 103 days.

(21) Appl. No.: 12/512,403

(22) Filed: Jul. 30, 2009

(65) Prior Publication Data

US 2010/0041100 A1    Feb. 18, 2010

Related U.S. Application Data

(60) Provisional application No. 61/085,559, filed on Aug. 1, 2008.

(51) Int. Cl.
| | |
|---|---|
| *C12N 9/42* | (2006.01) |
| *C12N 9/14* | (2006.01) |
| *C12N 15/00* | (2006.01) |
| *C12N 1/20* | (2006.01) |
| *C12N 1/00* | (2006.01) |
| *C12P 9/04* | (2006.01) |
| *C12P 21/06* | (2006.01) |
| *C12P 19/34* | (2006.01) |
| *C02F 3/34* | (2006.01) |
| *D21C 1/00* | (2006.01) |
| *C07H 21/04* | (2006.01) |

(52) U.S. Cl. ....... 435/209; 435/195; 435/101; 435/69.1; 435/91.1; 435/320.1; 435/252.3; 435/254.11; 435/254.2; 435/254.3; 435/254.6; 435/254.7; 435/262; 435/277; 536/23.2; 536/23.74; 536/23.1

(58) Field of Classification Search .................. 435/209, 435/195, 101, 69.1, 91.1, 320.1, 252.3, 254.11, 435/254.2, 254.3, 254.6, 254.7, 262, 277; 536/23.2, 23.74, 23.1
See application file for complete search history.

(56) References Cited

U.S. PATENT DOCUMENTS

| | | | |
|---|---|---|---|
| 4,409,032 | A | 10/1983 | Paszner et al. |
| 4,461,648 | A | 7/1984 | Foody |
| 5,677,151 | A | 10/1997 | Wilson et al. |
| 6,114,158 | A | 9/2000 | Li et al. |
| 6,114,296 | A | 9/2000 | Schulein et al. |
| 7,348,168 | B2 | 3/2008 | Wu et al. |
| 7,354,743 | B2 | 4/2008 | Vlasenko et al. |
| 7,375,197 | B2 | 5/2008 | Adney et al. |
| 7,785,854 | B2 * | 8/2010 | St-Pierre et al. ............. 435/200 |
| 2004/0185542 | A1 | 9/2004 | Yang et al. |
| 2006/0088922 | A1 | 4/2006 | Yang et al. |
| 2006/0205042 | A1 | 9/2006 | Aehle et al. |
| 2007/0173431 | A1 | 7/2007 | Day et al. |
| 2008/0167214 | A1 | 7/2008 | Teter et al. |
| 2009/0186381 | A1 | 7/2009 | Lavigne et al. |
| 2010/0041104 | A1 | 2/2010 | Cascao-Pereira et al. |

FOREIGN PATENT DOCUMENTS

| | | |
|---|---|---|
| WO | 94/07998 | 4/1994 |
| WO | 99/01544 | 1/1999 |
| WO | 2005/024037 | 3/2005 |
| WO | 2005/028636 | 3/2005 |
| WO | 2006/074005 | 7/2006 |
| WO | 2008/025164 | 3/2008 |
| WO | 2008/095033 | 8/2008 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.* Sen et al., Developments in directed evolution for improving enzyme functions. Appl. Biochem. Biotechnol., 2007, vol. 143: 212-223.*
Berlin, et al., "Inhibition of cellulase, xylanase and β-glucosidase activities by softwood lignin preparations", J. Biotech., vol. 125, No. 2 (2005) 198-209.
Berlin, et al., "Weak Lignin-Binding Enzymes", Appl. Biochem. and Biotech., vol. 121-124 (2005) 163-70.
Birren, et al., "Exoglucanase 2 prescursor [*Aspergillus terreus* NIH2624]", NCBIIXP_001210279 (2008).
Birren, et al., Hypothetical protein CC1G_01107 [*Coprinopsis cinerea* okayamam 7#130], NCBI XP_001833045 (2008).

(Continued)

*Primary Examiner* — Ganapathirama Raghu
(74) *Attorney, Agent, or Firm* — Fitzpatrick, Cella, Harper & Scinto

(57) ABSTRACT

A modified *Trichoderma reesei* Family 6 (TrCel6A) cellulase enzyme comprising amino acid substitutions at one or more positions selected from the group consisting of 129, 322, 363 and 410 of SEQ ID NO: 1 is provided. Genetic constructs and genetically modified microbes comprising nucleic sequences encoding the modified TrCel6a cellulase are also provided. The modified TrCel6A cellulase of the invention display at least a 15% decrease in inactivation by lignin relative to a parental TrCel6A cellulase from which the modified TrCel6A is derived. Such cellulases find use in a variety of applications in industry requiring enzymatic hydrolysis of cellulose in the presence of lignin, e.g., the hydrolysis of pretreated lignocellulosic feedstocks for the production of fermentable sugars, sugar alcohols and fuel alcohols.

15 Claims, 21 Drawing Sheets

OTHER PUBLICATIONS

Chernoglazov, et al., "Adsorption of high-purity endo-1,4-β-glucanases from *Trichoderma reesei* on components of lignocellulosic materials: cellulose, lignin, and xylan", Enzyme Microb. Technol., vol. 10, No. 8 (1988) 503-7.

Davies, et al., "Structure and function of Humicola insolens family 6 cellulases: structure of the endoglucanase, Cel6B, at 1.6 Å resolution", Biochem. J., vol. 348 (2000) 201-7.

Excoffier, et al., "Saccharification of Steam-Exploded Poplar Wood", Biotech. and Bioeng., vol. 38, No. 11 (1991) 1308-17.

Kaya, et al., "Influence of lignin and its degradation products on enzymatic hydrolysis of xylan", J. Biotech., vol. 80, No. 3 (2000) 241-47.

Kong, et al., "Effects of Cell-Wall Acetate, Xylan Backbone, and Lignin on Enzyme Hydrolysis of Aspen Wood", App. Biochem. and Biotech., vol. 34-35 (1992) 23-5.

Meunier-Goddik, et al., "Enzyme-Catalyzed Saccharification of Model Celluloses in the Presence of Lignacious Residues", J. Agr. Food Chem., vol. 47, No. 1 (1999) 346-51.

Mooney, et al., "The Effect of Initial Pore Volume and Lignin Content on the Enzymatic Hydrolysis of Softwoods", Bioresource Techn., vol. 64 (1998) 113-19.

Palonen, et al., "Adsorption of *Trichoderma reesei* CBH I and EG II and their catalytic domains on steam pretreated softwood and isolated lignin", J. Biotechn., vol. 107 (2004) 65-72.

Rouvinen, et al., "Three-Dimensional Structure of Cellobiohydrolase II from *Trichoderma reesei*" Science, vol. 249, No. 4967 (1990) 380-86.

Spezio, et al., "Crystal Structure of the Catalytic Domain of a Thermophilic Endocellulase" Biochem., vol. 32, No. 38 (1993) 9906-16.

Tu, et al., "Evaluating the Distribution of Cellulases and the Recycling of Free Cellulases during the Hydrolysis of Lignocellulosic Substrates", Biotech. Prog., vol. 23, No. 2 (2007) 398-406.

Varrot, et al., "Mycobacterium tuberculosis Strains Possess Functional Cellulases", J. Biolog. Chem., vol. 280, No. 21 (2005) 20181-84.

Varrot, et al., "Structural Changes of the Active Site Tunnel of Humicola insolens Cellobiohydrolase, Cel6A, upon Oligosaccharide Binding", Biochem., vol. 38, No. 28 (1999) 8884-91.

Yang, et al., "BSA Treatment to Enhance Enzymatic Hydrolysis of Cellulose in Lignin Containing Substrates", Biotechn. and Bioeng., vol. 94, No. 4 (2006) 611-17.

Carrard, et al., "Widely different off rates of two closely related cellulose-binding domains from *Trichoderma reesei*", Eur. J. Biochem., vol. 262, No. 3 (1999) 637-43.

Chica, et al., "Semi-rational approaches to engineering enzyme activity: combining the benefits of directed evolution and rational design", Curr. Opin. Biotech., vol. 16, No. 41 (2005) 378-84.

Eijsink, et al., "Directed evolution of enzyme stability", Biomolecular Engineering, vol. 22, No. 1-3 (2005) 21-30.

Fägerstam, et al., "The primary structure of a 1,4-β-glucan cellobiohydrolase from the fungus *Trichoderma reesei* QM 9414", FEBS Letters, vol. 167, No. 2 (1984) 309-15.

Gilkes, et al., "Domains in Microbial β-1,4-Glycanases: Sequence Conservation, Function, and Enzyme Families", Microbiological Reviews, vol. 55, No. 2 (1991) 303-15.

Gilkes, et al., "The Adsorption of a Bacterial Cellulase and Its Two Isolated Domains to Crystalline Cellulose", Journal of Biological Chemistry, vol. 267, No. 10 (1992) 6743-49.

Goto, "Protein O-Glycosylation in Fungi: Diverse Structures and Multiple Functions", Biosci. Biotechnol. Biochem., vol. 71, No. 6 (2007) 1415-27.

Holtzapple, et al., "The Ammonia Freeze Explosion (AFEX) Process: A Practical Lignocellulosic Pretreatment", Applied Biochemistry and Biotechnology, vol. 28/29 (1991) 59-74.

Kraulis, et al., "Determination of the Three-Dimensional Solution Structure of the C-Terminal Domain of Cellobiohydrolase I from *Trichoderma reesei*. A Study Using Nuclear Magnetic Resonance and Hybrid Distance Geometry-Dynamical Simulated Annealing", Biochemistry, vol. 28 (1989) 7241-57.

Linder, et al., "Identification of functionally important amino acids in the cellulose-binding domain of *Trichoderma reesei* cellobiohydrolase I", Protein Science, vol. 4, No. 6 (1995) 1056-64.

Mattinen, et al., "Interaction between cellohexaose and cellulose binding domains from *Trichoderma reesei* cellulases", FEBS Letters, vol. 407, No. 3 (1997) 291-96.

Reinikainen, et al., "Investigation of the Function of Mutated Cellulose-Binding Domains of *Trichoderma reesei* Cellobiohydrolase I", Proteins, vol. 14, No. 4 (1992) 475-82.

Srisodsuk, et al., "Role of the Interdomain Linker Peptide of *Trichoderma reesei* Cellobiohydrolase I in Its Interaction ith Crystalline Cellulose", Journal of Biological Chemistry, vol. 268, No. 28 (1993) 20756-61.

Srisodsuk, et al., "*Trichoderma reesei* cellobiohydrolase I with an endoglucanase cellulose-binding domain: action on bacterial microcrystalline cellulose", Journal of Biotechnology, vol. 57, No. 1-3 (1997) 49-57.

Tomme, et al., "Studies of the cellulolytic system of *Trichoderma reesei* QM 9414. Analysis of domain function in two cellobiohydrolases by limited proteolysis", Eur. J. Biochem., vol. 170, No. 3 (1988) 575-81.

Viikari, et al., "Thermostable Enzymes in Lignocellulose Hydrolysis", Adv. Biochem. Engin./Biotechnol., vol. 108 (2007) 121-45.

Weil, et al., "Preteatment of Yellow Poplar Sawdust by Pressure Cooking in Water", Applied Biochemistry and Biotechnology, vol. 68, No. 1-2 (1997) 21-40.

* cited by examiner

```
SEQ ID NO: 1      83  SGTATYSGNPFVG--------VTPWANAYYASEVSSLAIP  114
CONSENSUS             ---ATASGNPFVG--------VQLWANPYYASEVASLAIP
SEQ ID NO: 2          ---ATYSGNPFVG--------VTPWANAYYASEVSSLAIP
SEQ ID NO: 3          ---ATYSGNPFVG--------VTPWANAYYASEVSSLAIP
SEQ ID NO: 4          ---ATYSGNPFVG--------VTPWANAYYASEVSSLAIP
SEQ ID NO: 5          ---ATYSGNPFVG--------VTPWANAYYASEVSSLAIP
SEQ ID NO: 6          ---ATYSGNPFVG--------VTPWANAYYASEVSSLAIP
SEQ ID NO: 7          ---ATASGNPFSG--------YQLYVNPYYSSEVQSIAIP
SEQ ID NO: 8          ---ASASGNPFSG--------YQLYVNPYYSSEVASLAIP
SEQ ID NO: 9          ---ATAGGNPFEG--------YDLYVNPYYKSEVESLAIP
SEQ ID NO: 10         ---ASATGNPFEG--------YQLYANPYYKSQVESSAIP
SEQ ID NO: 11         ---AAASGNPFSG--------YQLYANPYYSSEVHTLAIP
SEQ ID NO: 12         ---ASASGNPFEG--------YQLYANPYYASEVISLAIP
SEQ ID NO: 13         ---PVATNNPFSG--------VDLWANNYYRSEVSTLAIP
SEQ ID NO: 14         ---PAASDNPYAG--------VDLWANNYYRSEVMNLAVP
SEQ ID NO: 15         ---ASFTGNPFLG--------VQGWANSYYSSEIYNHAIP
SEQ ID NO: 16         ---VQATGNPFEG--------YQLYANPYYSSEVMTLAVP
SEQ ID NO: 17         ---ASATGNPFEG--------YQLYVNPYYKSQVESSAIP
SEQ ID NO: 18         ---ASFTGNPFAG--------VNLFPNKFYSSEVHTLAIP
SEQ ID NO: 19         ---ASYNGNPFSG--------VQLWANTYYSSEVHTLAIP
SEQ ID NO: 20         ---ASYNGNPFSG--------VQLWANTYYSSEVHTLAIP
SEQ ID NO: 21         ---ATYTGNPFLG--------VNQWANNFYRSEIMNIAVP
SEQ ID NO: 22         ---ASYNGNPFEG--------VQLWANNYYRSEVHTLAIP
SEQ ID NO: 23         -------GNPFEG--------VQLWANNYYRSEVHTLAIP
SEQ ID NO: 24         ---AAPSGNPFAG--------KNFYANPYYSSEVHTLAMP
SEQ ID NO: 25         ------AGNPYTG--------KTVWLSPFYADEVAQAAAD
SEQ ID NO: 26         ---TPAAGNPFVG--------VTPFLSPYYAAEVAAAADA
SEQ ID NO: 27         ---TPAAGNPFTG--------YEIYLSPYYANEIAAAVTQ
SEQ ID NO: 28         ---TPAAGNPFT---------EQIYLSPYYANEIAAAVTQ
SEQ ID NO: 29         ---QANSSNPFAG--------HTIYPNPYYSNEIDEFAIP
SEQ ID NO: 30         ---PPSANNPWTG--------FQIFLSPYYANEVAAAAKQ
SEQ ID NO: 31         ---VPAAGNPYTG--------YEIYLSPYYAAEAQAAAAQ
SEQ ID NO: 32         ---LDASTNVFQQ--------YTLHPNNFYRAEVEAAAEA
SEQ ID NO: 33         ---TPDAGNPYIGYDVSHVLWCQIYLSPYYADEVAAAVSA
SEQ ID NO: 34         ---TPAAGNPFTG--------FQVYLSPYYSAEIASAAAA
SEQ ID NO: 35         ---LDASTNVWKK--------YTLHANKFYRTEVEAAVAA
SEQ ID NO: 36         ---LDASTNVFSK--------YTLHPNSFYRAEVEAAAEA
```

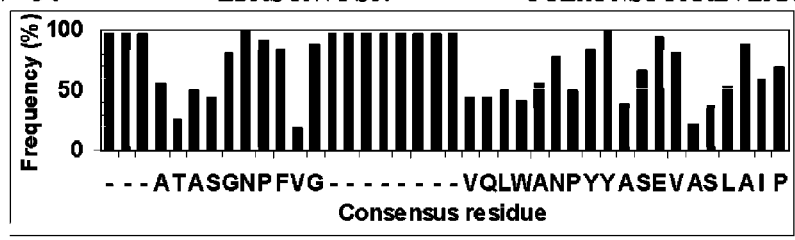

Figure 1

```
SEQ ID NO: 1      115  SLTG---AMATAAÅAVAKVPSFMWLDTLDKTP-LMEQTLA  150
CONSENSUS              SLTG---ALAAAAAAVAKVPSFQWLDTVAKVP-LMGTYLA
SEQ ID NO: 2           SLTG---AMATAAAAVAKVPSFMWLDTLDKTP-LMEQTLA
SEQ ID NO: 3           SLTG---AMATAAAAVAKVPSFMWLDTLDKTP-LMEQTLA
SEQ ID NO: 4           SLTG---AMATAAAAVAKVPSFMWLDTFDKTP-LMEQTLA
SEQ ID NO: 5           SLTG---AMATAAAAVAKVPSSMWLDTFDKTP-LMEQTLA
SEQ ID NO: 6           SLTG---AMATAAAAVAKVPSFMWLDTLDKTP-LMEQTLA
SEQ ID NO: 7           SLTGTLSSLAPAATAAAKVPSFVWLDVAAKVP-TMATYLA
SEQ ID NO: 8           SLTGSLSSLQAAATAAAKVPSFVWLDTAAKVP-TMGDYLA
SEQ ID NO: 9           SMTG---SLAEKASAAANVPSFHWLDTTDKVP-QMGEFLE
SEQ ID NO: 10          SLSAS--SLVAQASAAADVPSFYWLDTADKVP-TMGEYLE
SEQ ID NO: 11          SLTG---SLAAAATKAAEIPSFVWLDTAAKVP-TMGTYLA
SEQ ID NO: 12          SLSS---ELVPKASEVAKVPSFVWLDQAAKVP-SMGDYLK
SEQ ID NO: 13          KLS---GAMATAAAKVADVPSFQWMDT-YDHISFMEDSLA
SEQ ID NO: 14          KLS---GAKATAAAKVADVPSFQWMDT-YDHISLMEDTLA
SEQ ID NO: 15          SMT---GSLAAQASAVAKVPTFQWLDRNVTVDTLMKSTLE
SEQ ID NO: 16          SMTG---SLAEQATHAAEIPSFHWLDTTAKVP-TMGEYLA
SEQ ID NO: 17          SLSAS--SLVAQASAAADVPSFYWLDTADKVP-TMGEYLD
SEQ ID NO: 18          SLTG---SLVAKASAVAQVPSFQWLDIAAKVETLMPGALA
SEQ ID NO: 19          SLS---PELAAKAAKVAEVPSFQWLDRNVTVDTLFSGTLA
SEQ ID NO: 20          SLS---PELAAKAAKVAEVPSFQWLDRNVTVDTLFSGTLA
SEQ ID NO: 21          SLS---GAMATAAAKVADVPTFQWIDK-MDKLPLIDEALA
SEQ ID NO: 22          QITD--PALRAAASAVAEVPSFQWLDRNVTVDTLLVETLS
SEQ ID NO: 23          QITD--PALRAAASAVAEVPSFQWLDRNVTVDTLLVQTLS
SEQ ID NO: 24          SLPA---SLKPAATAVAKVGSFVWMDTMAKVP-LMDTYLA
SEQ ID NO: 25          ISNP---SLATKAASVAKIPTFVWFDTVAKVP-DLGGYLA
SEQ ID NO: 26          ITDS---TLKAKAASVAKIPTFTWLDSVAKVP-DLGTYLA
SEQ ID NO: 27          ISDP---TTAAAAAKVANIPTFIWLDQVAKVP-DLGTYLA
SEQ ID NO: 28          ISDP---TTAAAAAKVANIPTFIWLDQVAKVP-DLGTYLA
SEQ ID NO: 29          ALQETDPALVEKAALVKEVGTFFWIDVVAKVP-DIGPYLQ
SEQ ID NO: 30          ITDP---TLSSKAASVANIPTFTWLDSVAKIP-DLGTYLA
SEQ ID NO: 31          ISDA---TQKAKALKVAQIPTFTWFDVIAKTS-TLGDYLA
SEQ ID NO: 32          ISDS---ALAEKARKVADVGTFLWLDTIENIG-RLEPALE
SEQ ID NO: 33          ISNP---ALAAKAASVANIPTFIWFDVVAKVP-TLGTYLA
SEQ ID NO: 34          VTDS---SLKAKAASVANIPTFTWLDSVAKVP-DLGTYLA
SEQ ID NO: 35          ISDS---SLAAKAAKVANVGSFLWLDSIENIG-KLEPALE
SEQ ID NO: 36          ISDS---TLKAQALKVADVGSFLWIDTISAIS-RIEPGVS
```

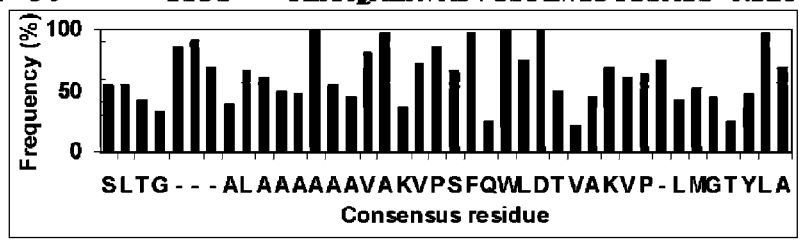

Figure 1 (Cont'd)

```
SEQ ID NO: 1    151 DIRTANKNGGN--YAGQFVVYDLPDRDCAALASNGEYSIA 188
CONSENSUS           DIRAANKAGGNP-YAGQFVVYDLPDRDCAALASNGEFSIA
SEQ ID NO: 2        DIRTANKNGGN--YAGQFVVYDLPDRDCAALASNGEYSIA
SEQ ID NO: 3        DIRTANKNGGN--YAGQFVVYDLPDRDCAALASNGEYSIA
SEQ ID NO: 4        DIRTANKNGGN--YAGQFVVYDLPDRDCAALASNGEYSIA
SEQ ID NO: 5        DIRTANKNGGN--YAGQFVVYDLPDRDCAALASNGEYSIA
SEQ ID NO: 6        DIRTANKNGGN--YAGQFVVYDLPDRDCAALASNGEYSIA
SEQ ID NO: 7        DIRSQNAAGANPPIAGQFVVYDLPDRDCAALASNGEFAIS
SEQ ID NO: 8        DIQSQNAAGANPPIAGQFVVYDLPDRDCAALASNGEYSIA
SEQ ID NO: 9        DIKTKNAAGANPPTAGIFVVYDLPDRDCAALASNGEFLIS
SEQ ID NO: 10       DIQTQNAAGASPPIAGIFVVYDLPDRDCSALASNGEYSIS
SEQ ID NO: 11       NIEAANKAGASPPIAGIFVVYDLPDRDCAAAASNGEYTVA
SEQ ID NO: 12       DIQSQNAAGADPPIAGIFVVYDLPDRDCAAAASNGEFSIA
SEQ ID NO: 13       DIRKANKAGGN--YAGQFVVYDLPDRDCAAAASNGEYSLD
SEQ ID NO: 14       DIRKANKAGGK--YAGQFVVYDLPNRDCAAAASNGEYSLD
SEQ ID NO: 15       EIRAANKAGANPPYAAHFVVYDLPDRDCAAAASNGEFSIA
SEQ ID NO: 16       DIKEQNDAGANPPIAGIFVVYNLPDRDCAALASNGELSIA
SEQ ID NO: 17       DIQTQNAAGANPPIAGIFVVYDLPDRDCAALASNGEYAIS
SEQ ID NO: 18       DVRAANAAGGN--YAAQLVVYDLPDRDCAAAASNGEFSIA
SEQ ID NO: 19       EIRAANQRGANPPYAGIFVVYDLPDRDCAAAASNGEWSIA
SEQ ID NO: 20       EIRAANQRGANPPYAGIFVVYDLPDRDCAAAASNGEWSIA
SEQ ID NO: 21       DVRAANARGGN--YASILVVYNLPDRDCAAAASNGEFAIA
SEQ ID NO: 22       EIRAANQAGANPPYAAQIVVYDLPDRDCAAAASNGEWAIA
SEQ ID NO: 23       EIREANQAGANPQYAAQIVVYDLPDRDCAAAASNGEWAIA
SEQ ID NO: 24       DIKAKNAAGAN--LMGTFVVYDLPDRDCAALASNGELKID
SEQ ID NO: 25       DAR------SKN-QLVQIVVYDLPDRDCAALASNGEFSLA
SEQ ID NO: 26       DASALQKSSGQP-QVVQIVVYDLPDRDCAAKASNGEFSIA
SEQ ID NO: 27       DASAKQKSEGKN-YLVQIVVYDLPDRDCAALASNGEFTIA
SEQ ID NO: 28       DASAKQKSEGKN-YLVQIVVYDLPDRDCAALASNGEFTIA
SEQ ID NO: 29       GIQEANAAGQNPPYIGAIVVYDLPNRDCAAAASNGEFSLE
SEQ ID NO: 30       SASALGKSTGTK-QLVQIVIYDLPDRDCAAKASNGEFSIA
SEQ ID NO: 31       EASALGKSSGKK-YLVQIVVYDLPDRDCAALASNGEFSIA
SEQ ID NO: 32       DVPCENIVG-------LVIYDLPGRDCAAKASNGELKVG
SEQ ID NO: 33       DALSIQQSTGRN-QLVQIVVYDLPDRDCAALASNGEFSIA
SEQ ID NO: 34       DASSIQTKTGQK-QLVPIVVYELPDRDCAAKASNGEFSIA
SEQ ID NO: 35       DVPCDHILG-------LVIYDLPGRDCAAKASNGELAVG
SEQ ID NO: 36       DQPCDHILG-------LVIYDLPGRDCAAKASNGELKVG
```

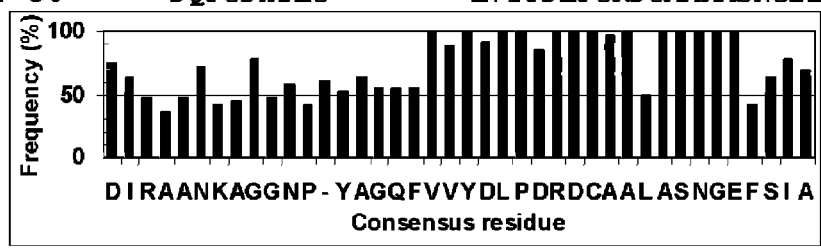

Figure 1 (Cont'd)

```
SEQ ID NO: 1    189 DGGVAKYK-NYIDTIRQIVV-----------------EY 209
CONSENSUS           DGGVAKYK-NYIDQIREILK-----------------EY
SEQ ID NO: 2        DGGVAKYK-NYIDTIRQIVV-----------------EY
SEQ ID NO: 3        DGGVAKYK-NYIDTIRQIVV-----------------EY
SEQ ID NO: 4        DGGVDKYK-NYIDTIRQIVV-----------------EY
SEQ ID NO: 5        DGGVDKYK-NYIDTIRQIVV-----------------EY
SEQ ID NO: 6        DGGVAKYK-NYIDTIRQIVV-----------------EY
SEQ ID NO: 7        DGGVQHYK-DYIDSIREILV-----------------EY
SEQ ID NO: 8        DNGVEHYK-SYIDSIREILV-----------------QY
SEQ ID NO: 9        DGGVEKYK-AYIDSIREQVE-----------------KY
SEQ ID NO: 10       DGGVEKYK-AYIDSIREQVE-----------------TY
SEQ ID NO: 11       NNGVANYK-AYIDSIVAQLK-----------------AY
SEQ ID NO: 12       NNGVALYK-QYIDSIREQLT-----------------TY
SEQ ID NO: 13       KDGKNKYK-AYIAD-QGILQ-----------------DY
SEQ ID NO: 14       KDGANKYK-AYIAKIKGILQ-----------------NY
SEQ ID NO: 15       NGGVANYK-TYINAIRKLLI-----------------EY
SEQ ID NO: 16       DGGVEKYK-EYIDAIRAHAV-----------------EY
SEQ ID NO: 17       DGGVEKYK-AYIDSIREQVE-----------------TY
SEQ ID NO: 18       DGGVVKYK-AYIDAIRKQLL-----------------AY
SEQ ID NO: 19       NNGANNYK-RYIDRIRELLI-----------------QY
SEQ ID NO: 20       NNGANNLQ-RYIDRIRELLI-----------------QY
SEQ ID NO: 21       DGGVAKYK-NYIDEIRKLVI-----------------KY
SEQ ID NO: 22       NNGANNYK-GYINRIREILI-----------------SF
SEQ ID NO: 23       NNGVNNYK-AYINRIREILI-----------------SF
SEQ ID NO: 24       EGGVEKYKTQYIDKIAAIIK-----------------KY
SEQ ID NO: 25       NDGLNKYK-NYVDQIAAQIK-----------------QF
SEQ ID NO: 26       DGGQAKYY-DYIDQIVAQIK-----------------KF
SEQ ID NO: 27       DNGEANYH-DYIDQIVAQIK-----------------QY
SEQ ID NO: 28       DNGEANYH-DYIDQIVAQIK-----------------QY
SEQ ID NO: 29       DGGEEKYR-GYIDGIREQIE-----------------KY
SEQ ID NO: 30       NNGQANYE-NYIDQIVAQIQ-----------------QF
SEQ ID NO: 31       NNGLNNYK-GYIDQLVAQIK-----------------KY
SEQ ID NO: 32       --ELDRYKTEYIDKIAEILK-----------------AH
SEQ ID NO: 33       NNGLANYK-NYVDQIVAQIARTCCPLVTSAITDLACLSEY
SEQ ID NO: 34       DAGAENYK-DYIDQIVPQIK-----------------QF
SEQ ID NO: 35       --ELSRYKTEYIDAIVKILK-----------------AH
SEQ ID NO: 36       --ELAKYKSQYIDPIAALLK-----------------KY
```

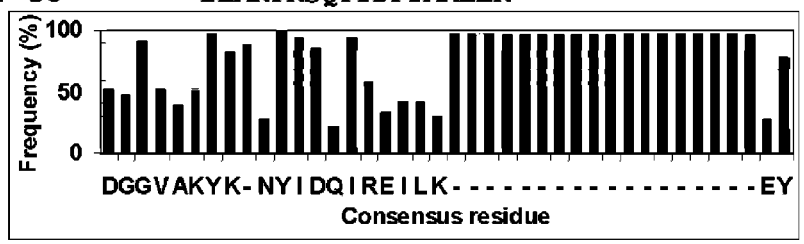

Figure 1 (Cont'd)

```
SEQ ID NO:  1    210  SDIRTLLVIEPDSLANLVTNLGTPKCANAQSAYLECINYA  249
CONSENSUS             SDVRTILVIEPDSLANLVTNLNVPKCANAQSAYLECTNYA
SEQ ID NO:  2         SDIRTLLVIEPDSLANLVTNLGTPKCANAQSAYLECINYA
SEQ ID NO:  3         SDIRTLLVIEPDSLANLVTNLGTPKCANAPSAYLECINYA
SEQ ID NO:  4         SDIRTLLVIEPDSLANLVTNLGTPKCANAQSAYLECINYA
SEQ ID NO:  5         SDIRTLLVIEPDSLANLVTNLGTPKCANAQSAYLECINYA
SEQ ID NO:  6         SDIRTILVIEPDSLANLVTNLGTPKCANAQSAYLECINYA
SEQ ID NO:  7         SDVHVILVIEPDSLANLVTNLNVAKCANAQSAYLECTNYA
SEQ ID NO:  8         SDVHTLLVIEPDSLANLVTNLNVAKCANAESAYLECTNYA
SEQ ID NO:  9         SDTQIILVIEPDSLANLVTNLNVQKCANAQDAYLECTNYA
SEQ ID NO: 10         SDVQTILIIEPDSLANLVTNLDVAKCANAESAYLECTNYA
SEQ ID NO: 11         PDVHTILIIEPDSLANMVTNLSTAKCAEAQSAYYECVNYA
SEQ ID NO: 12         SDVHTILVIEPDSLANVVTNLNVPKCANAQDAYLECINYA
SEQ ID NO: 13         SDTRIILVIEPDSLANMVTNMNVPKCANAASAYKELTIHA
SEQ ID NO: 14         SDTKVILVIEPDSLANLVTNLNVDKCAKAESAYKELTVYA
SEQ ID NO: 15         SDIRTILVIEPDSLANLVTNTNVAKCANAASAYRECTNYA
SEQ ID NO: 16         SDTNIILIIEPDSLANLVTNLNVEKCANAQDAYLECTNYA
SEQ ID NO: 17         SDVQTILIIEPDSLANLVTNLDVAKCANAQSAYLECTNYA
SEQ ID NO: 18         SDVRTILVIEPDSLANMVTNMGVPKCAGAKDAYLECTIYA
SEQ ID NO: 19         SDIRTILVIEPDSLANMVTNMNVQKCSNAASTYKELTVYA
SEQ ID NO: 20         SDIRTILVIEPDSLANMVTNMNVQKCSNAASTYKELTVYA
SEQ ID NO: 21         NDLRIILVIEPDSLANMVTNMNVAKCQNAASAYRECTNYA
SEQ ID NO: 22         SDVRTILVIEPDSLANMVTNMNVAKCSGAASTYRELTIYA
SEQ ID NO: 23         SDVRTILVIEPDSLANMVTNMNVPKCSGAASTYRELTIYA
SEQ ID NO: 24         PDVKINLAIEPDSLANMVTNMGVQKCSRAAPYYKELTAYA
SEQ ID NO: 25         PDVSVVAVIEPDSLANLVTNLNVQKCANAQSAYKEGVIYA
SEQ ID NO: 26         PDVRVIAVIEPDSLANLVTNLNVQKCANAQTTYKACVTYA
SEQ ID NO: 27         PDVHVVAVIEPDSLANLVTNLSVAKCANAQTTYLECVTYA
SEQ ID NO: 28         PDVHVVAVIEPDSLANLVTNLSVAKCANAQTTYLECVTYA
SEQ ID NO: 29         PDVRVALVIEPDSLANMVTNLNVPKCAESEQAYRDGVAYA
SEQ ID NO: 30         PDVRVVAVIEPDSLANLVTNLNVQKCANAKTTYLACVNYA
SEQ ID NO: 31         PDVRVVAVIEPDSLANLVTNLNVSKCANAQTAYKAGVTYA
SEQ ID NO: 32         SNTAFALVIEPDSLPNLVTNSDLQTCQQSASGYREGVAYA
SEQ ID NO: 33         PQIRVVAVVEPDSLANMVTNLNVPKCAGAQAAYTEGVTYA
SEQ ID NO: 34         PDVRVVAVIEPDSLANLVTNLNVQKCANGG-TYKASVTYA
SEQ ID NO: 35         PKTAFALVIEPDSLPNLVTNSDLQTCKDSASGYRDGVAYA
SEQ ID NO: 36         NNHAFALLIEPDSLPNLVTNSDLSACQQSAAGYRDGVAYA
```

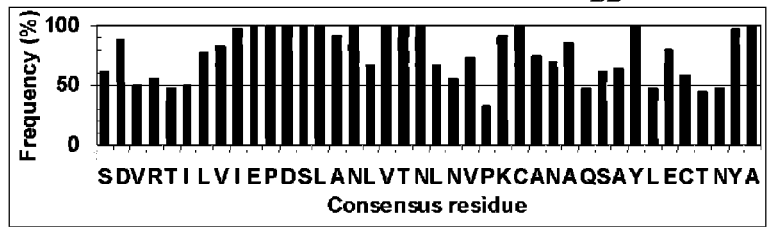

Figure 1 (Cont'd)

```
SEQ ID NO: 1    250 VTQLNLPNVAMYLDAGHAGWLGWPANQDPAAQLFANVYKN 289
CONSENSUS           LTQLNLPNVAMYLDAGHAGWLGWPANIQPAAQLFASVYKN
SEQ ID NO: 2        VTQLNLPNVAMYLDAGHAGWLGWPANQDPAAQLFANVYKN
SEQ ID NO: 3        VTQLNLPNVAMYLDAGHAGWLGWPANQDPAAQLFANVYKN
SEQ ID NO: 4        VTQLNLPNVAMYLDAGHAGWLGWPANQDPAAQLFANVYKN
SEQ ID NO: 5        VTQLNLPNVAMYLDAGHAGWLGWPANQDPAAQLFANVYKN
SEQ ID NO: 6        ITQLNLPNIAMYLDAGHAGWLGWPANQDPAAQLFANVYKN
SEQ ID NO: 7        VTQLNLPNVAMYLDAGHAGWLGWPANLQPAANLYAGVYSD
SEQ ID NO: 8        LTQLNLPNVAMYLDAGHAGWLGWPANQQPAADLFASVYKN
SEQ ID NO: 9        LTQLNLPNVAMYLDAGHAGWLGWPANIGPAAELYASVYKN
SEQ ID NO: 10       LEQLNLPNVAMYLDAGHAGWLGWPANIGPAAQLYASVYKN
SEQ ID NO: 11       LINLNLANVAMYIDAGHAGWLGWSANLSPAAQLFATVYKN
SEQ ID NO: 12       ITQLDLPNVAMYLDAGHAGWLGWQANLAPAAQLFASVYKN
SEQ ID NO: 13       LKELNLPNVSMYIDAGHGGWLGWPANLPPAAQLYGQLYKD
SEQ ID NO: 14       IKELNLPNVSMYLDAGHGGWLGWPANIGPAAKLYAQIYKD
SEQ ID NO: 15       ITQLDLPHVAQYLDAGHGGWLGWPANIQPAATLFADIYKA
SEQ ID NO: 16       ITQLDLPNVSMYLDAGHAGWLGWPANIGPAAQLFAGVYQD
SEQ ID NO: 17       LEQLNLPNVAMYLDAGHAGWLGWPANIGPAAELYASVYKN
SEQ ID NO: 18       VKQLNLPHVAMYLDGGHAGWLGWPANLQPAADLFGKLYAD
SEQ ID NO: 19       LKQLNLPHVAMYMDAGHAGWLGWPANIQPAAELFAQIYRD
SEQ ID NO: 20       LKQLNLPHVAMYMDAGHAGWLGWPANIQPAAELFAQIYRD
SEQ ID NO: 21       LTNLDLPNVAQYMDAGHAGWLGWPANITPAAQLFAEVYKQ
SEQ ID NO: 22       LKQLDLPHVAMYMDAGHAGWLGWPANIQPAAELFAKIYED
SEQ ID NO: 23       LKQLDLPHVAMYMDAGHAGWLGWPANIQPAAELFAKIYED
SEQ ID NO: 24       LKTLNFNNVDMYMDGGHAGWLGWDANIGPTAKLFAEVYKA
SEQ ID NO: 25       VQKLNAVGVTMYIDAGHAGWLGWPANLSPAAQLFAQIYRD
SEQ ID NO: 26       LNQLASVGVYQYMDAGHAGWLGWPANIQPAAQLFADMFKS
SEQ ID NO: 27       MQQLSAVGVTMYLDAGHAGWLGWPANLSPAAQLFTSLYSN
SEQ ID NO: 28       MQQLSAVGVTMYLDAGHAGWLGWPANLSPAAQLFTSLYSN
SEQ ID NO: 29       LKQLDLPNVWTYIDAGHSGWLGWPANIEPAAEIFVEVWNA
SEQ ID NO: 30       LTNLAKVGVYMYMDAGHAGWLGWPANLSPAAQLFTQVWQN
SEQ ID NO: 31       LQQLNSVGVYMYLDAGHAGWLGWPANLNPAAQLFSQLYRD
SEQ ID NO: 32       LKQLNLPNVVMYIDAGHGGWLGWDANLKPGAQELASVYKS
SEQ ID NO: 33       LQKLNTVGVYSYVDAGHAGWLGWPANLGPAAQLFANLYTN
SEQ ID NO: 34       LQQLSSVGVTMYMDAGHAGWLGWPANIQPGSEVFAEMFKS
SEQ ID NO: 35       LRNLNLPNVVMYIDAGHGGWLGWDANLKPGAQELAKAYKA
SEQ ID NO: 36       LKTLNLPNVVMYIDAGHGGWLGWNDNLKPGAEELAKAYKA
```

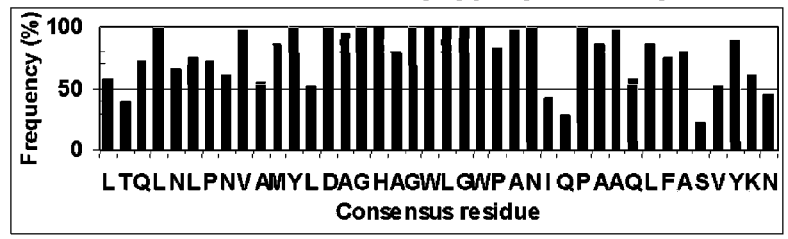

Figure 1 (Cont'd)

```
SEQ ID NO: 1      290  ASSPRALRGLATNVANYNGWNIT----SPPSYT*QGNAVYN 325
CONSENSUS              AGSPAAVRGLATNVANYNAWSIS----SPPSYTQGNPNYD
SEQ ID NO: 2           ASSPRALRGLATNVANYNGWNIT----SPPSYTQGNAVYN
SEQ ID NO: 3           ASSPRALRGLATNVANYNGWNIT----SPPSYTQGNAVYN
SEQ ID NO: 4           ASSPRALRGLATNVANYNGWNIT----SPPSYTQGNAVYN
SEQ ID NO: 5           ASSPRALRGLATNVANYNGWNIT----SPPSYTQGNAVYN
SEQ ID NO: 6           ASSPSALRGLATNVANYNGWNIT----SPPSYTQGNAVYN
SEQ ID NO: 7           AGSPAALRGLATNVANYNAWAID----TCPSYTQGNSVCD
SEQ ID NO: 8           ASSPAAVRGLATNVANYNAWTIS----SCPSYTQGNSVCD
SEQ ID NO: 9           ASSPAAVRGLATNVANYNAFSID----SCPSYTQGSTVCD
SEQ ID NO: 10          ASSPAAVRGLATNVANFNAWSID----SCPSYTSGNDVCD
SEQ ID NO: 11          ASAPASLRGLATNVANYNAWSIS----SPPSYTSGDSNYD
SEQ ID NO: 12          ASSPASVRGLATNVANYNAWSIS----RCPSYTQGDANCD
SEQ ID NO: 13          AGKPSRLRGLVTNVSNYNAWKLS----SKPDYTESNPNYD
SEQ ID NO: 14          AGKPSRVRGLVTNVSNYNGWKLS----TKPDYTESNPNYD
SEQ ID NO: 15          AGKPKSVRGLVTNVSNYNGWSLS----SAPSYTTPNPNYD
SEQ ID NO: 16          AGAPAALRGLATNVANYNAFSID----TCPSYTSQNAVCD
SEQ ID NO: 17          ASSPAAVRGLATBVANFNAWSID----TCPSYTSGNDVCD
SEQ ID NO: 18          AGKPSQLRGMATNVANYNAWDLT----TAPSYTTPNPNFD
SEQ ID NO: 19          AGRPAAVRGLATNVANYNAWSIA----SPPSYTSPNPNYD
SEQ ID NO: 20          AGRPAAVRGLATNVANYNAWSIA----SPPSYTSPNPNYD
SEQ ID NO: 21          AGSPKSVRGLAINVSNYNAWSVS----SPPPYTSPNPNYD
SEQ ID NO: 22          AGKPRAVRGLATNVANYNAWSIS----SPPPYTSPNPNYD
SEQ ID NO: 23          AGKPRAVRGLATNVANYNAWSVS----SPPPYTSPNPNYD
SEQ ID NO: 24          AGSPRGVRGIVTNVSNYNALRVS----SCPSITQGNKNCD
SEQ ID NO: 25          AGSPRNLRGIATNVANFNALRAS----SPDPITQGNSNYD
SEQ ID NO: 26          ANSSKFVRGLATNVANYNALSAA----SPDPITQGDPNYD
SEQ ID NO: 27          AGSPSGVRGLATNVANYNALVAT----TPDPITQGDPNYD
SEQ ID NO: 28          AGSPSGVRGLATNVANYNALVAT----TPDPITQGDPNYD
SEQ ID NO: 29          AGRPKSTRGFATNVSNYNGYSLS----TAPPYTEPNPNFD
SEQ ID NO: 30          AGKSPFIKGLATNVANYNALQAA----SPDPITQGNPNYD
SEQ ID NO: 31          AGSPQYVRGLATNVANYNALSAS----SPDPVTQGNPNYD
SEQ ID NO: 32          AGSPSQVRGISTNVAGWNAWDQEPGEFSDASDAQYNKCQN
SEQ ID NO: 33          AGSPSFFRGLATNVANYNLLNAP----SPDPVTSPNANYD
SEQ ID NO: 34          ADFVAFVRAFATNVREYNALTAA----FPRPITQGNPNYD
SEQ ID NO: 35          AGSPKQVRGIATNVAGWNQWDLTPGEFSKASDAKYNKCQN
SEQ ID NO: 36          AGSPKQFRGFATNVAGWNAWDLTPGEFSSASDAQWNKCQN
```

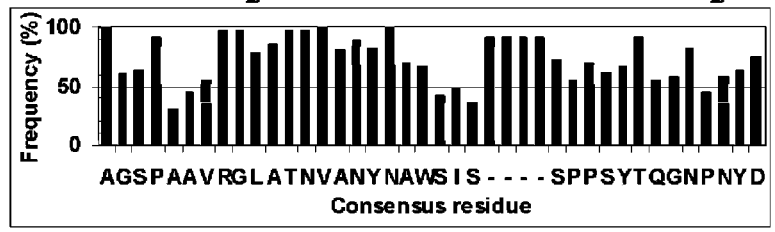

Figure 1 (Cont'd)

```
SEQ ID NO: 1    326  EKLYIH----------------AIGPLLANHGWSNAFFI  348
CONSENSUS            EKLYIN----------------AFAPLLANAGFP-AHFI
SEQ ID NO: 2         EKLYIH----------------AIGRLLANHGWSNAFFI
SEQ ID NO: 3         EKLYIH----------------AIGPLLANHGWSNAFFI
SEQ ID NO: 4         EQLYIH----------------AIGPLLANHGWSNAFFI
SEQ ID NO: 5         EQLYIH----------------AIGPLLANHGWSNAFFI
SEQ ID NO: 6         EKLYIH----------------AIGPLLANHGWSNAFFI
SEQ ID NO: 7         EKDYIN----------------ALAPLLRAQGFD-AHFI
SEQ ID NO: 8         EQQYIN----------------AIAPLLQAQGFD-AHFI
SEQ ID NO: 9         EKTYIN----------------NFAPQLKSAGFD-AHFI
SEQ ID NO: 10        EKSYIN----------------AIAPELSSAGFD-AHFI
SEQ ID NO: 11        EKLYIN----------------ALSPLLTSNGWPNAHFI
SEQ ID NO: 12        EEDYVN----------------ALGPLFQEQGFP-AYFI
SEQ ID NO: 13        EQKYIH----------------ALSPLLEQEGWPGAKFI
SEQ ID NO: 14        EQRYIN----------------AFAPLLAQEGWSNVKFI
SEQ ID NO: 15        EKKYIE----------------AFSPLLNAAGFP-AQFI
SEQ ID NO: 16        EKGYIN----------------SFAPELSAAGWD-AHFI
SEQ ID NO: 17        EKSYIN----------------AFAPELSXAGFD-AHFI
SEQ ID NO: 18        EKKYIS----------------AFAPLLAAKGWS-AHFI
SEQ ID NO: 19        EKHYIE----------------AFAPLLRNQGFD-AKFI
SEQ ID NO: 20        EKHYIE----------------AFAPLLRNQGFD-AKFI
SEQ ID NO: 21        ERHFVE----------------AFAPLLRQNGWD-AKFI
SEQ ID NO: 22        EKHYIE----------------AFRPLLEARGFP-AQFI
SEQ ID NO: 23        EKHYIE----------------AFRPLLEARGFP-AQFI
SEQ ID NO: 24        EERYIN----------------ALAPLLKNEGFP-AHFI
SEQ ID NO: 25        EIHYI-----------------EALAPMLSNAGFP-AHFI
SEQ ID NO: 26        ELHYIN----------------ALGPMLAQQGFP-AQFV
SEQ ID NO: 27        EMLYIE----------------ALAPLLGS--FP-AHFI
SEQ ID NO: 28        EMLYIE----------------ALAPLLGS--FP-AHFI
SEQ ID NO: 29        EVRYIN----------------AFRPLLEARGFP-AYFI
SEQ ID NO: 30        EIHYIN----------------ALAPLLQQAGWD-ATFI
SEQ ID NO: 31        ELHYIN----------------ALAPALQSGGFP-AHFI
SEQ ID NO: 32        EKIYIN----------------TFGAELKSAGMP-NHAI
SEQ ID NO: 33        EIHYINVSDCFVLIWTSLTICIIALAPELSSRGFP-AHFI
SEQ ID NO: 34        EFPYIQ----------------RVRPMLKSPGFP-AQFV
SEQ ID NO: 35        EKLYLD----------------NFGPALKSAGMP-NHAI
SEQ ID NO: 36        EKIYVE----------------TFGPLLKNAGMP-NHAI
```

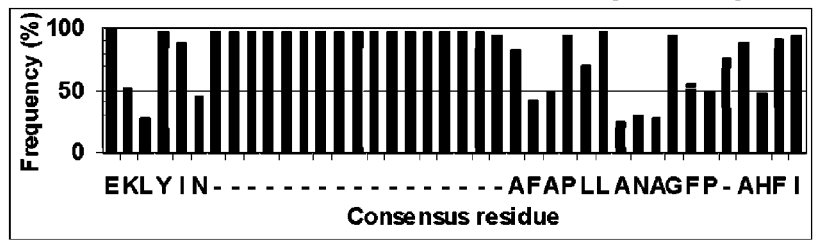

Figure 1 (Cont'd)

```
SEQ ID NO: 1    349  TDQGRSGKQPTGQQQWGDWCNVIGTGFGIRPSANTGDSLL  388
CONSENSUS            VDQGRSGKQPTGQQQWGDWCNVIGTGFGVRPTTNTGDSLV
SEQ ID NO: 2         TDQGRSGKQPTGQQQWGDWCNVIGTGFGIRPSANTGDSLL
SEQ ID NO: 3         TDQGRSGKQPTGQQQWGDWCNVIGTGFGIRPSANTGDSLL
SEQ ID NO: 4         TDQGRSGKQPTGQQQWGDWCNVIGTGFGIRPSANTGDSLL
SEQ ID NO: 5         TDQGRSGKQPTGQQQWGDWCNVIGTGFGIRPSANTGDSLL
SEQ ID NO: 6         TDQGRSGKQPTGQQQWGDWCNVIGTGFGIRPSSNTGDSLL
SEQ ID NO: 7         TDTGRNGKQPTGQQAWGDWCNVIGTGFGARPSTNTGDSLL
SEQ ID NO: 8         VDTGRNGKQPTGQQAWGDWCNVINTGFGERPTTDTGDALV
SEQ ID NO: 9         VDTGRNGNQPTGQSQWGDWCNVKNTGFGVRPTTDTGDELV
SEQ ID NO: 10        TDTGRNGKQPTGQSAWGDWCNVKDTGFGAQPTTDTGDELA
SEQ ID NO: 11        MDTSRNGVQPTKQQAWGDWCNVIGTGFGVQPTTNTGDPLE
SEQ ID NO: 12        IDTSRNGVRPTKQSQWGDWCNVIGTGFGVRPTTDTGNPLE
SEQ ID NO: 13        VDQGRSGKQPTGQKAWGDWCNAPGTGFGLRPSANTGDALV
SEQ ID NO: 14        VDQGRSGKQPTGQKAQGDWCNAKGTGFGLRPSTNTGDALA
SEQ ID NO: 15        VDTGRSGKQPTGQIEQGDWCNAIGTGFGVRPTTNTGSSLA
SEQ ID NO: 16        VDTGRNGKQPTGQIEWGDWCNVKGTGFGVRPTTDTGDELV
SEQ ID NO: 17        TDTGRNGKQPTGQSAWGDWGNVKDTGFGAXPTTDTGNELA
SEQ ID NO: 18        IDQGRSGKQPTGQKEWGHWCNQQGVGFGRRPSANTGSELA
SEQ ID NO: 19        VDTGRNGKQPTGQLEWGHWCNVKGTGFGVRPTANTGHELV
SEQ ID NO: 20        VDTGRNGKQPTGQLEWGHWCNVKGTGFGVRPTANTGHELV
SEQ ID NO: 21        VDQGRSGRQPTGQQEWGHWCNAIGTGFGQRPTSNTGHADV
SEQ ID NO: 22        VDQGRSGKQPTGQKEWGHWCNAIGTGFGMRPTANTGHQYV
SEQ ID NO: 23        VDQGRSGKQPTGQKEWGHWCNAIGTGFGMRPTANTGHQYV
SEQ ID NO: 24        VDQGRSGKVPTNQQEWGDWCNVSGAGFGTRPTTNTGNALI
SEQ ID NO: 25        VDQGRSGVQ-NIRDQWGDWCNVKGAGFGQRPTTNTGSSLI
SEQ ID NO: 26        VDQGRSGQQ-NLRQQWGDWCNIKGAGFGTRPTTNTGSSLI
SEQ ID NO: 27        VDQGRSGVQ-DIRQQWGDWCNVLGAGFGTQPTTNTGSSLI
SEQ ID NO: 28        VDQGRSGVQ-DIRQQWGDWCNVLGAGFGTQPTTNTGSSLI
SEQ ID NO: 29        VDQGRSGVQPTAQIEQGHWCNVIDTGFGTRPTTDTGNEYV
SEQ ID NO: 30        VDQGRSGVQ-NIRQQWGDWCNIKGAGFGTRPTTNTGSQFI
SEQ ID NO: 31        VDQGRSGVQ-NIRQQWGDWCNVKGAGFGQRPTLSTGSSLI
SEQ ID NO: 32        IDTGRNGVT-GLRDEWGDWCNVNGAGFGVRPTANTGDELA
SEQ ID NO: 33        VDQGRSAVQ-GIRGAWGDWCNVDNAGFGTRPTTSTGSSLI
SEQ ID NO: 34        VDQGRAGQQ-NFRQQWGDWCNIKGAGFGTRPTTSTGNPLI
SEQ ID NO: 35        VDTGRNGVS-GLRQEWGNWCNVNGAGFGVRPTSSTGHDLA
SEQ ID NO: 36        VDVGRNAVQ-GLREEWGHWCNVNGAGFGVRPTTSTGSSLT
```

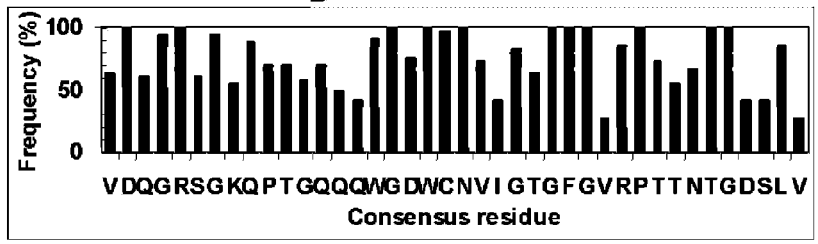

Figure 1 (Cont'd)

```
SEQ ID NO: 1     389 DSFVWVKPGGECDGTS-DSSAPRFDSHCALP-DALQPAPQ 426
CONSENSUS            DAFVWVKPGGESDGTS-DTSAPRYDSHCGLS-DALQPAPE
SEQ ID NO: 2         DSFVWVKPGGECDGTS-DSSAPRFDSHCALP-DALQPAPQ
SEQ ID NO: 3         DSFVWVKPGGECDGTS-DSSAPRFDSHCALP-DALQPAPQ
SEQ ID NO: 4         DSFVWIKPGGECDGTS-DSSAPRFDSHCALP-DALQPAPQ
SEQ ID NO: 5         DSFVWIKPGGECDGTS-DSSAPRFDSHCALP-DALQPAPQ
SEQ ID NO: 6         DSFVWVKPGGECDGTS-DSSAPRFDSHCALP-DALQPAPQ
SEQ ID NO: 7         DAFVWVKPGGESDGTS-DTSAARYDAHCGYS-DALQPAPE
SEQ ID NO: 8         DAFVWVKPGGESDGTS-DSSATRYDAHCGYS-DALQPAPE
SEQ ID NO: 9         DAFVWVKPGGESDGTS-DTSAERYDAHCGYA-DALTPAPE
SEQ ID NO: 10        DAFVWVKPGGESDGTS-DTSSSRYDAHCGYS-DALQPAPE
SEQ ID NO: 11        DAFVWVKPGGESDGTS-NSSATRYDFHCGYS-DALQPAPE
SEQ ID NO: 12        DAFVWVKPGGESDGTS-NTTSPRYDYHCGLS-DALQPAPE
SEQ ID NO: 13        DAFVWVKPGGESDGTS-DTSAARYDYHCGID-GAVKPAPE
SEQ ID NO: 14        DAFVWVKPGGESDGTS-DTSAARYDYHCGLD-DALKPAPE
SEQ ID NO: 15        DAFVWVKPGGESDGTS-DTSATRYDYHCGLS-DALKPAPE
SEQ ID NO: 16        DAFVWVKPGGESDGTS-DQSAERYDAHCGAA-AALQPAPE
SEQ ID NO: 17        DAFVWXNPGGKSDGTS-DTSSSRYDAHCGYS-DALQPAPE
SEQ ID NO: 18        DAFVWIKPGGECDGVS-DPTAPRFDHFCGTDYGAMSDAPQ
SEQ ID NO: 19        DAFVWVKPGGESDGTSADTSAARYDYHCGLS-DALTPAPE
SEQ ID NO: 20        DAFVWVKPGGESDGTS-DTSAARYDYHCGLS-DALTPAPE
SEQ ID NO: 21        DAFVWIKPGGECDGTS-DTSAARYDHFCGNP-DALKPAPE
SEQ ID NO: 22        DAFVWVKPGGECDGTS-DTTAARYDYHCGLE-DALKPAPE
SEQ ID NO: 23        DAFVWVKPGGECDGTS-DTTAARYDYHCGLE-DALKPAPE
SEQ ID NO: 24        DAIVWVKPGGESDGTS-DTSAARYDAHCGRN-SAFKPAPE
SEQ ID NO: 25        DAIVWVKPGGECDGTS-DNSSPRFDSHCSLS-DAHQPAPE
SEQ ID NO: 26        DAIVWVKPGGESDGTS-NSSSPRFDSTCSLS-DATQPAPE
SEQ ID NO: 27        DSIVWVKPGGECDGTS-NTSSPRYDAHCGLP-DATPNAPE
SEQ ID NO: 28        DSIVWVKPGGECDGTS-NTSSPRYDAHCGLP-DATPNAPE
SEQ ID NO: 29        DSIVWVKPGGESDGTS-DTSAERYDYHCGLE-DALKPAPE
SEQ ID NO: 30        DSIVWVKPGGECDGTS-NSSSPRYDSTCSLP-DAAQPAPE
SEQ ID NO: 31        DAIVWIKPGGECDGTT-NTSSPRYDSHCGLS-DATPNAPE
SEQ ID NO: 32        DAFVWVKPGGESDGTS-DSSAARYDSFCGKP-DAFKPSPE
SEQ ID NO: 33        DAIVWVKPGGESDGTS-DTSAVRYDGHCGLA-SAKKPAPE
SEQ ID NO: 34        DAIIWVKPGGESDGTS-NSSSPRYDSTLLSV-RRDDPAPE
SEQ ID NO: 35        DAFVWVKPGGESDGTS-DSSATRYDSFCGKS-DAYQPSPE
SEQ ID NO: 36        DALLWVKPGGESDGTS-DTSATRYDSFCGMS-DAYKPSPE
```

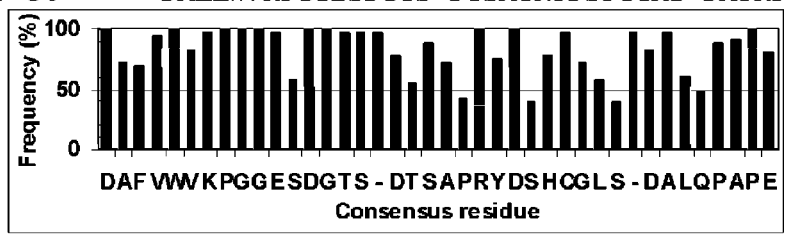

Figure 1 (Cont'd)

```
SEQ ID NO: 1    427  AG------AWFQAYFVQLLTNANPSFL-  447
CONSENSUS            AG------TWFQAYFEQLLTNANPSF--
SEQ ID NO: 2         AG------AWFQAYFVQLLTNANPSFL-
SEQ ID NO: 3         AG------AWFQAYFVQLLTNANPSFL-
SEQ ID NO: 4         AG------AWFQAYFVQLLTNANPSFL-
SEQ ID NO: 5         AG------AWFQAYFVQLLTNANPSFL-
SEQ ID NO: 6         AG------AWFQAYFVQLLTNANPSFL-
SEQ ID NO: 7         AG------TWFQAYFVQLLQNANPSF--
SEQ ID NO: 8         AG------TWFQAYFVQLLTNANPAF--
SEQ ID NO: 9         AG------TWFQAYFEQLVENANPSL--
SEQ ID NO: 10        AG------TWFQAYFEQLLTNANPSL--
SEQ ID NO: 11        AG------TWFQAYFVQLLTNANPALV-
SEQ ID NO: 12        AG------TWFQAYFEQLLTNANPLF--
SEQ ID NO: 13        AG------TWFQAYFEQLLKNANPSFL-
SEQ ID NO: 14        AG------TWFQAYFEQLLDNANPSFL-
SEQ ID NO: 15        AG------QWFQAYFEQLLKNANPAF--
SEQ ID NO: 16        AG------TWFQAYFEQLVANANPPLSS
SEQ ID NO: 17        AG------TWFQAYFEQLLTNANPSL--
SEQ ID NO: 18        AG------QWFQKYFEMLLTNANPPL--
SEQ ID NO: 19        AG------QWFQAYFEQLLINANPPL--
SEQ ID NO: 20        AG------QWFQAYFEQLLINANPPF--
SEQ ID NO: 21        AG------EWFQAYFEQLLRNANPAF--
SEQ ID NO: 22        AG------QWFQAYFEQLLRNANPPF--
SEQ ID NO: 23        AG------QWFNEYFIQLLRNANPPF--
SEQ ID NO: 24        AG------TWFQAYFEMLLKNANPALA-
SEQ ID NO: 25        AG------TWFQAYFETLVANANPAL--
SEQ ID NO: 26        AG------TWFQTYFETLVSKANPPL--
SEQ ID NO: 27        AG------TWFQAYFETLVEKANPPL--
SEQ ID NO: 28        AG------TWFQAYFETLVEKANPPL--
SEQ ID NO: 29        AG------QWFQAYFEQLLRNANPPF--
SEQ ID NO: 30        AG------TWFQAYFQTLVSAANPPL--
SEQ ID NO: 31        AG------QWFQAYFETLVRNASPPL--
SEQ ID NO: 32        AG------TWNQAYFEMLLKNANPSF--
SEQ ID NO: 33        AMASVYSHSSFQAYFEMLVANAVPAL--
SEQ ID NO: 34        AG------TWFQAYFETLVSKPTRPL--
SEQ ID NO: 35        AG------SWNQDYFEMLVKNAKPSF--
SEQ ID NO: 36        AG------QWNQDYFEMLLRNAKPQF--
```

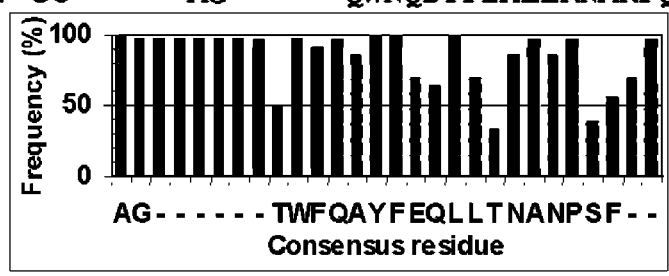

Figure 1 (Cont'd)

A
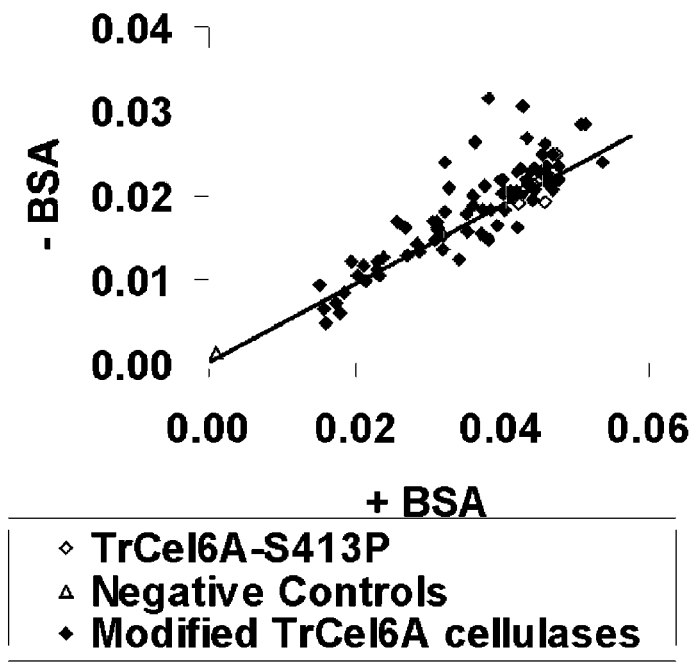
B
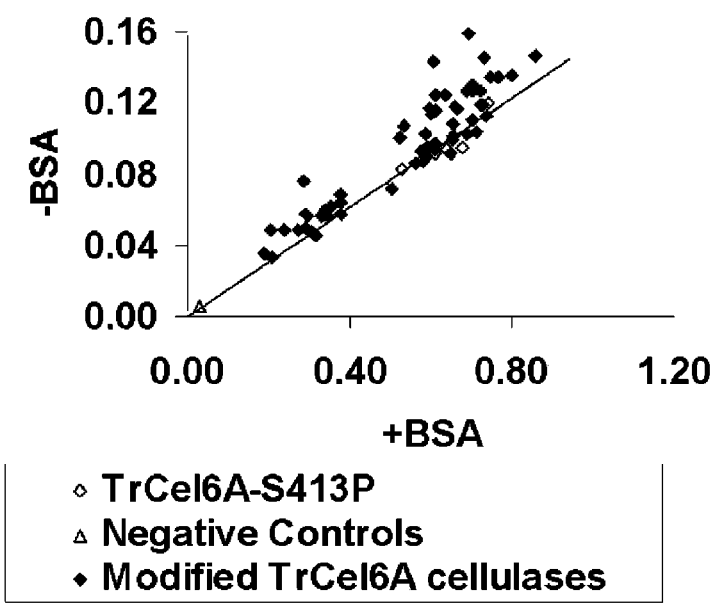
Figure 3

A
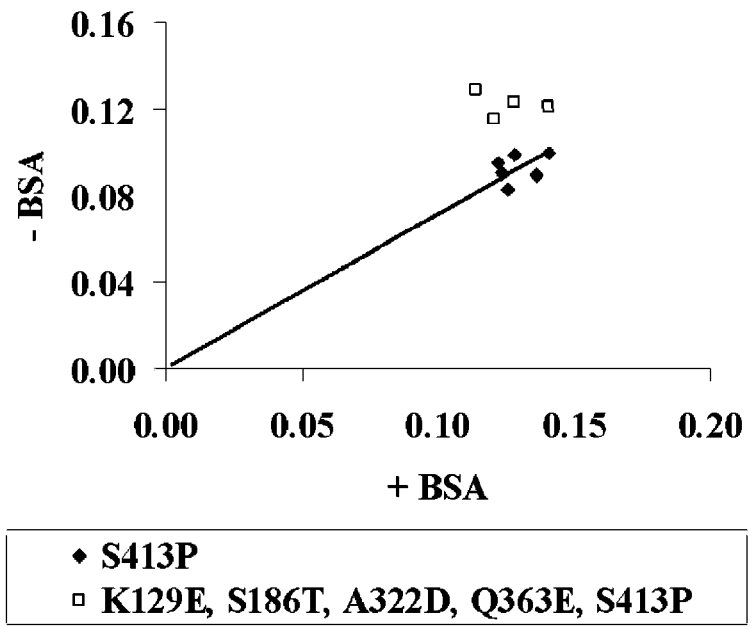
B
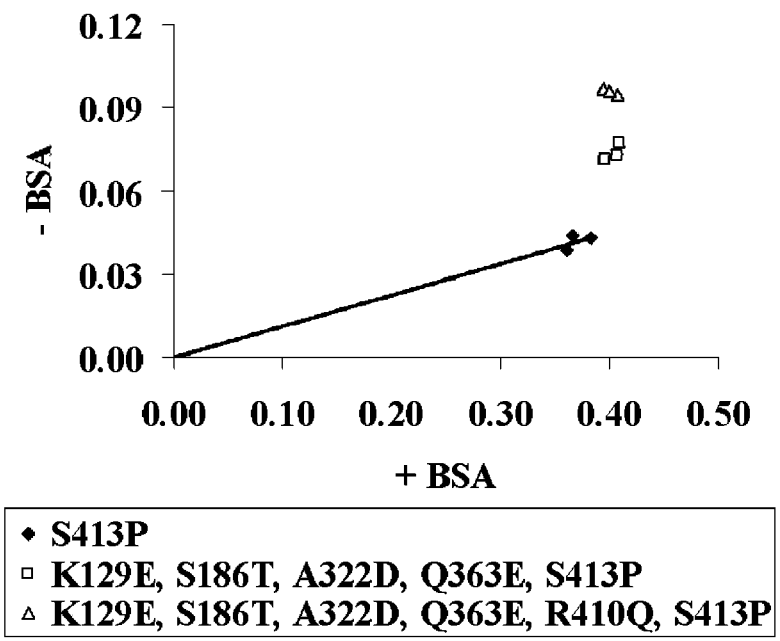
Figure 5

| | Tr Cel6A (SEQ ID NO: 1) | Hk Cbh2 (SEQ ID NO: 2) | Tv Cbh2 (SEQ ID NO: 3) | Hk Cbh2 (SEQ ID NO: 4) | Hk Cbh2 (SEQ ID NO: 5) | Tp CbhII (SEQ ID NO: 6) | An AN5282.2 (SEQ ID NO: 7) | An An12g02220 (SEQ ID NO: 8) | Ao AO090038000439 (SEQ ID NO: 9) | An An08g01760 (SEQ ID NO: 10) | Ac Acc2 (SEQ ID NO: 11) | Te CbhII (SEQ ID NO: 12) | Gz Cel6 (SEQ ID NO: 13) | Fo EglB (SEQ ID NO: 14) | Nc NCU09680.1 (SEQ ID NO: 15) | An AN1273.2 (SEQ ID NO: 16) | At Unnamed (SEQ ID NO: 17) | Mg MG05520.4 (SEQ ID NO: 18) |
|---|---|---|---|---|---|---|---|---|---|---|---|---|---|---|---|---|---|---|
| Tr Cel6A (SEQ ID NO: 1) | ID | 0.989 | 0.989 | 0.980 | 0.978 | 0.978 | 0.724 | 0.724 | 0.678 | 0.676 | 0.673 | 0.667 | 0.656 | 0.656 | 0.658 | 0.654 | 0.654 | 0.653 |
| Hk Cbh2 (SEQ ID NO: 2) | 0.989 | ID | 0.994 | 0.986 | 0.983 | 0.983 | 0.727 | 0.727 | 0.681 | 0.679 | 0.675 | 0.670 | 0.659 | 0.659 | 0.661 | 0.657 | 0.657 | 0.656 |
| Tv Cbh2 (SEQ ID NO: 3) | 0.989 | 0.994 | ID | 0.986 | 0.983 | 0.983 | 0.727 | 0.730 | 0.681 | 0.682 | 0.675 | 0.670 | 0.662 | 0.662 | 0.663 | 0.657 | 0.657 | 0.659 |
| Hk Cbh2 (SEQ ID NO: 4) | 0.980 | 0.986 | 0.986 | ID | 0.997 | 0.975 | 0.724 | 0.730 | 0.678 | 0.678 | 0.676 | 0.670 | 0.667 | 0.662 | 0.655 | 0.654 | 0.657 | 0.659 |
| Hk Cbh2 (SEQ ID NO: 5) | 0.978 | 0.983 | 0.983 | 0.997 | ID | 0.972 | 0.722 | 0.727 | 0.675 | 0.673 | 0.667 | 0.664 | 0.659 | 0.659 | 0.653 | 0.652 | 0.654 | 0.656 |
| Tp CbhII (SEQ ID NO: 6) | 0.978 | 0.983 | 0.983 | 0.975 | 0.972 | ID | 0.727 | 0.724 | 0.684 | 0.682 | 0.678 | 0.675 | 0.662 | 0.667 | 0.666 | 0.663 | 0.660 | 0.656 |
| An AN5282.2 (SEQ ID NO: 7) | 0.724 | 0.727 | 0.727 | 0.724 | 0.722 | 0.727 | ID | 0.871 | 0.780 | 0.789 | 0.746 | 0.756 | 0.638 | 0.644 | 0.685 | 0.765 | 0.789 | 0.653 |
| An An12g02220 (SEQ ID NO: 8) | 0.724 | 0.727 | 0.730 | 0.730 | 0.727 | 0.724 | 0.871 | ID | 0.791 | 0.821 | 0.773 | 0.786 | 0.633 | 0.638 | 0.691 | 0.760 | 0.802 | 0.640 |
| Ao AO090038000439 (SEQ ID NO: 9) | 0.678 | 0.681 | 0.681 | 0.678 | 0.675 | 0.684 | 0.780 | 0.791 | ID | 0.840 | 0.697 | 0.740 | 0.606 | 0.617 | 0.664 | 0.807 | 0.831 | 0.618 |
| An An08g01760 (SEQ ID NO: 10) | 0.676 | 0.679 | 0.682 | 0.676 | 0.673 | 0.682 | 0.789 | 0.821 | 0.840 | ID | 0.736 | 0.760 | 0.604 | 0.621 | 0.665 | 0.772 | 0.953 | 0.621 |
| Ac Acc2 (SEQ ID NO: 11) | 0.673 | 0.675 | 0.675 | 0.670 | 0.667 | 0.678 | 0.746 | 0.773 | 0.697 | 0.736 | ID | 0.755 | 0.625 | 0.606 | 0.658 | 0.712 | 0.709 | 0.609 |
| Te CbhII (SEQ ID NO: 12) | 0.667 | 0.670 | 0.670 | 0.667 | 0.664 | 0.675 | 0.756 | 0.786 | 0.740 | 0.760 | 0.755 | ID | 0.595 | 0.598 | 0.675 | 0.703 | 0.746 | 0.618 |
| Gz Cel6 (SEQ ID NO: 13) | 0.656 | 0.659 | 0.662 | 0.662 | 0.659 | 0.662 | 0.638 | 0.633 | 0.606 | 0.604 | 0.625 | 0.595 | ID | 0.853 | 0.663 | 0.607 | 0.583 | 0.641 |
| Fo EglB (SEQ ID NO: 14) | 0.656 | 0.659 | 0.662 | 0.662 | 0.659 | 0.667 | 0.644 | 0.638 | 0.617 | 0.621 | 0.606 | 0.598 | 0.853 | ID | 0.679 | 0.621 | 0.604 | 0.613 |
| Nc NCU09680.1 (SEQ ID NO: 15) | 0.658 | 0.661 | 0.663 | 0.655 | 0.653 | 0.666 | 0.685 | 0.691 | 0.664 | 0.665 | 0.658 | 0.675 | 0.663 | 0.679 | ID | 0.669 | 0.649 | 0.676 |
| An AN1273.2 (SEQ ID NO: 16) | 0.654 | 0.657 | 0.657 | 0.654 | 0.652 | 0.663 | 0.765 | 0.760 | 0.807 | 0.772 | 0.712 | 0.703 | 0.607 | 0.621 | 0.669 | ID | 0.761 | 0.631 |
| At Unnamed (SEQ ID NO: 17) | 0.654 | 0.657 | 0.657 | 0.657 | 0.654 | 0.660 | 0.789 | 0.802 | 0.831 | 0.953 | 0.709 | 0.746 | 0.583 | 0.604 | 0.649 | 0.761 | ID | 0.619 |
| Mg MG05520.4 (SEQ ID NO: 18) | 0.653 | 0.656 | 0.659 | 0.659 | 0.656 | 0.656 | 0.653 | 0.640 | 0.618 | 0.621 | 0.609 | 0.618 | 0.641 | 0.613 | 0.676 | 0.631 | 0.619 | ID |
| Cl Unnamed (SEQ ID NO: 19) | 0.651 | 0.653 | 0.656 | 0.651 | 0.648 | 0.653 | 0.692 | 0.702 | 0.687 | 0.680 | 0.681 | 0.676 | 0.677 | 0.672 | 0.763 | 0.681 | 0.669 | 0.677 |
| Cl Cbh2 (SEQ ID NO: 20) | 0.650 | 0.653 | 0.655 | 0.650 | 0.647 | 0.653 | 0.691 | 0.702 | 0.681 | 0.673 | 0.674 | 0.675 | 0.676 | 0.671 | 0.763 | 0.674 | 0.663 | 0.671 |
| Sa Unnamed (SEQ ID NO: 21) | 0.648 | 0.651 | 0.653 | 0.653 | 0.651 | 0.656 | 0.625 | 0.620 | 0.618 | 0.605 | 0.603 | 0.601 | 0.671 | 0.657 | 0.707 | 0.614 | 0.597 | 0.636 |
| Hi Avi2 (SEQ ID NO: 22) | 0.636 | 0.639 | 0.642 | 0.636 | 0.633 | 0.636 | 0.658 | 0.669 | 0.634 | 0.632 | 0.639 | 0.645 | 0.674 | 0.658 | 0.771 | 0.631 | 0.627 | 0.684 |
| Hi Cel6A (SEQ ID NO: 23) | 0.631 | 0.633 | 0.636 | 0.631 | 0.628 | 0.631 | 0.644 | 0.653 | 0.620 | 0.613 | 0.625 | 0.631 | 0.672 | 0.650 | 0.752 | 0.620 | 0.608 | 0.679 |
| Ch CEL7 (SEQ ID NO: 24) | 0.595 | 0.597 | 0.600 | 0.597 | 0.595 | 0.595 | 0.659 | 0.670 | 0.651 | 0.632 | 0.643 | 0.626 | 0.619 | 0.621 | 0.606 | 0.638 | 0.621 | 0.598 |
| Ab Cel3A (SEQ ID NO: 25) | 0.580 | 0.582 | 0.582 | 0.582 | 0.579 | 0.576 | 0.584 | 0.579 | 0.564 | 0.557 | 0.583 | 0.570 | 0.543 | 0.546 | 0.542 | 0.569 | 0.541 | 0.538 |
| Pa Cel2 (SEQ ID NO: 26) | 0.571 | 0.573 | 0.573 | 0.570 | 0.567 | 0.575 | 0.567 | 0.572 | 0.571 | 0.553 | 0.579 | 0.591 | 0.506 | 0.512 | 0.563 | 0.554 | 0.537 | 0.528 |
| Le Cel6B (SEQ ID NO: 27) | 0.568 | 0.570 | 0.570 | 0.567 | 0.564 | 0.573 | 0.594 | 0.586 | 0.580 | 0.561 | 0.615 | 0.593 | 0.512 | 0.517 | 0.543 | 0.560 | 0.548 | 0.537 |
| Le CbhII-1 (SEQ ID NO: 28) | 0.565 | 0.567 | 0.567 | 0.564 | 0.561 | 0.570 | 0.591 | 0.583 | 0.574 | 0.559 | 0.612 | 0.591 | 0.509 | 0.515 | 0.543 | 0.557 | 0.545 | 0.534 |
| Mc Unnamed (SEQ ID NO: 29) | 0.548 | 0.550 | 0.553 | 0.550 | 0.547 | 0.550 | 0.597 | 0.608 | 0.602 | 0.586 | 0.574 | 0.610 | 0.570 | 0.592 | 0.631 | 0.596 | 0.583 | 0.572 |
| Pc CbhII (SEQ ID NO: 30) | 0.549 | 0.550 | 0.553 | 0.548 | 0.545 | 0.550 | 0.539 | 0.556 | 0.535 | 0.517 | 0.571 | 0.558 | 0.504 | 0.501 | 0.516 | 0.541 | 0.498 | 0.509 |
| Vv CbhI-I (SEQ ID NO: 31) | 0.540 | 0.542 | 0.542 | 0.548 | 0.545 | 0.542 | 0.567 | 0.572 | 0.563 | 0.553 | 0.582 | 0.582 | 0.531 | 0.531 | 0.546 | 0.554 | 0.537 | 0.537 |
| Cl Cel6A (SEQ ID NO: 32) | 0.494 | 0.498 | 0.498 | 0.495 | 0.493 | 0.495 | 0.510 | 0.510 | 0.534 | 0.519 | 0.506 | 0.501 | 0.512 | 0.509 | 0.490 | 0.498 | 0.497 | 0.482 |
| Psc CbhII (SEQ ID NO: 33) | 0.474 | 0.475 | 0.475 | 0.473 | 0.470 | 0.478 | 0.492 | 0.497 | 0.491 | 0.480 | 0.508 | 0.489 | 0.456 | 0.451 | 0.474 | 0.498 | 0.463 | 0.453 |
| Tv ORF (SEQ ID NO: 34) | 0.469 | 0.471 | 0.473 | 0.471 | 0.468 | 0.471 | 0.509 | 0.536 | 0.530 | 0.504 | 0.516 | 0.522 | 0.446 | 0.452 | 0.489 | 0.513 | 0.493 | 0.462 |
| Nc NCU03996.1 (SEQ ID NO: 35) | 0.467 | 0.468 | 0.471 | 0.465 | 0.463 | 0.471 | 0.478 | 0.483 | 0.498 | 0.480 | 0.501 | 0.468 | 0.468 | 0.468 | 0.485 | 0.471 | 0.461 | 0.465 |
| Mg MG04499.4 (SEQ ID NO: 36) | 0.451 | 0.452 | 0.455 | 0.446 | 0.444 | 0.452 | 0.467 | 0.472 | 0.476 | 0.467 | 0.476 | 0.465 | 0.463 | 0.457 | 0.482 | 0.455 | 0.459 | 0.457 |

FIGURE 9

| | Cl Unnamed (SEQ ID NO: 19) | Cl Cbh2 (SEQ ID NO: 20) | Sa Unnamed (SEQ ID NO: 21) | Hi Avi2 (SEQ ID NO: 22) | Hi Cel6A (SEQ ID NO: 23) | Ch CEL7 (SEQ ID NO: 24) | Ab Cel3A (SEQ ID NO: 25) | Pa Cel2 (SEQ ID NO: 26) | Le Cel6B (SEQ ID NO: 27) | Le CbhII-1 (SEQ ID NO: 28) | Mc Unnamed (SEQ ID NO: 29) | Pc CbhII (SEQ ID NO: 30) | Vv CbhII-I (SEQ ID NO: 31) | Cl Cel6A (SEQ ID NO: 32) | Psc CbhII (SEQ ID NO: 33) | Tv ORF (SEQ ID NO: 34) | Nc NCU03996.1 (SEQ ID NO: 35) | Mg MG04499.4 (SEQ ID NO: 36) |
|---|---|---|---|---|---|---|---|---|---|---|---|---|---|---|---|---|---|---|
| Tr Cel6A (SEQ ID NO: 1) | 0.651 | 0.650 | 0.648 | 0.636 | 0.631 | 0.595 | 0.580 | 0.571 | 0.568 | 0.565 | 0.548 | 0.549 | 0.540 | 0.494 | 0.474 | 0.469 | 0.467 | 0.451 |
| Hk Cbh2 (SEQ ID NO: 2) | 0.653 | 0.653 | 0.651 | 0.639 | 0.633 | 0.597 | 0.582 | 0.573 | 0.570 | 0.567 | 0.550 | 0.550 | 0.542 | 0.498 | 0.475 | 0.471 | 0.468 | 0.452 |
| Tv Cbh2 (SEQ ID NO: 3) | 0.656 | 0.655 | 0.653 | 0.642 | 0.636 | 0.600 | 0.582 | 0.573 | 0.570 | 0.567 | 0.553 | 0.553 | 0.542 | 0.498 | 0.475 | 0.473 | 0.471 | 0.455 |
| Hk Cbh2 (SEQ ID NO: 4) | 0.651 | 0.650 | 0.653 | 0.636 | 0.631 | 0.597 | 0.582 | 0.570 | 0.567 | 0.564 | 0.550 | 0.548 | 0.548 | 0.495 | 0.473 | 0.471 | 0.465 | 0.446 |
| Hk Cbh2 (SEQ ID NO: 5) | 0.648 | 0.647 | 0.651 | 0.633 | 0.628 | 0.595 | 0.579 | 0.567 | 0.564 | 0.561 | 0.547 | 0.545 | 0.545 | 0.493 | 0.470 | 0.468 | 0.463 | 0.444 |
| Tp CbhII (SEQ ID NO: 6) | 0.653 | 0.653 | 0.656 | 0.636 | 0.631 | 0.595 | 0.576 | 0.575 | 0.573 | 0.570 | 0.550 | 0.550 | 0.542 | 0.495 | 0.478 | 0.471 | 0.471 | 0.452 |
| An AN5282.2 (SEQ ID NO: 7) | 0.692 | 0.691 | 0.625 | 0.658 | 0.644 | 0.659 | 0.584 | 0.567 | 0.594 | 0.591 | 0.597 | 0.539 | 0.567 | 0.510 | 0.492 | 0.509 | 0.478 | 0.467 |
| An An12g02220 (SEQ ID NO: 8) | 0.702 | 0.702 | 0.620 | 0.669 | 0.653 | 0.670 | 0.579 | 0.572 | 0.586 | 0.583 | 0.608 | 0.556 | 0.572 | 0.510 | 0.497 | 0.536 | 0.483 | 0.472 |
| Ao AO090038000439 (SEQ ID NO: 9) | 0.687 | 0.681 | 0.618 | 0.634 | 0.620 | 0.651 | 0.564 | 0.571 | 0.580 | 0.574 | 0.602 | 0.535 | 0.563 | 0.534 | 0.491 | 0.530 | 0.498 | 0.476 |
| An An08g01760 (SEQ ID NO: 10) | 0.680 | 0.673 | 0.605 | 0.632 | 0.613 | 0.632 | 0.557 | 0.553 | 0.561 | 0.559 | 0.586 | 0.517 | 0.553 | 0.519 | 0.480 | 0.504 | 0.480 | 0.467 |
| Ac Acc2 (SEQ ID NO: 11) | 0.681 | 0.674 | 0.603 | 0.639 | 0.625 | 0.643 | 0.583 | 0.579 | 0.615 | 0.612 | 0.574 | 0.571 | 0.582 | 0.506 | 0.508 | 0.516 | 0.501 | 0.476 |
| Te CbhII (SEQ ID NO: 12) | 0.676 | 0.675 | 0.601 | 0.645 | 0.631 | 0.626 | 0.570 | 0.591 | 0.593 | 0.591 | 0.610 | 0.558 | 0.582 | 0.501 | 0.489 | 0.522 | 0.468 | 0.465 |
| Gz Cel6 (SEQ ID NO: 13) | 0.677 | 0.676 | 0.671 | 0.674 | 0.672 | 0.619 | 0.543 | 0.506 | 0.512 | 0.509 | 0.570 | 0.504 | 0.531 | 0.512 | 0.456 | 0.446 | 0.468 | 0.463 |
| Fo EglB (SEQ ID NO: 14) | 0.672 | 0.671 | 0.657 | 0.658 | 0.650 | 0.621 | 0.546 | 0.512 | 0.517 | 0.515 | 0.592 | 0.501 | 0.531 | 0.509 | 0.451 | 0.452 | 0.468 | 0.457 |
| Nc NCU09680.1 (SEQ ID NO: 15) | 0.763 | 0.763 | 0.707 | 0.771 | 0.752 | 0.606 | 0.542 | 0.563 | 0.543 | 0.543 | 0.631 | 0.516 | 0.546 | 0.490 | 0.474 | 0.489 | 0.485 | 0.482 |
| An AN1273.2 (SEQ ID NO: 16) | 0.681 | 0.674 | 0.614 | 0.631 | 0.620 | 0.638 | 0.569 | 0.554 | 0.560 | 0.557 | 0.596 | 0.541 | 0.554 | 0.498 | 0.498 | 0.513 | 0.471 | 0.455 |
| At Unnamed (SEQ ID NO: 17) | 0.669 | 0.663 | 0.597 | 0.627 | 0.608 | 0.621 | 0.541 | 0.537 | 0.548 | 0.545 | 0.583 | 0.498 | 0.537 | 0.497 | 0.463 | 0.493 | 0.461 | 0.459 |
| Mg MG05520.4 (SEQ ID NO: 18) | 0.677 | 0.671 | 0.636 | 0.684 | 0.679 | 0.598 | 0.538 | 0.528 | 0.537 | 0.534 | 0.572 | 0.509 | 0.537 | 0.482 | 0.453 | 0.462 | 0.465 | 0.457 |
| Cl Unnamed (SEQ ID NO: 19) | ID | 0.989 | 0.700 | 0.838 | 0.808 | 0.629 | 0.571 | 0.567 | 0.547 | 0.547 | 0.610 | 0.545 | 0.578 | 0.505 | 0.487 | 0.520 | 0.483 | 0.483 |
| Cl Cbh2 (SEQ ID NO: 20) | 0.989 | ID | 0.699 | 0.837 | 0.807 | 0.622 | 0.564 | 0.563 | 0.543 | 0.543 | 0.612 | 0.541 | 0.571 | 0.504 | 0.481 | 0.513 | 0.482 | 0.482 |
| Sa Unnamed (SEQ ID NO: 21) | 0.700 | 0.699 | ID | 0.703 | 0.686 | 0.607 | 0.532 | 0.542 | 0.537 | 0.534 | 0.601 | 0.528 | 0.539 | 0.487 | 0.461 | 0.468 | 0.471 | 0.476 |
| Hi Avi2 (SEQ ID NO: 22) | 0.838 | 0.837 | 0.703 | ID | 0.961 | 0.609 | 0.547 | 0.552 | 0.543 | 0.543 | 0.636 | 0.535 | 0.563 | 0.490 | 0.479 | 0.500 | 0.463 | 0.466 |
| Hi Cel6A (SEQ ID NO: 23) | 0.808 | 0.807 | 0.686 | 0.961 | ID | 0.601 | 0.544 | 0.543 | 0.530 | 0.530 | 0.628 | 0.527 | 0.549 | 0.482 | 0.474 | 0.489 | 0.457 | 0.460 |
| Ch CEL7 (SEQ ID NO: 24) | 0.629 | 0.622 | 0.607 | 0.609 | 0.601 | ID | 0.593 | 0.570 | 0.570 | 0.567 | 0.594 | 0.528 | 0.559 | 0.527 | 0.495 | 0.531 | 0.486 | 0.502 |
| Ab Cel3A (SEQ ID NO: 25) | 0.571 | 0.564 | 0.532 | 0.547 | 0.544 | 0.593 | ID | 0.720 | 0.720 | 0.717 | 0.532 | 0.717 | 0.742 | 0.494 | 0.643 | 0.645 | 0.483 | 0.467 |
| Pa Cel2 (SEQ ID NO: 26) | 0.567 | 0.563 | 0.542 | 0.552 | 0.543 | 0.570 | 0.720 | ID | 0.750 | 0.747 | 0.545 | 0.794 | 0.750 | 0.473 | 0.599 | 0.772 | 0.471 | 0.460 |
| Le Cel6B (SEQ ID NO: 27) | 0.547 | 0.543 | 0.537 | 0.543 | 0.530 | 0.570 | 0.720 | 0.750 | ID | 0.991 | 0.545 | 0.755 | 0.780 | 0.463 | 0.635 | 0.677 | 0.457 | 0.443 |
| Le CbhII-1 (SEQ ID NO: 28) | 0.547 | 0.543 | 0.534 | 0.543 | 0.530 | 0.567 | 0.717 | 0.747 | 0.991 | ID | 0.542 | 0.755 | 0.772 | 0.460 | 0.635 | 0.677 | 0.454 | 0.441 |
| Mc Unnamed (SEQ ID NO: 29) | 0.610 | 0.612 | 0.601 | 0.636 | 0.628 | 0.594 | 0.532 | 0.545 | 0.545 | 0.542 | ID | 0.528 | 0.547 | 0.470 | 0.485 | 0.515 | 0.445 | 0.478 |
| Pc CbhII (SEQ ID NO: 30) | 0.545 | 0.541 | 0.528 | 0.535 | 0.527 | 0.528 | 0.717 | 0.794 | 0.755 | 0.755 | 0.528 | ID | 0.738 | 0.449 | 0.603 | 0.697 | 0.449 | 0.419 |
| Vv CbhII-I (SEQ ID NO: 31) | 0.578 | 0.571 | 0.539 | 0.563 | 0.549 | 0.559 | 0.742 | 0.750 | 0.780 | 0.772 | 0.547 | 0.738 | ID | 0.471 | 0.640 | 0.663 | 0.476 | 0.482 |
| Cl Cel6A (SEQ ID NO: 32) | 0.505 | 0.504 | 0.487 | 0.490 | 0.482 | 0.527 | 0.494 | 0.473 | 0.463 | 0.460 | 0.470 | 0.449 | 0.471 | ID | 0.410 | 0.435 | 0.825 | 0.775 |
| Psc CbhII (SEQ ID NO: 33) | 0.487 | 0.481 | 0.461 | 0.479 | 0.474 | 0.495 | 0.643 | 0.599 | 0.635 | 0.635 | 0.485 | 0.603 | 0.640 | 0.410 | ID | 0.550 | 0.415 | 0.405 |
| Tv ORF (SEQ ID NO: 34) | 0.520 | 0.513 | 0.468 | 0.500 | 0.489 | 0.531 | 0.645 | 0.772 | 0.677 | 0.677 | 0.515 | 0.697 | 0.663 | 0.435 | 0.550 | ID | 0.441 | 0.413 |
| Nc NCU03996.1 (SEQ ID NO: 35) | 0.483 | 0.482 | 0.471 | 0.463 | 0.457 | 0.486 | 0.483 | 0.471 | 0.457 | 0.454 | 0.445 | 0.449 | 0.476 | 0.825 | 0.415 | 0.441 | ID | 0.780 |
| Mg MG04499.4 (SEQ ID NO: 36) | 0.483 | 0.482 | 0.476 | 0.466 | 0.460 | 0.502 | 0.467 | 0.460 | 0.443 | 0.441 | 0.478 | 0.419 | 0.482 | 0.775 | 0.405 | 0.413 | 0.780 | ID |

FAMILY 6 CELLULASE WITH DECREASED INACTIVATION BY LIGNIN

FIELD OF THE INVENTION

The present invention relates to modified Family 6 cellulases. More specifically, the invention relates to modified *Trichoderma reesei* Family 6 (TrCel6A) cellulases with decreased inactivation by lignin. The present invention also relates to genetic constructs comprising nucleotide sequences encoding for modified TrCel6A cellulases, methods for the production of the modified TrCel6A cellulase from host strains and the use of the modified TrCel6A cellulases in the hydrolysis of lignocellulosic substrates.

BACKGROUND OF THE INVENTION

More than half of organic carbon on earth is found in the cell walls of plants. Plant cell walls comprise three main compounds: cellulose, hemicellulose, and lignin. Collectively these compounds are called "lignocellulose," and they represent a potential source of sugars and other organic molecules for fermentation to ethanol or other high-value products.

The conversion of lignocellulosic biomass to ethanol has become a key feature of emerging energy policies due to the environmentally favorable and sustainable nature of cellulosic ethanol. There are several technologies being developed for cellulose conversion. Of interest here is a method by which lignocellulosic biomass is subjected to a pretreatment that increases its susceptibility to hydrolytic enzymes, followed by enzymatic hydrolysis to sugars and the fermentation of those sugars to ethanol or other high-value organic molecules (e.g. butanol). Common pretreatment methods include dilute acid steam explosion (U.S. Pat. No. 4,461,648), ammonia freeze explosion (AFEX; Holtzapple et al., 1991), and organosolv extraction (U.S. Pat. No. 4,409,032). Hydrolysis and fermentation systems may be either separate (sequential hydrolysis and fermentation; SHF) or coincident (simultaneous saccharification and fermentation; SSF). In all instances, the hemicellulose and cellulose are broken down to sugars that may be fermented, while the lignin becomes separated and may be used either as a solid fuel or as a source for other organic molecules.

The choice of enzymes for conversion of pretreated lignocellulosic biomass to sugars is highly dependent upon the pretreatment method. Dilute acid steam explosion results in significant chemical hydrolysis of the hemicellulose, thereby making enzymes for the conversion of hemicellulose to sugars less relevant to the process. In contrast, AFEX and organosolv extraction both leave hemicellulose and cellulose largely intact. Organosolv extraction, unlike dilute acid steam explosion or AFEX removes a significant portion of the lignin from substrate. In all instances, the primary target for enzymatic hydrolysis is the cellulose, which is converted to sugars using a combination of cellulase enzymes.

There are two principle types of cellulase enzymes: endoglucanases, which cleave glycosidic bonds in the middle of cellulose chains, and in doing so, create new chain ends, and cellobiohydrolases, which cleave short oligosaccharides from the ends of cellulose chains. Glucosidases digest short oligosaccharides into monosaccharides. These three enzyme components thus act synergistically to create an efficient cellulolytic enzyme system. Most cellulases have a similar modular structure, which consists of a catalytic domain, linker peptide and a carbohydrate-binding module (CBM).

Modified cellulase enzymes and methods for modification have been extensively described. For example, variants of *Trichoderma reesei* Cel7A and Cel6A to improve thermostability have been reported (U.S. Pat. No. 7,375,197; WO 2005/028636; U.S. Publication No. 2007/0173431; U.S. Publication No. 2008/167214; WO 2006/074005; U.S. Publication No. 2006/0205042; U.S. Pat. No. 7,348,168; WO 2008/025164). In particular, substitution of the serine at position 413 in *T. reesei* Cel6A with a proline, or substitution of the amino acid at the equivalent to position 413 with a proline in other Family 6 cellulases confers increased thermostability (WO 2008/025164). Mutations at the equivalent of positions 103, 136, 186, 365 and 410 within the catalytic domain of *T. reesei* Cel6A and other Family 6 cellulases have been shown to lead to reduced inhibition by glucose (U.S. Patent Publication No: 2009/0186381). Variants with resistance to proteases and to surfactants for detergent formulations have been created for textile applications (WO 99/01544; WO 94/07998; and U.S. Pat. No. 6,114,296).

The negative effects of lignin on cellulase enzyme systems are well documented. Removal of lignin from hardwood (aspen) was shown to increase sugar yield by enzymatic hydrolysis (Kong et al., 1992). Similarly, removal of lignin from softwood (Douglas fir) was shown to improve enzymatic hydrolysis of the cellulose, an effect attributed to improved accessibility of the enzymes to the cellulose (Mooney et al., 1998). Other groups have demonstrated that cellulases purified from *Trichoderma reesei* bind to isolated lignin (Chemoglazov et al., 1988) and have speculated on the role of the different binding domains in the enzyme-lignin interaction (Palonen et al., 2004). Binding to lignin and inactivation of *Trichoderma reesei* cellulases has been observed when lignin is added back to a pure cellulose system (Escoffier et al., 1991). Only in one instance was lignin reported to not have any significant effect on cellulases (Meunier-Goddik and Penner, 1999). Other reports suggest that some hemicellulases may be resistant to, and even activated by, lignin and lignin breakdown products (Kaya et al., 2000). Thus, it is generally recognized that lignin is a serious limitation to enzymatic hydrolysis of cellulose.

CBMs are reportedly involved in lignin binding. For example, removal of the CBM from *Trichoderma* Cel7A essentially eliminates binding to alkali extracted lignin and to residual lignin prepared by enzyme hydrolysis (Palonen et al., 2004).

Catalytic domains are also reportedly involved in binding lignin. Cel7B from *Humicola* sp., which does not possess a CBM, is bound extensively by lignin (Berlin et al., 2005b). Similarly *Trichoderma* Cel5A core, devoid of a CBM, does not bind enzymic lignin and binds alkali extracted lignin to a lesser extent than does the full-length protein (Palonen et al., 2004).

The development of lignin resistant cellulases with preserved cellulose binding affinity and native cellulolytic activity represents a large hurdle in the commercialization of cellulose conversion to soluble sugars including glucose for the production of ethanol and other products. A variety of methods have been suggested to reduce the negative impact of lignin on the cellulase system. Non-specific binding proteins (e.g. bovine serum albumin; BSA) have been shown to block interactions between cellulases and lignin surfaces (Yang and Wyman, 2006; US24185542 A1; US26088922 A1; WO05024037 A2, A3; WO09429474 A1). Other chemical blocking agents and surfactants have been shown to have a similar effect (Tu et al., 2007; U.S. Pat. No. 7,354,743). While it has been proposed to seek out and identify lignin-resistant variants of cellulase enzymes (Berlin et al., 2005a), no successful work in this direction has been previously documented.

SUMMARY OF THE INVENTION

The present invention relates to modified cellulase enzymes. More specifically, the present invention relates to modified *Trichoderma reesei* Family 6 (TrCel6A) cellulases with decreased inactivation by lignin. The present invention also relates to genetic constructs comprising nucleotide sequences encoding for modified TrCel6A cellulases, methods for the production of the modified TrCel6A cellulase from host strains and the use of the modified TrCel6A cellulases in the hydrolysis of lignocellulosic substrates.

It is an object of the invention to provide a modified TrCel6A cellulase with decreased inactivation by lignin.

The present invention relates to a modified TrCel6A cellulase comprising one or more amino acid substitutions selected from the group consisting of:
substitution of a basic amino acid at one or more of positions 129 and 410 by a charge-neutral or an acidic amino acid;
substitution of a charge-neutral amino acid at one or more of positions 322 and 363 by an acidic amino acid; and
substitution of an amino acid at position 186 by a threonine; the modified TrCel6A cellulase having an amino acid sequence that exhibits from about 47% to about 99.9% identity to amino acid 83-447 of SEQ ID NO: 1. Furthermore, the modified TrCel6A cellulase may comprise one or more amino acid substitutions selected from the group consisting of K129E, S186T, A322D, Q363E, R410G, and R410Q. The modified TrCel6A cellulase is capable of hydrolyzing polysaccharides using an inverting mechanism.

The position of the one or more amino acid substitution defined above may be determined from sequence alignment of the amino acids corresponding to amino acids 83-447 of SEQ ID NO: 1 of a parental TrCel6A cellulase enzyme with amino acids 83-447 comprising the catalytic domain of the *Trichoderma reesei* Cel6A amino acid sequence as defined in SEQ ID NO: 1.

The modified TrCel6A cellulase may be derived from a parental TrCel6A cellulase that is otherwise identical to the modified TrCel6A cellulase except for the substitution of the naturally occurring amino acid at one or more of positions 129, 186, 322, 363, or 410. For example, this invention includes a modified TrCel6A cellulase as defined above further comprising one or more amino acid substitutions selected from the group consisting of Y103H, Y103K, Y103R, Y103A, Y103V, Y103L, Y103P, L136V, L136I, and S413P or any other additional mutations at positions other than 129, 186, 322, 363, or 410, provided that the enzyme exhibits Cel6A cellulase activity.

The present invention also relates to a modified TrCel6A cellulase, as defined above, that exhibits at least a 15% reduction in the extent of deactivation by lignin relative to that of a parental TrCel6A cellulase from which the modified TrCel6A cellulase is derived The present invention also relates to a modified Family 6 cellulase selected from the group consisting of:
TrCel6A-K129E-S413P (SEQ ID NO: 37);
TrCel6A-S186T-S413P (SEQ ID NO: 38);
TrCel6A-A322D-S413P (SEQ ID NO: 39);
TrCel6A-Q363E-S413P (SEQ ID NO: 40);
TrCel6A-R410G-S413P (SEQ ID NO: 41);
TrCel6A-R410Q-S413P (SEQ ID NO: 42);
TrCel6A-K129E-S186T-A322D-Q363E-S413P (SEQ ID NO: 43); and
TrCel6A-K129E-S186T-A322D-Q363E-R410Q-S413P (SEQ ID NO: 44).

The present invention relates to genetic constructs comprising a nucleic acid sequence encoding a modified TrCel6A cellulase comprising one or more amino acid substitutions selected from the group consisting of:
substitution of a basic amino acid at one or more of positions 129 and 410 by a charge-neutral or an acidic amino acid;
substitution of a charge-neutral amino acid at one or more of positions 322 and 363 by an acidic amino acid; and
substitution of an amino acid at position 186 by a threonine, the modified TrCel6A cellulase having an amino acid sequence that exhibits from 47% to 99.9% identity to amino acids 83-447 of SEQ ID NO: 1. The nucleic acid sequence may be operably linked to other nucleic acid sequences regulating its expression and secretion from a host microbe. The other nucleic sequences regulating the expression and secretion of the modified TrCel6A cellulase may be derived from the host microbe used for expression of the modified TrCel6A cellulase. The host microbe may be a yeast, such as *Saccharomyces cerevisiae*, or a filamentous fungus, such as *Trichoderma reesei*.

The invention also relates to a genetic construct as defined above, wherein the modified TrCel6A cellulase encoded by the genetic construct further comprises one or more amino acid substitutions selected from the group consisting of Y103H, Y103K, Y103R, Y103A, Y103V, Y103L, Y103P, L136V, L136I, and S413P, or any other additional mutations at positions other than 129, 186, 322, 363 or 410, provided that the enzyme exhibits Cel6A cellulase activity.

The invention also relates to a genetically modified microbe comprising a genetic construct encoding a modified TrCel6A cellulase and capable of expression and secretion of a modified TrCel6A cellulase comprising one or more amino acid substitutions selected from the group consisting of:
substitution of a basic amino acid at one or more of positions 129 and 410 by a charge-neutral or an acidic amino acid;
substitution of a charge-neutral amino acid at one or more of positions 322 and 363 by an acidic amino acid; and
substitution of an amino acid at position 186 by a threonine, the modified TrCel6A cellulase having an amino acid sequence that exhibits 47% to 99.9% identity to amino acids 83-447 of SEQ ID NO: 1. In one embodiment, the genetically modified microbe is capable of expression and secretion of a modified TrCel6A cellulase further comprising one or more amino acid substitutions selected from the group consisting of Y103H, Y103K, Y103R, Y103A, Y103V, Y103L, Y103P, L136V, L136I, and S413P, or any other additional mutations at positions other than 129, 186, 322, 363, or 410. The genetically modified microbe may be a yeast or filamentous fungus. For example, the genetically modified microbe may be a species of *Saccharomyces, Pichia, Hansenula, Trichoderma, Hypocrea, Aspergillus, Fusarium, Humicola* or *Neurospora*.

The present invention also relates to a process for hydrolysing cellulose in the presence of lignin with a modified TrCel6A cellulase.

The invention also relates to a process of producing a modified TrCel6A cellulase as defined above, including transformation of a yeast or fungal host with a genetic construct comprising a DNA sequence encoding a modified TrCel6A cellulase, selection of recombinant yeast or fungal strains expressing a modified TrCel6A cellulase, culturing the selected recombinant strains in submerged liquid fermentations under conditions that induce the expression of a modified TrCel6A cellulase and recovering the modified TrCel6A cellulase thus produced by separation of the culture filtrate from the host microbe.

The inventors have made the discovery that substitution of a basic or charge-neutral amino acid at position 129, 322, 363 or 410 or of the amino acid at position 186 by a threonine, results in a decrease in the extent of deactivation of the modified TrCel6A cellulase by lignin relative to that of a parental TrCel6A cellulase from which it is derived. As shown in FIG. 8, all of these amino acids are located on the surface of the TrCel6A cellulase.

Modified TrCel6A cellulases of the present invention can exhibit at least a 15% reduction in the extent of deactivation by lignin relative to that of a parental TrCel6A cellulase from which the modified TrCel6A cellulase is derived. This decreased lignin inactivation contributes to increased activity for the hydrolysis of a cellulose substrate in a hydrolysis reaction containing the modified TrCel6A cellulase, cellulose and lignin relative to the parental TrCel6A cellulase from which the modified TrCel6A cellulase is derived.

Such TrCel6A cellulases find use in a variety of applications in industry that require high cellulose-hydrolyzing activity in the presence of lignin. For example, modified TrCel6A cellulase, as described herein, may be used in industrial processes in which lignocellulosic substrates are converted to fermentable sugars used for the production of fuel alcohols, sugar alcohols or other products.

DESCRIPTION OF THE DRAWINGS

These and other features of the invention will become more apparent from the following description in which reference is made to the appended drawings wherein:

FIG. 1 shows an amino acid sequence alignment among selected fungal cellulases from Glycosyl Hydrolase Family 6 and a consensus Family 6 cellulase sequence. A graphical representation of the frequency of occurrence of the amino acid at each position of the consensus Family 6 cellulase among the 36 fungal Family 6 cellulases is shown below the aligned sequences. The catalytic aspartic acid residues at the equivalent positions 175 and 221 in TrCel6A are indicated by arrows. The highly conserved amino acids at the equivalent of positions 129, 186, 363, 322, and 410 in TrCel6A are indicated with an asterisk. For cellulases with a cellulose-binding domain, only the catalytic core sequences are presented.

FIG. 3 contains two scatter plots. Panel A is a scatter plot of enzyme activity in the presence of BSA-treated lignin (+BSA) versus enzyme activity in the presence of untreated lignin (−BSA) for high-throughput assay 1 (Example 6). The data relate to the screening of one 96-well culture plate containing parental (TrCel6A-S413P) and modified TrCel6A cellulases or filtrates from empty vector transformants (Negative Controls). Panel B is a scatter plot of enzyme activity in the presence of BSA-treated lignin (+BSA) versus enzyme activity in the presence of untreated lignin (−BSA) for high-throughput assay 2 (Example 7). The data relate to the screening of one 96-well culture plate containing parental (TrCel6A-S413P) and modified TrCel6A cellulases or filtrates from empty vector transformants (Negative Controls).

FIG. 5 contains two scatter plots. Panel A is a scatter plot of enzyme activity in the presence of BSA-treated lignin (+BSA) versus enzyme activity in the presence of untreated lignin (−BSA) for high-throughput assay 1 (Example 6). The data relate to the screening of the modified cellulase TrCel6A-K129E-S186T-A322D-Q363E-S413P and the parental cellulase TrCel6A-S413P. Panel B is a scatter plot of enzyme activity in the presence of BSA-treated lignin (+BSA) versus enzyme activity in the presence of untreated lignin (−BSA) for high-throughput assay 2 (Example 7). The data relate to the screening of the modified cellulases TrCel6A-K129E-S 186T-A322D-Q363E-S413P, TrCel6A-K129E-S186T-A322D-Q363E-R410Q-S413P and the parental cellulase TrCel6A-S413P.

FIG. 9 shows an identity matrix for the alignment of the amino acids corresponding to amino acids 83-447 of SEQ ID NO: 1 for each of 36 Family 6 cellulase amino acid sequences to each other.

DESCRIPTION OF PREFERRED EMBODIMENT

Figure 2:
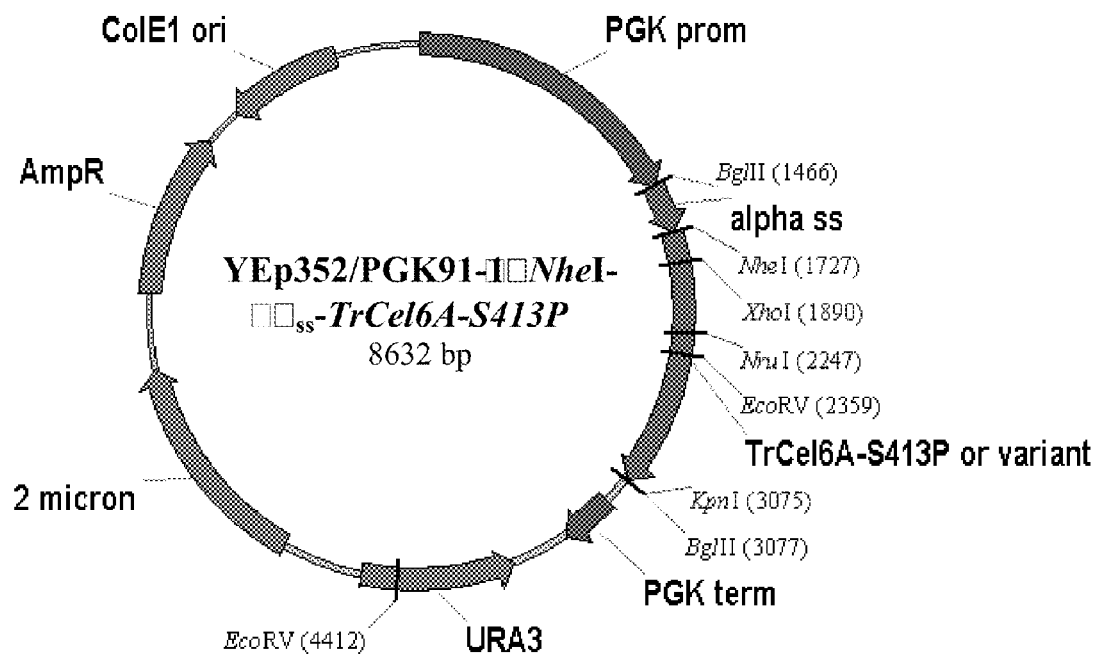
FIG. 2 depicts plasmid vector YEp352/PGK91-1ΔNheI-$\alpha_{ss}$-TrCel6A-S413P directing the expression and secretion of native and modified TrCel6A from recombinant *Saccharomyces cerevisiae*.

The present invention relates to modified cellulases. More specifically, the invention relates to modified *Trichoderma reesei* Family 6 (TrCel6A) cellulases with decreased inactivation by lignin. The present invention also relates to genetic constructs comprising nucleic acid sequences encoding for modified TrCel6A cellulases, methods for the production of the modified TrCel6A cellulase from host strains and the use of the modified TrCel6A cellulase in the hydrolysis of cellulose in the presence of lignin.

The present invention provides a modified TrCel6A cellulase with decreased inactivation by lignin and thus, increased cellulose hydrolyzing activity in a hydrolysis reaction comprising the modified TrCel6A cellulase, cellulose and lignin, relative to the cellulose-hydrolyzing activity of a parental TrCel6A cellulase from which the modified TrCel6A cellulase is derived, in a hydrolysis reaction of equivalent composition.

The following description is of a preferred embodiment by way of example only and without limitation to the combination of features necessary for carrying the invention into effect.

Modified TrCel6A Cellulases

A cellulase enzyme is classified as a Family 6 cellulase if it exhibits similarity in its primary, secondary and tertiary protein structures relative to those of other Family 6 cellulases. For example, all Family 6 cellulases comprise two aspartic acid (D) residues which may serve as catalytic residues. These aspartic acid residues are found at positions 175 and 221 (see FIG. 1; based on TrCel6A, *Trichoderma reesei* Cel6A, amino acid numbering). Most of the Family 6 cellulases identified thus far are mesophilic; however, this family also includes thermostable cellulases from *Thermobifida fusca* (TfCel6A and TfCel6B) and the alkalophilic cellulases from *Humicola insolens* (HiCel6A and HiCel6B). Family 6 cellulases also share a similar three dimensional structure: an alpha/beta-barrel with a central beta-barrel containing seven parallel beta-strands connected by five alpha-helices. The three dimensional structures of several Family 6 cellulases are known, such as TrCel6A (Rouvinen, J., et al. 1990), *Thermobifida fusca* endo-beta-1,4-glucanase Cel6A (TfCel6A, Spezio, M., et al. 1993), *Humicola insolens* cellobiohydrolase Cel6A (HiCel6A, Varrot, A., et al. 1999), *Humicola insolens* endo-beta-1,4-glucanase Cel6B (HiCel6B, Davies, G. J., et al. 2000) and *Mycobacterium tuberculosis* H37Rv Cel6A (MtCel6A, Varrot, A., et al. 2005).

amino acid sequence identity to TrCel6A or to other Family 6 cellulases of fungal origin. TrCel6A is a member of glycoside hydrolase Family 6, which comprises enzymes that hydrolyses b-1,4 glycosidic bonds with inversion of anomeric configuration, referred to herein as an "inverting mechanism". Family 6 glycoside hydrolases are defined by the CAZy system which is accepted as a standard nomenclature for such enzymes (see URL: cazy.org).

By "TrCel6A numbering", it is meant the numbering corresponding to the position of amino acids based on the amino acid sequence of TrCel6A (SEQ ID NO: 1). As set forth below, and as is evident by FIG. 1, Family 6 cellulases exhibit a substantial degree of sequence similarity. Therefore, by aligning the amino acids to optimize the sequence similarity between the Family 6 catalytic domains of cellulase enzymes, and by using the amino acid numbering of TrCel6A as the basis for numbering, the positions of amino acids within other Family 6 cellulases can be determined relative to TrCel6A.

TABLE 1

% Amino Acid Sequence Identity of Fungal Family 6 Cellulases to TrCel6A

| SEQ ID | Organism | Protein | Identity with TrCel6A catalytic domain (83-447) (%) |
|---|---|---|---|
| 2 | *Hypocrea koningii* | cellobiohydrolase II (Cbh2) | 98.9 |
| 3 | *Trichoderma viride* CICC 13038 | cellobiohydrolase II (CbhII; Cbh2) | 98.9 |
| 4 | *Hypocrea koningii* 3.2774 | cellobiohydrolase II (Cbh2; CbhII) | 98.1 |
| 5 | *Hypocrea koningii* AS3.2774 | cbh2 | 97.8 |
| 6 | *Trichoderma parceramosum* | cellobiohydrolase II (CbhII) | 97.8 |
| 7 | *Aspergillus nidulans* FGSC A4 | cellobiohydrolase (AN5282.2) | 72.4 |
| 8 | *Aspergillus niger* CBS 513.88 | An12g02220 | 72.4 |
| 9 | *Aspergillus oryzae* RIB 40 | AO090038000439 | 67.8 |
| 10 | *Aspergillus niger* CBS 513.88 | An08g01760 | 67.7 |
| 11 | *Acremonium cellulolyticus* Y-94 | cellobiohydrolase II (Acc2) | 67.3 |
| 12 | *Talaromyces emersonii* | cellobiohydrolase II (CbhII) | 66.8 |
| 13 | *Gibberella zeae* K59 | Cel6 - Cel6 | 66.1 |
| 14 | *Fusarium oxysporum* | endoglucanase B | 66.1 |
| 15 | *Neurospora crassa* OR74A | NCU09680.1 (64C2.180) | 65.9 |
| 16 | *Aspergillus nidulans* FGSC A4 | AN1273.2 | 65.5 |
| 17 | *Aspergillus tubingensis* | unnamed protein product (fragment) | 65.5 |
| 18 | *Magnaporthe grisea* 70-15 | MG05520.4 | 65.4 |
| 19 | *Chaetomium thermophilum* | unnamed protein product | 65.1 |
| 20 | *Chaetomium thermophilum* CT2 | cellobiohydrolase (Cbh2) | 65.0 |
| 21 | *Stilbella annulata* | unnamed protein product | 64.9 |
| 22 | *Humicola insolens* | avicelase2 (Avi2) | 63.7 |
| 23 | *Humicola insolens* | cellobiohydrolase (CBHII) - Cel6A | 63.1 |
| 24 | *Cochliobolus heterostrophus* C4 | cellobiohydrolase II (CEL7) | 59.6 |
| 25 | *Agaricus bisporus* D649 | cellobiohydrolase II (Cel3; Cel3A) | 57.7 |
| 26 | *Polyporus arcularius* 69B-8 | cellobiohydrolase II (Cel2) | 57.1 |
| 27 | *Lentinula edodes* Stamets CS-2 | cellulase - Cel6B | 56.3 |
| 28 | *Lentinula edodes* L54 | cellobiohydrolase (CbhII-1) | 56.0 |
| 29 | *Malbranchea cinnamomea* | unnamed protein product | 54.9 |
| 30 | *Phanerochaete chrysosporium* | cellobiohydrolase II | 54.9 |
| 31 | *Volvariella volvacea* | cellobiohydrolase II-I (CbhII-I) | 53.8 |
| 32 | *Chrysosporium lucknowense* | cellobiohydrolase (EG6; CBH II) - Cel6A | 49.5 |
| 33 | *Pleurotus sajor-caju* | cellobiohydrolase II | 47.2 |
| 34 | *Trametes versicolor* | ORF | 47.0 |
| 35 | *Neurospora crassa* OR74A | NCU03996.1 | 46.8 |
| 36 | *Magnaporthe grisea* 70-15 | MG04499.4 | 45.1 |

As shown in FIG. 1, there is a high degree of conservation of primary amino acid sequence among Family 6 cellulases. Multiple alignment across 36 currently known Family 6 cellulase amino acid sequences of fungal origin shows that most naturally occurring Family 6 cellulases exhibit from about 47% to about 100% amino acid sequence identity to amino acids 83-447 comprising the catalytic domain of TrCel6A (Table 1) and from about 70% to 100% amino acid sequence identity to at least one other Family 6 cellulase. Family 6 cellulases of bacterial origin show a much lower degree of Methods to align amino acid sequences are well known and available to those of skill in the art and include BLAST (Basic Local Alignment Search Tool, URL: blast.ncbi.nlm.nih.gove/Blast.chi; Altschul et al., 1990; using the published default settings) which is useful for aligning two sequences and CLUSTALW (URL: ebi.cak.ak/Tools/clustalw2/index.html) for alignment of two or more sequences.

By "modified TrCel6A cellulase" or "modified cellulase", it is meant a *Trichoderma reesei* Family 6 cellulase of SEQ ID NO: 1 which comprises one or more amino acid substitutions selected from the group consisting of:
substitution of a basic amino acid at one or more of positions 129 and 410 by a charge-neutral or an acidic amino acid;
substitution of a charge-neutral amino acid at one or more of positions 322 and 363 by an acidic amino acid; and
substitution of an amino acid at position 186 by a threonine.

For example, which is not to be considered limiting, the modified TrCel6A cellulase may comprise one or more amino acid substitutions selected from the group consisting of K129E, S186T, A322D, Q363E, R410G, and R410Q.

As defined herein, "basic amino acid" refers to any one of histidine, lysine or arginine, "acid amino acid" refers to any one of aspartic acid or glutamic acid and "charge-neutral amino acid" is any amino acid that is not a basic or acidic amino acid.

It will be understood that modified TrCel6A cellulase may be derived from a wild-type TrCel6A cellulase or from a TrCel6A cellulase that already contains other amino acid substitutions.

A "modified TrCel6A cellulase" may also be defined as an enzyme capable of hydrolyzing polysaccharides using an inverting mechanism and having one or more amino acid substitutions, introduced by genetic engineering techniques, selected from the group consisting of:
substitution of a basic amino acid at one or more of positions 129 and 410 by a charge-neutral or an acidic amino acid;
substitution of a charge-neutral amino acid at one or more of positions 322 and 363 by an acidic amino acid; and
substitution of an amino acid at position 186 by a threonine; and which is characterized by having an amino acid sequence that is from about 47% to about 99.9% identical to the amino acids 83 to 447 of the TrCel6A amino acid sequence (SEQ ID NO: 1). For example, a modified TrCel6A cellulase may have an amino acid sequence that is about 47%, 50%, 55%, 60%, 65%, 70%, 75%, 80%, 85%, 90%, 95% or 99.9% identical to the amino acids 83-447 of SEQ ID NO: 1. One of skill in the art will appreciate that the amino acid sequence of a given TrCel6A cellulase may be modified by the addition, deletion or substitution of one or more amino acids and still be considered a modified TrCel6A cellulase, given that the basic structure and function of the enzyme is retained.

The modified TrCel6A cellulase of the present invention is encoded by a nucleic acid sequence that can be generated using genetic material or nucleic acid or amino acid sequence information specific to the desired modified TrCel6A cellulase or to a corresponding parental TrCel6A cellulase. As is known by one of skill in the art, such material or sequence information can be used to generate a nucleic acid sequence encoding a desired modified TrCel6A cellulase using one or more molecular biology techniques for altering amino acid sequences including, but not limited to, site-directed mutagenesis, cassette mutagenesis, random mutagenesis, synthetic oligonucleotide construction, cloning, sub-cloning, amplification by PCT, in vitro synthesis and other genetic engineering techniques (Eijsink V G, et al. 2005). It will be understood that the modified TrCel6A cellulase may be derived from any TrCel6A cellulase—i.e., it may be derived from a naturally-occurring or "wild-type" TrCel6A cellulase or from a TrCel6A cellulase that already contains other amino acid substitutions.

In one embodiment of the invention, the modified TrCel6A cellulase comprises an amino acid sequence that is from about 70% to 99.9% identical to amino acids 83-447 of SEQ ID NO: 1, and exhibits at least a 15% reduction in the extent of deactivation of the modified TrCel6A cellulase by lignin relative to that of a parental TrCel6A cellulase from which the modified TrCel6A cellulase is derived. The modified TrCel6A cellulase is capable of hydrolyzing polysaccharides using an inverting mechanism.

In other embodiments of the invention, the modified TrCel6A cellulase comprises an amino acid sequence that is from about 90% to about 99.9% identical to amino acids 83-447 of SEQ ID NO: 1, and exhibits at least a 15% reduction in the extent of deactivation of the modified TrCel6A cellulase by lignin relative to that of a parental TrCel6A cellulase from which the modified TrCel6A cellulase is derived. The modified TrCel6A cellulase is capable of hydrolyzing polysaccharides using an inverting mechanism.

By "wild type" or "native" TrCel6A cellulase, it is meant the cellulases of SEQ ID NO: 1, without any amino acid substitutions.

For the purposes of the present invention, a "parental TrCel6A cellulase" or "parental cellulase" is a TrCel6A cellulase that does not contain the amino acid substitution(s) present in the modified TrCel6A cellulase, namely one or more amino acid substitutions selected from the group consisting of:
substitution of a basic amino acid at one or more of positions 129 and 410 by a charge-neutral or an acidic amino acid;
substitution of a charge-neutral amino acid at one or more of positions 322 and 363 by an acidic amino acid; and
substitution of an amino acid at position 186 by a threonine, but that is otherwise identical to the modified TrCel6A cellulase. As such, the parental TrCel6A cellulase may be a TrCel6A cellulase that contains amino acid substitutions at other positions that have been introduced by genetic engineering or other techniques and that is capable of hydrolyzing polysaccharides using an inverting mechanism. By way of example, the parental cellulase corresponding to a modified TrCel6A cellulase having basic amino acids substitutions at positions 129 and 410 to charge-neutral or acidic amino acids would be a TrCel6A cellulase that does not have charge-neutral or acidic amino acids at both of these positions, but that would be otherwise identical to the modified TrCel6A. However, the parental cellulase and the modified TrCel6A may contain amino acid substitutions at other positions provided that these amino acid substitutions are present in both the modified and parental cellulases. The parental cellulase could also be a wild-type enzyme. By comparing the activity of the modified TrCel6A cellulase with a parental cellulase that is identical to the modified cellulase except for the amino acid substitutions introduced in accordance with the invention, the effect of these amino acid substitutions on the activity of the enzyme in the presence of lignin can be quantified using the assays described below.

Alternatively, after production of a modified TrCel6A cellulase comprising one or more amino acid substitutions selected from the group consisting of:
substitution of a basic amino acid at one or more of positions 129 and 410 by a charge-neutral or an acidic amino acid;
substitution of a charge-neutral amino acid at one or more of positions 322 and 363 by an acidic amino acid; and
substitution of an amino acid at position 186 by a threonine, the modified TrCel6A cellulase may be subsequently further modified to contain additional amino acid substitutions. The modified TrCel6A cellulase being capable of hydrolyzing polysaccharides using an inverting mechanism.

In order to assist one of skill in the art regarding where other amino acid substitutions (other than positions 129, 186, 322, 363 and 410) of a given TrCel6A cellulase may be made to produce an active enzyme, an alignment of thirty-six Family 6 cellulases derived from fungal sources is provided in FIG. 1 along with a graph showing the frequency of occurrence of each amino acid of the consensus sequence at each position. Using the information provided in FIG. 1, one of skill in the art would recognize regions of low sequence conservation among Family 6 cellulases and could introduce additional amino acid substitutions in these regions provided that the enzyme exhibits Cel16A cellulase activity.

Decreasing the Inactivation of TrCel6A Cellulases by Lignin

The decrease in the inactivation of the modified TrCel6A cellulase by lignin is determined by measuring the degradation of cellulose or other suitable cellulase substrate (such as beta-glucan) in the presence and absence of lignin and then taking the ratio of activity in the presence of lignin to the activity in the absence of lignin. The lignin present in such a cellulose hydrolysis reaction can be part of the insoluble substrate, such as in pre-treated lignocellulose, or be isolated in a soluble or insoluble form. If the lignin is isolated or purified, the inactivation of the modified or parental TrCel6A cellulase by lignin is determined by measuring the cellulase activity in equivalent hydrolysis reactions, wherein one of the reactions contains a sufficient amount of lignin to reduce the cellulase activity. Alternatively, isolated lignin that has been treated to be less deactivating by coating with a non-specific protein such as bovine serum albumin (BSA), a surfactant or other chemical can be added to the control reaction in the same amounts as the untreated lignin. If the lignin is part of the insoluble substrate, the inactivation of the modified or parental TrCel6A cellulase by lignin is determined by taking the ratio of cellulase activity on a bleached substrate (from which the lignin has been removed, for example, by an oxidant such as chlorine dioxide) and the cellulase activity on an unbleached, lignin-containing substrate. A modified TrCel6A cellulase with decreased inactivation by lignin will show a higher activity ratio (+untreated, isolated lignin: no lignin or treated lignin) than the parental TrCel6A cellulase.

There are several assays for measuring cellulase activity of the modified and parental TrCel6A cellulases known to one of skill in the art. It should be understood, however, that the practice of the present invention is not limited by the method used to assess the activity of the modified TrCel6A cellulase.

For example, hydrolysis of cellulose can be monitored by measuring the enzyme-dependent release of reducing sugars, which are quantified in subsequent chemical or chemienzymatic assays known to one of skill in the art, including reaction with dinitrosalisylic acid (DNS). Hydrolysis of polysaccharides can also be monitored by chromatographic methods that separate and quantify soluble mono-, di- and oligo-saccharides released by the enzyme activity. In addition, soluble colorimetric substrates may be incorporated into agar-medium on which a host microbe expressing and secreting a parental or modified Family 6 cellulase is grown. In such an agar-plate assay, activity of the cellulase is detected as a colored or colorless halo around the individual microbial colony expressing and secreting an active cellulase.

Figure 4:
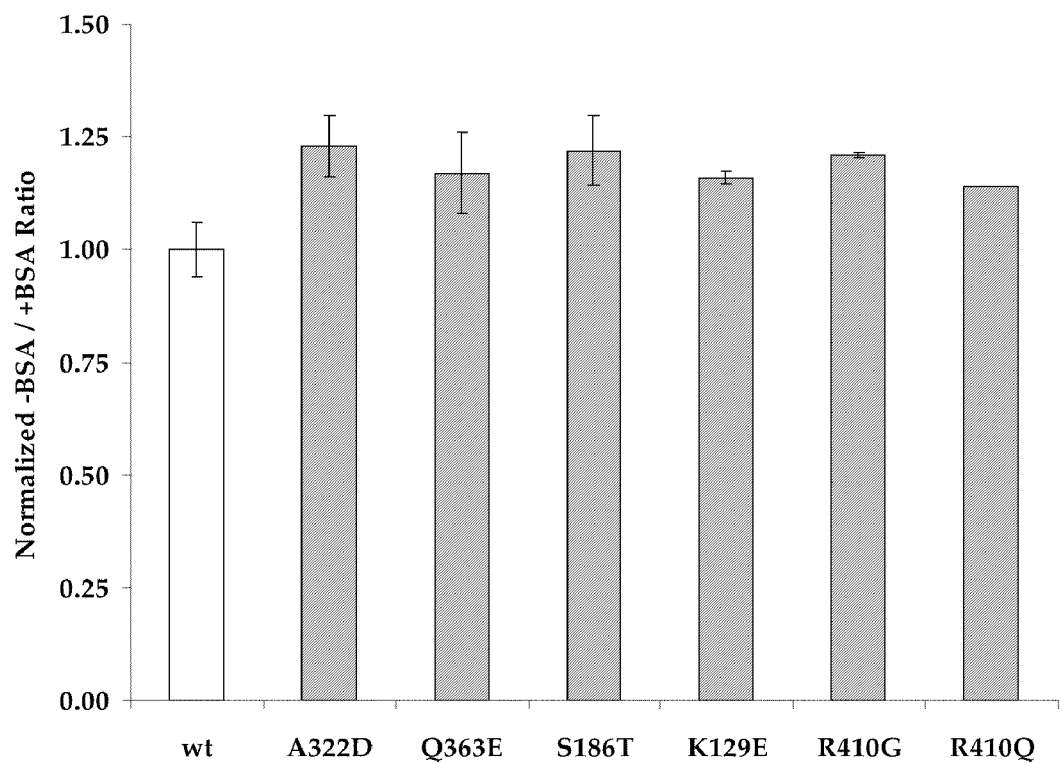
FIG. 4 is a bar graph showing ±BSA lignin ratios for modified TrCel6A cellulases normalized to ±BSA lignin ratios for the parental TrCel6A-S413P cellulase as measured in high throughput assay 1 (Example 6).

The effect of amino acid substitutions at positions 129, 186, 322, 363 and 410 on the lignin inactivation of a parental TrCel6A was determined via a comparative study of the relative cellulose-hydrolyzing activities of the parental TrCel6A-S413P and the modified TrCel6A cellulases in the presence of isolated, untreated lignin (−BSA) and treated lignin (+BSA), as described in Example 6. For each protein, the ratio of the two activities is normalized to 1.0 for the parental TrCel6A-S413P. The results are shown in FIG. 4. All of the modified Family 6 cellulases show at least a 15% higher ratio of activity after pre-incubation with untreated lignin: activity after pre-incubation with BSA-treated lignin.

In a preferred embodiment, the modified TrCel6A cellulase exhibits at least a 15% decrease in its inactivation by lignin relative to a parental cellulase as measured in the assays described in Examples 6 and 7. For example, the modified TrCel6A cellulase may exhibit from about 15% to about 400%, or any amount therebetween, decrease in its inactivation by lignin relative to a parental cellulase. The modified TrCel6A cellulase may exhibit 15%, 20%, 25%, 30%, 35%, 40%, 45%, 50%, 75%, 100%, 150%, 200%, 250%, 300%, 350% or 400% decrease in its inactivation by lignin relative to a parental cellulase.

Genetic Constructs Encoding Modified TrCel6A Cellulase

The present invention also relates to genetic constructs comprising a nucleic acid sequence encoding a modified TrCel6A cellulase. The modified cellulase-encoding nucleic acid sequence may be operably linked to regulatory nucleic acid sequences directing the expression and secretion of the modified TrCel6A cellulase from a host microbe. By "regulatory DNA sequences" it is meant a promoter and a DNA sequence encoding a secretion signal peptide. The regulatory DNA sequences are preferably functional in a fungal host. The regulatory DNA sequences may be derived from nucleic acid sequences that are highly expressed and secreted in the host microbe under industrial fermentation conditions. In a preferred embodiment, the regulatory sequences are derived from one or more of the nucleic acids sequences encoding *Trichoderma reesei* cellulase or hemicellulase.

The genetic construct may further comprise a nucleic acid sequence encoding a selectable marker to enable isolation of a genetically modified microbe transformed with the construct as is commonly known to those of skill in the art. The selectable marker may confer resistance to an antibiotic or the ability to grow on medium lacking a specific nutrient to the host organism that otherwise could not grow under these conditions. However, the present invention is not limited by the choice of selectable marker or nucleic acid sequence encoding the selectable marker, and one of skill in the art may readily determine an appropriate marker. In a preferred embodiment, the selectable marker confers resistance to hygromycin, phleomycin, kanamycin, geneticin, or G418, complements a deficiency of the host microbe in one of the trp, arg, leu, pyr4, pyr, ura3, ura5, his, or ade genes or confers the ability to grow on acetamide as a sole nitrogen source.

The genetic construct may further comprise other nucleic acid sequences, for example, transcriptional terminators, nucleic acid sequences encoding peptide tags, synthetic sequences to link the various nucleic acid sequences together, origins of replication, and the like. However, it should be understood that the practice of the present invention is not limited by the presence of any one or more of these other nucleic acid sequences.

Genetically Modified Microbes Producing Modified TrCel6A Cellulases

The modified TrCel6A cellulase may be expressed and secreted from a genetically modified microbe produced by transformation of a host microbe with a genetic construct encoding the modified TrCel6A cellulase. The host microbe may be a yeast or a filamentous fungus, particularly those microbes that are members of the phylum *Ascomycota*. Genera of yeasts useful as host microbes for the expression of modified TrCel6A cellulases of the present invention include *Saccharomyces, Pichia, Hansenula, Kluyveromyces, Yarrowia*, and *Arxula*. Genera of fungi useful as microbes for the expression of modified TrCel3A beta-glucosidases of the present invention include *Trichoderma, Hypocrea, Aspergillus, Fusarium, Humicola, Neurospora*, and *Penicillium*. Typically, the host microbe is one from which the gene(s) encoding any or all Family 6 cellulase have been deleted. In a most preferred embodiment, the host microbe is an industrial strain of *Trichoderma reesei*.

The genetic construct may be introduced into the host microbe by any number of methods known by one skilled in the art of microbial transformation, including but not limited to, treatment of cells with $CaCl_2$, electroporation, biolistic bombardment, PEG-mediated fusion of protoplasts (e.g. White et al., WO 2005/093072). After selecting the recombinant fungal strains expressing the modified TrCel6A cellulase, they may be cultured in submerged liquid fermentations under conditions that induce the expression of the modified TrCel6A cellulase. Preferably, the modified TrCel6A cellulase is produced in submerged liquid culture fermentation and separated from the cells at the end of the fermentation. The cells may be separated by filtration, centrifugation, or other processes familiar to those skilled in the art. The cell-free cellulase-containing fraction may then be concentrated (for example, via ultrafiltration), preserved, and/or stabilized prior to use.

Therefore the present invention also provides a process for producing a modified TrCel6A cellulase. The method comprises growing a genetically modified microbe comprising a nucleotide sequence encoding a modified TrCel6A cellulase, in a culture medium under conditions that induce expression and secretion of the modified TrCel6A cellulase, and recovering the modified TrCel6A cellulase from the culture medium. The modified TrCel6A cellulase comprising one or more amino acid substitutions selected from the group consisting of:
substitution of a basic amino acid at one or more of positions 129 and 410 by a charge-neutral or an acidic amino acid;
substitution of a charge-neutral amino acid at one or more of positions 322 and 363 by an acidic amino acid; and
substitution of an amino acid at position 186 by a threonine, wherein amino acids 83-447 of the modified TrCel6A cellulase are from about 47% to about 99.9% identical to amino acids 83-447 of SEQ ID NO: 1.

Production of Modified TrCel6A Cellulases

A modified TrCel6A cellulase of the present invention may be produced in a fermentation process using a genetically modified microbe comprising a genetic construct encoding the modified TrCel6A cellulase, e.g., in submerged liquid culture fermentation.

Submerged liquid fermentations of microorganisms, including *Trichoderma* and related filamentous fungi, are typically conducted as a batch, fed-batch or continuous process. In a batch process, all the necessary materials, with the exception of oxygen for aerobic processes, are placed in a reactor at the start of the operation and the fermentation is allowed to proceed until completion, at which point the product is harvested. A batch process for producing the modified TrCel6A cellulase of the present invention may be carried out in a shake-flask or a bioreactor.

In a fed-batch process, the culture is fed continuously or sequentially with one or more media components without the removal of the culture fluid. In a continuous process, fresh medium is supplied and culture fluid is removed continuously at volumetrically equal rates to maintain the culture at a steady growth rate.

One of skill in the art is aware that fermentation medium comprises a carbon source, a nitrogen source and other nutrients, vitamins and minerals which can be added to the fermentation media to improve growth and enzyme production of the host cell. These other media components may be added prior to, simultaneously with or after inoculation of the culture with the host cell.

For the process for producing the modified TrCel6A cellulase of the present invention, the carbon source may comprise a carbohydrate that will induce the expression of the modified TrCel6A cellulase from a genetic construct in the genetically modified microbe. For example, if the genetically modified microbe is a strain of *Trichoderma*, the carbon source may comprise one or more of cellulose, cellobiose, sophorose, and related oligo- or poly-saccharides known to induce expression of cellulases and beta-glucosidase in *Trichoderma*.

In the case of batch fermentation, the carbon source may be added to the fermentation medium prior to or simultaneously with inoculation. In the cases of fed-batch or continuous operations, the carbon source may also be supplied continuously or intermittently during the fermentation process. For example, when the genetically modified microbe is a strain of *Trichoderma*, the carbon feed rate is between 0.2 and 2.5 g carbon/L of culture/h, or any amount therebetween.

The process for producing the modified TrCel6A cellulase of the present invention may be carried at a temperature from about 20° C. to about 40° C., or any temperature therebetween, for example from about 25° C. to about 37° C., or any temperature therebetween, or from 20, 22, 25, 26, 27, 28, 29, 30, 32, 35, 37, 40° C. or any temperature therebetween.

The process for producing the modified TrCel6A cellulase of the present invention may be carried out at a pH from about 3.0 to 6.5, or any pH therebetween, for example from about pH 3.5 to pH 5.5, or any pH therebetween, for example from about pH 3.0, 3.2, 3.4, 3.5, 3.7, 3.8, 4.0, 4.1, 4.2, 4.3, 4.4, 4.5, 4.6, 4.7, 4.8, 4.9, 5.0, 5.2, 5.4, 5.5, 5.7, 5.8, 6.0, 6.2, 6.5 or any pH therebetween.

Following fermentation, the fermentation broth containing the modified TrCel6A cellulase may be used directly, or the modified TrCel6A cellulase may be separated from the fungal cells, for example by filtration or centrifugation. Low molecular solutes such as unconsumed components of the fermentation medium may be removed by ultra-filtration. The modified Family 6 cellulase may be concentrated, for example, by evaporation, precipitation, sedimentation or filtration. Chemicals such as glycerol, sucrose, sorbitol and the like may be added to stabilize the cellulase enzyme. Other chemicals, such as sodium benzoate or potassium sorbate, may be added to the cellulase enzyme to prevent growth of microbial contamination.

Cellulose Hydrolysis Process Using the Modified TrCel6A Cellulase

The modified TrCel6A cellulase of the present invention is used for the enzymatic hydrolysis of cellulose in a hydrolysis reaction further comprising lignin. For example, the modified TrCel6A cellulase of the present invention is used for the enzymatic hydrolysis of a pretreated lignocellulosic substrate. The modified TrCel6A cellulase of the present invention may be used in industrial processes such as the production of fermentable sugars, sugar alcohols or fuel alcohols.

The modified TrCel6A cellulase enzyme of the invention can be used for the enzymatic hydrolysis of a "pretreated lignocellulosic substrate." A pretreated lignocellulosic substrate is a material of plant origin that, prior to pretreatment, contains at least 20% cellulose (dry wt), more preferably greater than about 30% cellulose, even more preferably greater than 40% cellulose, for example 20, 22, 24, 26, 28, 30, 32, 34, 36, 38, 40, 42, 44, 46, 48, 50, 55, 60, 65, 70, 75, 80, 85, 90% or any % therebetween, and at least 10% lignin (dry wt), more typically at least 12% (dry wt) and that has been subjected to physical and/or chemical processes to make the fiber more accessible and/or receptive to the actions of cellulolytic enzymes.

After pretreatment, the lignocellulosic feedstock may contain higher levels of cellulose. For example, if acid pretreatment is employed, the hemicellulose component is hydrolyzed, which increases the relative level of cellulose. In this case, the pretreated feedstock may contain greater than about 20% cellulose and greater than about 12% lignin. In one embodiment, the pretreated lignocellulosic feedstock contains greater than about 20% cellulose and greater than about 10% lignin.

Lignocellulosic feedstocks that may be used in the invention include, but are not limited to, agricultural residues such as corn stover, wheat straw, barley straw, rice straw, oat straw, canola straw, and soybean stover; fiber process residues such as corn fiber, sugar beet pulp, pulp mill fines and rejects or sugar cane bagasse; forestry residues such as aspen wood, other hardwoods, softwood, and sawdust; grasses such as switch grass, miscanthus, cord grass, and reed canary grass; or post-consumer waste paper products.

The lignocellulosic feedstock may be first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, a hammer mill.

Non-limiting examples of pretreatment processes include chemical treatment of a lignocellulosic feedstock with sulfuric or sulfurous acid, or other acids; ammonia, lime, ammonium hydroxide, or other alkali; ethanol, butanol, or other organic solvents; or pressurized water (See U.S. Pat. Nos. 4,461,648, 5,916,780, 6,090,595, 6,043,392, 4,600,590, Weil et al. (1997)).

The pretreatment may be carried out to hydrolyze the hemicellulose, or a portion thereof, that is present in the lignocellulosic feedstock to monomeric sugars, for example xylose, arabinose, mannose, galactose, or a combination thereof. Preferably, the pretreatment is carried out so that nearly complete hydrolysis of the hemicellulose and a small amount of conversion of cellulose to glucose occurs. During the pretreatment, typically an acid concentration in the aqueous slurry from about 0.02% (w/w) to about 2% (w/w), or any amount therebetween, is used for the treatment of the lignocellulosic feedstock. The acid may be, but is not limited to, hydrochloric acid, nitric acid, or sulfuric acid. For example, the acid used during pretreatment is sulfuric acid.

One method of performing acid pretreatment of the feedstock is steam explosion using the process conditions set out in U.S. Pat. No. 4,461,648. Another method of pretreating the feedstock slurry involves continuous pretreatment, meaning that the lignocellulosic feedstock is pumped through a reactor continuously. Continuous acid pretreatment is familiar to those skilled in the art; see, for example, U.S. Pat. No. 5,536,325; WO 2006/128304; and U.S. Pat. No. 4,237,226. Additional techniques known in the art may be used as required such as the process disclosed in U.S. Pat. No. 4,556,430.

As noted above, the pretreatment may be conducted with alkali. In contrast to acid pretreatment, pretreatment with alkali does not hydrolyze the hemicellulose component of the feedstock, but rather the alkali reacts with acidic groups present on the hemicellulose to open up the surface of the substrate. The addition of alkali may also alter the crystal structure of the cellulose so that it is more amenable to hydrolysis. Examples of alkali that may be used in the pretreatment include ammonia, ammonium hydroxide, potassium hydroxide, and sodium hydroxide. The pretreatment is preferably not conducted with alkali that is insoluble in water, such as lime and magnesium hydroxide.

An example of a suitable alkali pretreatment, variously known as Ammonia Freeze Explosion, Ammonia Fiber Explosion or Ammonia Fiber Expansion ("AFEX" process), involves contacting the lignocellulosic feedstock with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. (See U.S. Pat. Nos. 5,171,592, 5,037,663, 4,600,590, 6,106,888, 4,356,196, 5,939,544, 6,176,176, 5,037,663 and 5,171,592). The flashed ammonia may then be recovered according to known processes.

The pretreated lignocellulosic feedstock may be processed after pretreatment but prior to the enzymatic hydrolysis by any of several steps, such as dilution with water, washing with water, buffering, filtration, or centrifugation, or a combination of these processes, prior to enzymatic hydrolysis, as is familiar to those skilled in the art.

The pretreated lignocellulosic feedstock is next subjected to enzymatic hydrolysis. By the term "enzymatic hydrolysis", it is meant a process by which cellulase enzymes act on cellulose to convert all or a portion thereof to soluble sugars. Soluble sugars are meant to include water-soluble hexose monomers and oligomers of up to six monomer units that are derived from the cellulose portion of the pretreated lignocellulosic feedstock. Examples of soluble sugars include, but are not limited to, glucose, cellobiose, cellodextrins, or mixtures thereof. The soluble sugars may be predominantly cellobiose and glucose. The soluble sugars may be predominantly glucose.

The enzymatic hydrolysis process preferably converts about 80% to about 100% of the cellulose to soluble sugars, or any range therebetween. More preferably, the enzymatic hydrolysis process converts about 90% to about 100% of the cellulose to soluble sugars, or any range therebetween. In the most preferred embodiment, the enzymatic hydrolysis process converts about 98% to about 100% of the cellulose to soluble sugars, or any range therebetween. The enzymatic hydrolysis process may be batch hydrolysis, continuous hydrolysis, or a combination thereof. The hydrolysis process may be agitated, unmixed, or a combination thereof.

The enzymatic hydrolysis process is preferably carried out at a temperature of about 45° C. to about 75° C., or any temperature therebetween, for example a temperature of 45, 50, 55, 60, 65, 70, 75° C., or any temperature therebetween, and a pH of about 3.5 to about 7.5, or any pH therebetween, for example a temperature of 3.5, 4.0, 4.5, 5.0, 5.5, 6.0, 6.5, 7.0, 7.5, or pH therebetween. The initial concentration of cellulose in the hydrolysis reactor, prior to the start of hydrolysis, is preferably about 4% (w/w) to about 15% (w/w), or any amount therebetween, for example 4, 6, 8, 10, 12, 14, 15% or any amount therebetween. The combined dosage of all primary cellulase enzymes may be about 1 to about 100 mg protein per gram cellulose, or any amount therebetween, for example 1, 5, 10, 15, 20, 25, 30, 40, 50, 60, 70, 80, 90, 100 mg protein per gram cellulose or any amount therebetween. The hydrolysis may be carried out for a time period of about 12 hours to about 200 hours, or any time therebetween, for example, the hydrolysis may be carried out for a period of 15 hours to 100 hours, or any time therebetween, or it may be carried out for 12, 14, 15, 20, 25, 30, 35, 40, 45, 50, 55, 60, 65, 70, 75, 80, 85, 90, 95, 100, 120, 140, 160, 180, 200 or any time therebetween. It should be appreciated that the reaction conditions are not meant to limit the invention in any manner and may be adjusted as desired by those of skill in the art.

The enzymatic hydrolysis process is typically carried out in a hydrolysis reactor. The cellulase enzyme is added to the pretreated lignocellulosic feedstock (also referred to as the "substrate") prior to, during, or after the addition of the substrate to the hydrolysis reactor.

The cellulase enzyme may be a cellulase enzyme mixture comprising the modified TrCel6A cellulase and other cellulase enzymes produced in one or more submerged liquid culture fermentations. The modified TrCel6A cellulase and other cellulase enzymes thus produced may be separated from the cells at the end of the fermentation by filtration, centrifugation, or other processes familiar to those skilled in the art. The cell-free cellulase-containing fraction(s) may then be concentrated (for example, via ultrafiltration), preserved, and/or stabilized prior to use. Alternatively, the modified TrCel6A cellulase and other cellulase enzymes are not separated from the cells, but are added to the enzymatic hydrolysis with the cells.

EXAMPLES

The present invention will be further illustrated in the following examples. However, it is to be understood that these examples are for illustrative purposes only and should not be used to limit the scope of the present invention in any manner.

Example 1 describes the strains and vectors used in the following examples. Example 2 describes the cloning of the TrCel6A-S413P gene and transformation in yeast. Example 3 summarizes the preparation of the error prone-PCR library of TrCel6A-S413P. Example 4 describes the expression of modified TrCel6A cellulases from microculture. Example 5 describes the isolation and preparation of lignin. Examples 6 and 7 describe the high-throughput screening assays to identify modified TrCel6A cellulases with decreased inactivation by lignin. Example 8 describes the preparation of aggregate modified TrCel6A cellulases. Example 9 describes the expression and purification of parental and modified TrCel6A cellulases. Example 10 summarizes the testing of purified parental and modified TrCel6A cellulases in high-throughput assay 1 and assay 2. Finally, Example 11 describes the testing of purified parental and modified TrCel6A cellulases in lignin inactivation time course experiments.

Example 1

Strains and Vectors

*Saccharomyces cerevisiae* strain YDR483W BY4742 [14317] (MATα his3Δ1 leu2Δ0 lys2 Δ0 ura3 Δ0 Δkre2) was obtained from ATCC (#4014317). The YEp352/PGK91-1 vector was obtained from the National Institute of Health. The YEpFLAG ΔKpn10-S413P vector is described in U.S. Patent Application 60/841,507. The YEpFLAG-1 vector was obtained from Sigma as a part of the Amino-Terminal Yeast FLAG Expression Kit.

Example 2

Cloning of the TrCel6A-S413P Gene into the YEp352/PGK91-1 and Transformation in Yeast In order to facilitate cloning using NheI and KpnI restriction enzymes, the unique NheI site at position 1936 of the YEp352/PGK91-1 vector was blunted using the DNA Polymerase I large (Klenow) fragment to generate YEp352/PGK91-1 ΔNheI. The TrCel6A-S413P gene was amplified by PCR from YEpFLAG ΔKpn10-S413P vector (U.S. Patent Provisional No. 60/841,507) using primers 5'NheCel6A and 3'BglKpnCel6A. In parallel, the yeast alpha-factor leader sequence was amplified by PCR from the YEpFLAG-1 vector (Sigma) using primers (5'BglAlphaSS and 3'NheAlphaSS) to introduce BglII at the 5' end and an NheI site at 3' end of the amplicon.

The yeast alpha-factor leader sequence was isolated by BglII/NheI digestion and a three piece ligation performed with the TrCel6A-S413P gene (isolated by NheI/BglII digestion) and YEp352/PGK91-1 ΔNheI vector (isolated by BglII digestion). The resulting vector YEp352/PGK91-1 ΔNheI-alpha$_{ss}$-TrCel6A-S413P (FIG. 2) was transformed in yeast strain BY4742 using the procedure described by Gietz, R. D. and Woods, R. A. (2002). Primer sequences are listed below:

```
5'BglAlphaSS:
                                         (SEQ ID NO: 46)
5'ACC AAA AGA TCT ATG AGA TTT CCT TCA ATT 3'NheAlphaSS:
                                         (SEQ ID NO: 47)
5'TGA GCA GCT AGC CCT TTT ATC CAA AGA TAC 5'NheCel6A:
                                         (SEQ ID NO: 48)
5'AAA AGG CTA GCT GCT CAG CGT CTG GGG C 3'BglKpnCel6A:
                                         (SEQ ID NO: 49)
5'GAG CTC AGA TCT GGT ACC TTA CAG GAA CGA TGG GTT
```

Example 3

Making Error Prone-PCR Libraries

Random mutagenesis libraries were generated using a Mutazyme® II DNA polymerase method. For the Mutazyme® II DNA polymerase method, a series of four independent PCR were performed using 10, 20, 30, 40 ng of YEp352/PGK91-1 ΔNheI-α$_{ss}$-TrCel6A-S413P vector and the Mutazyme® II DNA polymerase with primers YalphaN21 and 3'PGK-term. The amplification was done for 25 cycles. The four PCR products were pooled and diluted to 10 ng/μL. A second PCR mutagenesis step was performed using 30 ng of pooled PCR product with Mutazyme® II DNA polymerase using the same primers for 30 amplification cycles. The YEp352/PGK91-1ΔNheI-α$_{ss}$-TrCel6A-S413P vector was digested with NheI and KpnI and the empty vector fragment was isolated. This linear fragment and the final amplicon were transformed simultaneously and cloned by in vivo recombination into yeast strain BY4742 (Butler et al., 2003).

```
YalphaN21:
5'AGC ACA AAT AAC GGG TTA TTG    (SEQ ID NO: 45)

3'PGK-term:
5'GCA ACA CCT GGC AAT TCC TTA CC (SEQ ID NO: 56)
```

Example 4

Expression and Isolation of Parental and Modified TrCel6A Cellulases from Microplate Cultures This example describes the selection and expression of TrCel6A-S413P and modified TrCel6A cellulases from *Saccharomyces cerevisiae* for use in high-throughput screening assays (Examples 6 and 7).

Saccharomyces cerevisiae transformants from Example 3 were grown on plates containing synthetic complete medium (SC: 2% agar w/v, 0.17% yeast nitrogen base w/v, 0.078%-Ura drop-out supplement w/v, 2% glucose w/v, 2% casamino acids w/v, 0.5% ammonium sulfate w/v, pH 5.5) and 0.12% Azo-barley-beta-glucan (Megazyme) for 4 days at 30° C.

Colonies showing visible clearing halos after an overnight incubation at 45° C. were selected for liquid media pre-cultures by toothpick inoculation of 0.15 mL synthetic complete media (SC: 0.17% yeast nitrogen base w/v, 0.078%-Ura drop-out supplement w/v, 2% glucose w/v, 2% casamino acids w/v, 0.5% ammonium sulfate w/v) in 96-well microplates. Pre-cultures were grown overnight (16-18 hr) at 30° C. with orbital shaking to stationary phase. For expression culture inoculation, 25 μL of pre-culture was used to inoculate 1 mL of SC media in deepwell microplates containing one glass bead. Expression cultures were grown for 3 days at 30° C. with orbital shaking and humidity control. Plates were centrifuged at 710×g for 5 minutes to pellet cells and supernatant was aspirated for screening assays (Examples 6 and 7). To the remaining pre-culture, stocks were prepared by the addition of glycerol to a final concentration of 15% and stored at −80° C.

Example 5

Preparation of Lignin

Wheat straw was pretreated using the methods described in U.S. Pat. No. 4,461,648. Following pretreatment, sodium benzoate was added at a concentration of 0.5% as a preservative. The pretreated material was then washed with six volumes of lukewarm (~35° C.) tap water using a Buchner funnel and filter paper.

A sample of pretreated wheat straw (167 g wet; 30% solids; 60% cellulose) was added to 625 mL of 82% $H_2SO_4$ with stirring in a 1 L flask, then stoppered and incubated at 50° C. with shaking for 4 hours. The remaining solids were filtered to dampness using a Buchner funnel and a glass fiber filter, resuspended in 1 L of water and adjusted to pH 4.5 with NaOH. The solids were filtered and washed with ~8 L water. The solids are referred to herein as "lignin".

Bovine serum albumin (BSA) treatment of lignin was performed by incubating equal amounts (w/w) of lignin and BSA, at a concentration of 30 g/L in 50 mM citrate buffer (pH 5) containing 0.1% sodium benzoate, for 5 days at 50° C. with shaking.

Example 6

High-Throughput Screening of Trichoderma reesei Cel6A Gene Libraries for Modified Family 6 Cellulase with Resistance to Lignin—Assay 1

This example describes the screening of modified TrCel6A cellulases in order to identify those with resistance to inactivation by lignin in comparison to the parent TrCel6A-S413P that had been cloned into Saccharomyces cerevisiae.

Yeast expressed TrCel6A-S413P pre-binding to cellulose. An aliquot (0.175 mL) of supernatant from culture containing modified TrCel6A cellulase as described in Example 4 was added to two separate microplate wells containing 0.05 mL cellulose at a concentration of 0.167% w/v, and incubated for 90 minutes at 4° C. with orbital shaking. Microplates were then centrifuged at 2800×g for 3 min and 0.175 mL of supernatant was removed. An additional aliquot of supernatant (0.175 mL) from each modified TrCel6A was added to the same microplate wells and incubated for another 90 minutes under the same conditions. Microplates were again centrifuged at 2800×g for 3 min and 0.175 mL of supernatant was removed. A 0.175 mL volume of 50 mM citrate buffer (pH 5) was added to all wells and immediately the microplates were centrifuged at 2800×g for 3 min. Supernatant (0.175 mL) was removed.

Cellulose hydrolysis. Each modified TrCel6A cellulase was incubated with both 2.68% (w/v) lignin and BSA-treated lignin (0.10 mL) for 2 hours at 50° C. with orbital shaking. Following this period, Trichoderma reesei Cel7B and Cel5A (40 mg protein/g cellulose) and 125 IU/g cellulose A. niger beta-glucosidase were added and the incubation proceeded for an additional 3 hours. Microplates were centrifuged for 3 min at 2800×g and an aliquot of supernatant was sampled for glucose. Enzyme activity was measured via the detection of glucose using a standard glucose oxidase/peroxidase coupled reaction assay (Trinder, 1969). A sample of the data from one screening plate is shown in FIG. 3, panel A.

Contained in each 96-well microplate were six parental TrCel6A-S413P controls used for comparison. A ±BSA-treated lignin ratio was calculated for all modified TrCel6A cellulases and parental TrCel6A-S413P cellulase by dividing the cellulase activity in the presence of untreated lignin by the cellulase activity in the presence of BSA-treated lignin. The activity ratio for each modified TrCel6A cellulase was compared to the average of six parental TrCel6A-S413P controls on a particular microplate and positives (those having increased ratios) were selected at the 95% confidence level using a t-test. All positive cellulases were produced again in microculture and re-screened to reduce the number of false positives. Plasmid DNA comprising genes encoding modified TrCel6A cellulases with decreased lignin inactivation was isolated from yeast cultures grown from the glycerol stocks prepared in Example 4. The modified TrCel6A cellulase genes were subjected to DNA sequencing to identify mutations that confer altered substrate specificity.

Example 7

High-Throughput Screening of Trichoderma reesei Cel6A Gene Libraries for Modified Family 6 Cellulase with Resistance to Lignin—Assay 2

This example describes an additional screening of modified TrCel6A cellulases for those resistant to lignin using another high-throughput assay.

An aliquot (0.15 mL) of yeast supernatant as described in Example 4 was pre-incubated with lignin (1.6% w/v) in a 0.25 mL citrate buffered (50 mM; pH 5) reaction. An equivalent aliquot of supernatant from each modified cellulase was also pre-incubated with lignin (1.6% w/v) which was pre-treated with BSA. Pre-incubation was performed for 5.5 hours, in a 96-well microplate containing 1 glass bead, at 50° C. with orbital shaking (NB Innova 44). Contained in each 96-well microplate were six parent TrCel6A-S413P controls used for comparison. Following pre-incubation, microplates were centrifuged for 5 min at 2800×g and the supernatant was aspirated for residual activity assays.

Supernatant (0.05 mL) was incubated with 0.5% beta-glucan in a 100 μL citrate buffered (50 mM; pH 5) reaction. Residual activity assays were performed for 16 hours for samples pre-incubated with lignin and 3 hours for samples pre-incubated with BSA-treated lignin, in a PCR plate, at 50° C. A glucose standard curve was placed in the first column of the PCR ranging from 3 to 0.05 mg/mL. Following incubation, 0.08 mL of DNS reagent was added to all wells and the plates were boiled for 10 min. An aliquot (0.15 mL) was transferred to a microplate and the absorbance was measured at 560 nm. Residual enzyme activity was determined by converting $A_{560}$ values to reducing equivalents using the glucose standard curve. A sample of the data from one screening plate is shown in FIG. 3, panel B. An activity ratio was calculated for all modified TrCel6A cellulases and the parental TrCel6A-S413P controls by dividing the residual enzyme activity in the presence of untreated lignin by the residual enzyme activity in the presence of BSA-treated lignin. The activity ratio for each modified TrCel6A was compared to the average of six parental TrCel6A-S413P controls on a particular microplate and positives (those having increased ratios) were selected at the 95% confidence level using a t-test. All positive modified TrCel6A cellulases were produced again in microculture and re-screened to reduce the number of false positives.

DNS Reagent Contains:

| Component | g/L |
|---|---|
| 3,5-Dinitosalicylic acid (Acros) | 20 |
| Sodium hydroxide (Fisher) | 20 |
| Phenol (Sigma) | 4 |
| Sodium metabisulfate (Fisher) | 1 |

Example 8

Making the Aggregate Modified TrCel6A Cellulases

Lignin-resistant mutations were combined into two aggregate modified TrCel6A cellulases. Table 2 shows the steps performed to generate the aggregate modified TrCel6A cellulases, TrCel6A-K129E-S186T-A322D-Q363E-S413P and TrCel6A-K129E-S186T-A322D-Q363E-R410Q-S413P.

```
PSP4-C  5'-GGCCACTGCTGCAGCAGCTGTCGCAGAAGTTCCCTCTTTTATGTGGC-3'   (SEQ ID NO: 50)

PSP5-C  5'-GCCACATAAAAGAGGGAACTTCTGCGACAGCTGCTGCAGCAGTGGCC-3'   (SEQ ID NO: 51)

PSP6-B  5'-GCCCTTGCCTCGAATGGCGAATACACTATTGCCGATGGTGGCGTCGCC-3'  (SEQ ID NO: 52)

PSP7-B  5'-GGCGACGCCACCATCGGCAATAGTGTATTCGCCATTCGAGGCAAGGGC-3'  (SEQ ID NO: 53)

PSP8    5'-TACACGCAAGGCAACGATGTCTACAACGAGAAG-3'                 (SEQ ID NO: 54)

PSP9    5'-CTTCTCGTTGTAGACATCGTTGCCTTGCGTGTA-3'                 (SEQ ID NO: 55)

DK091   5'-GACAGCAGTGCGCCACAGTTTGACCCCCACTGT-3'                 (SEQ ID NO: 57)

DK092   5'-ACAGTGGGGGTCAAACTGTGGCGCACTGCTGTC-3'                 (SEQ ID NO: 58)
```

To perform gap repair, the vector YEp352/PGK91-1-$\alpha_{ss}$-NKE was digested with NheI and KpnI and purified on gel. The digested YEp352/PGK91-1-$\alpha_{ss}$-NKE vector and the amplicons were transformed in yeast (*Saccharomyces cerevisiae* strain BY4742) using the procedure described by Gietz, R. D. and Woods, R. A., (2002).

TABLE 2

Generation of modified TrCel6A cellulases by PCR

| PCR | Step | Template | Primer 1 | Primer 2 | Amplicon |
|---|---|---|---|---|---|
| 1 | 1 | YEp352/PGK91-1-$\alpha_{ss}$-NKE TrCel6A- S413P-Q363E | Y$\alpha$N21 | PSP9 | PCR 1 Step 1 |
|   | 1 | YEp352/PGK91-1-$\alpha_{ss}$-NKE TrCel6A- S413P-Q363E | PSP8 | 3'PGK-Term | PCR 1 Step 1 |
|   | 2 | Both PCR 1 Step 1 megaprimers | Y$\alpha$N21 | 3'PGK-Term | PCR 1 Step 2 |
| 2 | 1 | PCR 1 Step 2 | Y$\alpha$N21 | PSP7B | PCR 2 Step 1 |
|   | 1 | PCR 1 Step 2 | PSP6B | 3'PGK-Term | PCR 2 Step 1 |
|   | 2 | Both PCR 2 Step 1 megaprimers | Y$\alpha$N21 | 3'PGK-Term | PCR 2 Step 2 |
| 3 | 1 | PCR 2 Step 2 | Y$\alpha$N21 | PSP5C | PCR 3 Step 1 |
|   | 1 | PCR 2 Step 2 | PSP4C | 3'PGK-Term | PCR 3 Step 1 |
|   | 2 | Both PCR 3 Step 1 megaprimers | Y$\alpha$N21 | 3'PGK-Term | PCR 3 Step 2 |
| 4 | 1 | PCR 3 Step 2 | Y$\alpha$N21 | DK092 | PCR 4 Step 1 |
|   | 1 | PCR 3 Step 2 | DK091 | 3'PGK-Term | PCR 4 Step 1 |
|   | 2 | Both PCR 4 Step 1 megaprimers | Both fragments were cloned in YEp352/PGK91-1-$\alpha_{ss}$-NKE using the Gap repair method in yeast. | | |

Example 9

Expression and Purification of TrCel6A-S413P and Modified TrCel6A Cellulases from Large Scale Cultures 500 mL of sterile YPD medium (10 g/L yeast extract, 20 g/L peptone and 20 g/L glucose) was inoculated with 10 mL of an overnight culture of transformed *S. cerevisiae* grown from cells freshly picked from an agar plate. The 500 mL cultures were then incubated for 96 hours at 30° C. with orbital shaking.

After incubation, the broth from each culture was centrifuged for 10 minutes at 16,700×g and the pellet (containing yeast cells) discarded. The pH of the supernatant was adjusted to 5.0 and then allowed to cool to 4° C. for an hour. Subsequent to cooling, 625 g $(NH_4)_2SO_4$ was added to bring the yeast supernatant to 93% saturation. Precipitation was allowed to occur over a period of 2 hours at 4° C. with constant stirring. After centrifugation for 15 minutes at 16,700×g, the supernatant was discarded.

The pellet was resuspended with pipetting in 20 mL of 50 mM citrate, pH 5.0. Once the pellet was resuspended, 80 mL of 0.1 M sodium acetate, 200 mM glucose and 1 mM gluconic acid lactone, pH 5.0 was added. Samples were then incubated at 4° C. for 30 min with gentle stirring. Each sample was then centrifuged at 710×g for 3 minutes to pellet any insoluble material. The supernatant was removed carefully with a pipette to prevent disruption of the pellet and retained. The TrCel6A cellulase in each sample was purified by APTC affinity chromatography as described by (Piyachomkwan et al., 1997). Purified TrCel6A cellulases were buffer exchanged into 50 mM citrate, pH 5.0 and concentrated using a Centricon (Millipore) centrifugal concentrator with a 5 kDa NMWL polyethersulfone membrane. Protein concentrations were measured by UV absorbance (280 nm) using an extinction coefficient of $\epsilon_{280\ nm}=2.062\ mL \cdot mg^{-1} \cdot cm$.

Example 10

Assaying Purified Aggregate Modified TrCel6A Cellulases in High-Throughput Assay 1 and Assay 2

TrCel6A-S413P, TrCel6A-K129E-S186T-A322D-Q363E-S413P and TrCel6A-K129E-S 186T-A322D-Q363E-R410Q-S413P were expressed and purified as described in Example 10. The TrCel6A cellulases were tested in high-throughput assay 1 and assay 2 as described in Examples 6 and 7. The concentration of TrCel6A was 0.02 mg/mL. The ±BSA-lignin ratio was normalized to TrCel6A-S413P and P-values were calculated for the aggregate modified TrCel6A cellulases (FIG. 5 and Table 3).

Example 11

Testing Purified Modified TrCel6A Cellulases in Lignin Inactivation Time Course Assays Purified TrCel6A (0.06 mg) cellulases were incubated with untreated lignin (1.04 mg) in stoppered, glass flasks in a total volume of 2 mL of 50 mM citrate buffer, pH 5.0. Incubations were done at 50° C. with orbital shaking. 0.2 mL samples were collected from each flask at 0, 0.5, 1, 2, 3, 4, 6, 14 and 24 hr. Each sample was centrifuged to separate the lignin and stored at 4° C.

Upon completion of the time course, each sample was mixed briefly to resuspend the pellet and 0.05 mL of slurry containing both soluble and insoluble material added to a microtitre plate containing 3 glass beads/well. To each well, 0.02 mL of a dilute preparation of *Trichoderma* cellulase devoid of cellobiohydrolase activity (1 µg total protein) and purified *Trichoderma* Cel3A (1.4 µg) were added to complement TrCel6A hydrolysis activity. Finally a 0.2 mL slurry of delignified cellulose (0.25% cellulose) was added to each well. The assay plate was incubated at 50° C. for 2 hr with orbital shaking. The plate was then centrifuged at 710×g for 2 min and the glucose concentrations measured as described in Example 6.

Glucose concentrations were converted to TrCel6A activity, expressed as mg glucose produced/hr/mg of TrCel6A protein. The activity measured at t=0 hr, in the absence of incubation with lignin, was the enzyme's specific activity. Activities measured throughout the time course were divided by the activity measured at t=0 in order to calculate a relative residual activity of TrCel6A. For the purposes of analyzing the results, measurements of relative residual activity were considered representative of the relative residual active TrCel6A concentration. Standard curves were used to demonstrate that changes in TrCel6A concentration and activity were linear over the concentrations of enzyme and substrate used in this assay.

The residual TrCel6A versus time data were modeled using Equation 1. In this equation, E represents the enzyme, L represents lignin, EL represents a reversible enzyme-lignin complex and EL* represents an irreversible enzyme-lignin complex. $K_L$ represents [E][L]/[EL] at steady state while $k_L$ is a rate constant describing the rate of conversion of the reversible to the irreversible enzyme-lignin complex. A minimum of two replicate data sets for each modified TrCel6A cellulase were generated.

TABLE 3

Normalized ±BSA-lignin ratios and P-values for the aggregate modified TrCel6A cellulases.

| | Assay 1 | | Assay 2 | |
| --- | --- | --- | --- | --- |
| | Normalized ±BSA Lignin Ratio | P-value | Normalized ±BSA Lignin Ratio | P-value |
| TrCel6A-S413P | 1.00 | — | 1.00 | — |
| TrCel6A-K129E-S186T-A322D-Q363E-S413P | 1.36 | 0.001 | 1.63 | <0.001 |
| TrCel6A-K129E-S186T-A322D-Q363E-R410Q-S413P | — | — | 2.14 | <0.001 |

Figure 6:
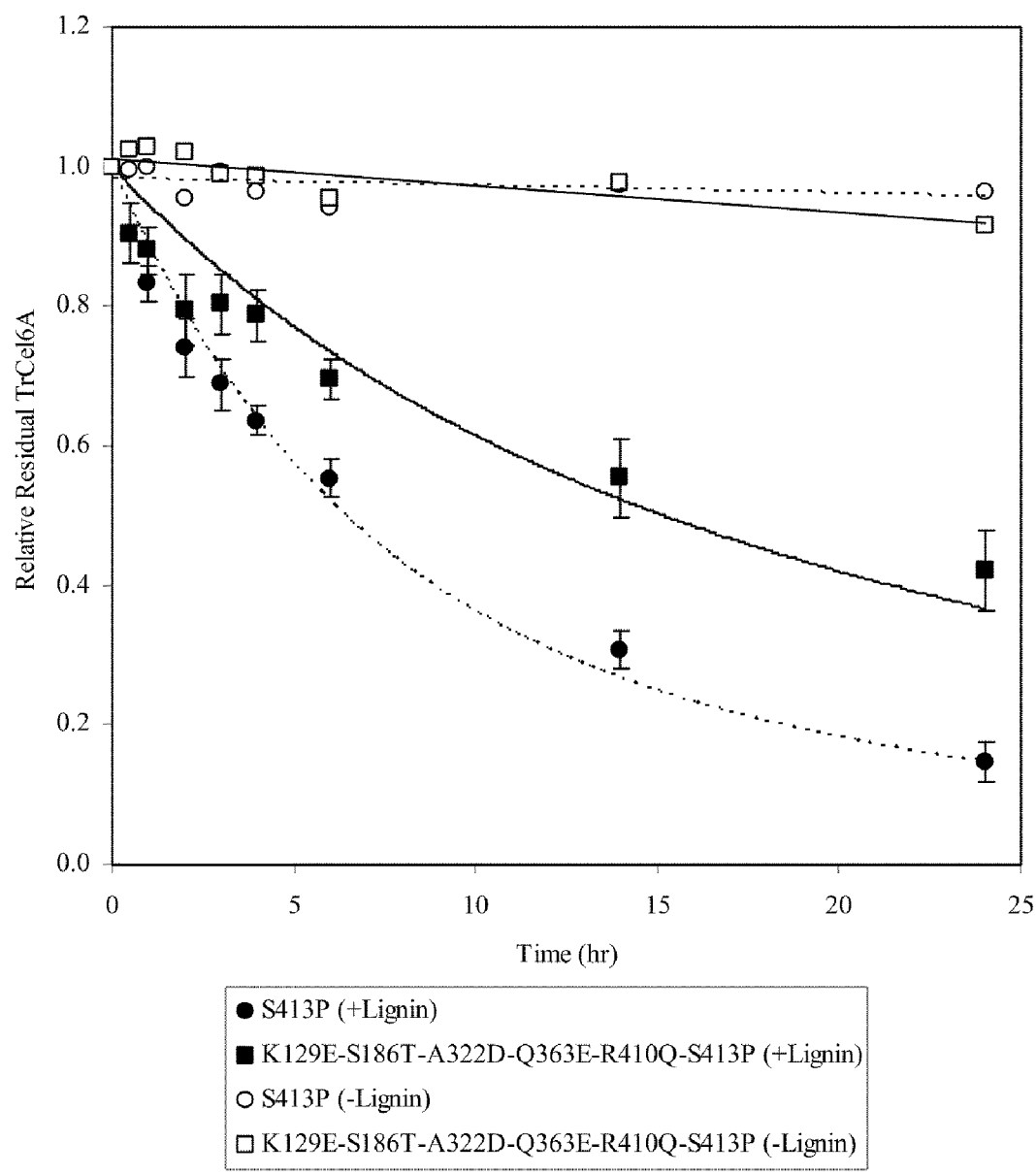
FIG. 6 shows the lignin inactivation time course results for TrCel6A-S413P and TrCel6A-K129E-S186T-A322D-Q363E-R410Q-S413P. Residual TrCel6A activity as a function of time in the lignin slurry was measured and analyzed as described in Example 9.

Sample lignin inactivation time course results are shown in FIG. 6 for TrCel6A-S413P and TrCel6A-K129E-S186T-A322D-Q363E-R410Q-S413P. At each time during the 24 hr incubation with lignin, residual activity of TrCel6A-K129E-S186T-A322D-Q363E-R410Q-S413P is greater than TrCel6A-S413P, indicating that a larger fraction of the modified TrCel6A was active at each time point. As controls, TrCel6A-S413P and TrCel6A-K129E-S186T-A322D-Q363E-R410Q-S413P were incubated in the absence of lignin under otherwise the same experimental conditions. These controls demonstrate that both TrCel6A cellulases were stable in solution in the absence of lignin over the duration of these assays. Therefore, an increase in the relative residual activity of a modified TrCel6A cellulase relative to TrCel6A-S413P in the presence of lignin is due to a reduced rate of inactivation due to the presence of lignin rather than any potential improvement in thermal stability of the modified TrCel6A.

Figure 7:
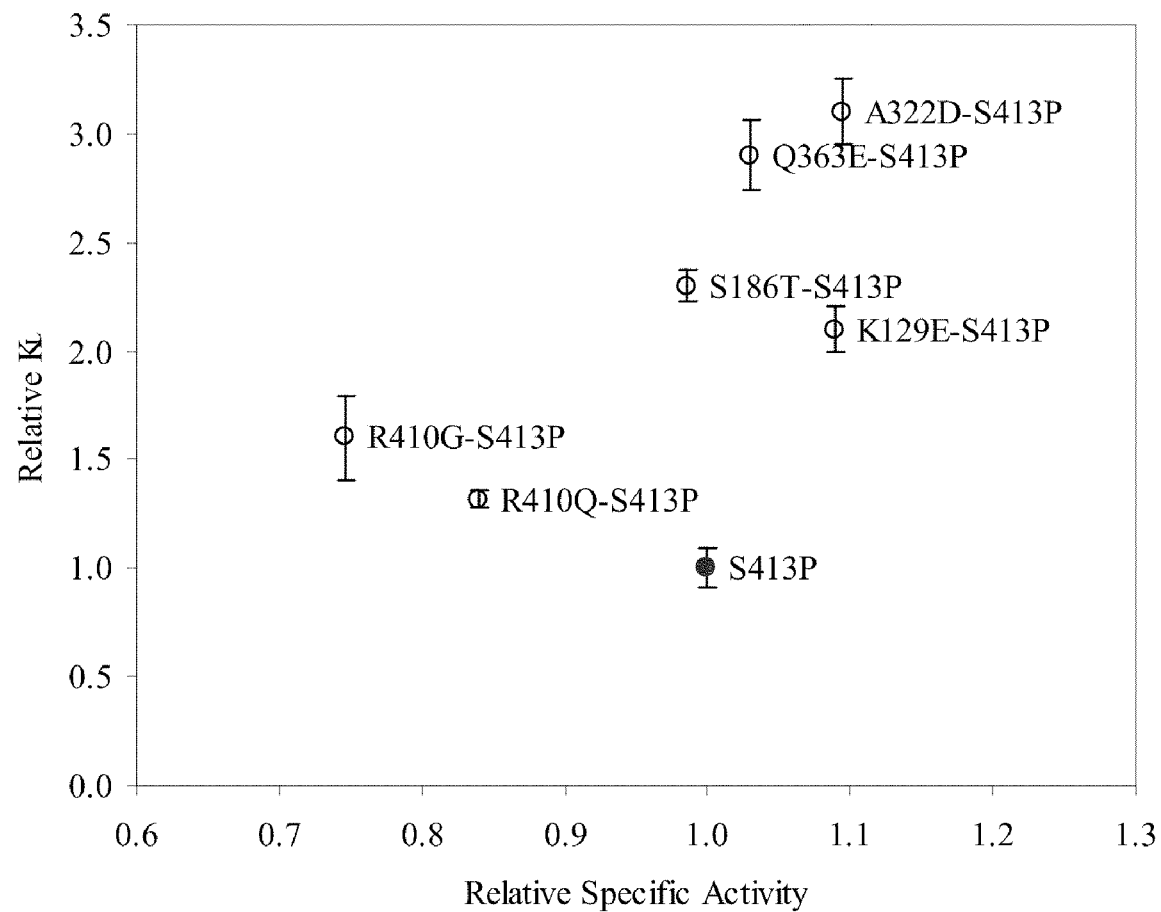
FIG. 7 is a scatter plot of the relative $K_L$ and the relative specific activities of modified TrCel6A cellulases and TrCel6A-S413P as determined in lignin inactivation time course assays.
Figure 8:
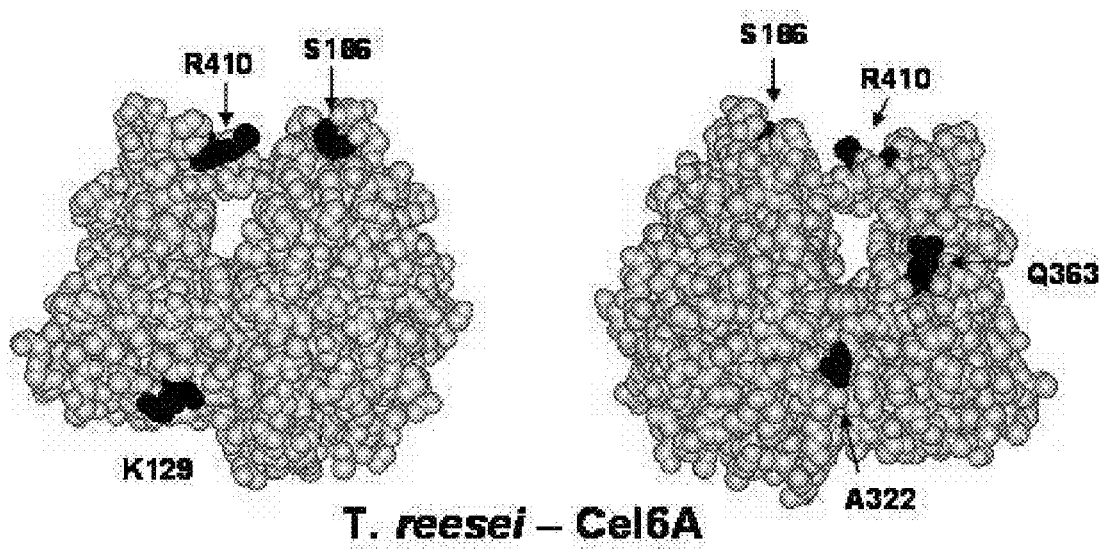
FIG. 8 shows the space-filling (CPK) model for the crystal structures of *T. reesei* Cel6A using coordinates from PDB files 1CB2. The view to the right is a 180 degree rotation around the centered vertical axis of the view on the left.

Modeling was done using 4th order Runge-Kutta spreadsheet in Microsoft Excel. In order to model the residual TrCel6A versus time results in a given experiment, the results for TrCel6A-S413P were fit by varying $K_L$ and $k_L$. Error minimization was done by the method of least squares as known to those of skill in the art. For modeling modified TrCel6A cellulases, the $k_L$ value was fixed to that determined for TrCel6A-S413P in the same experiment and varying $K_L$. Standard errors in the model fit to at least duplicate data sets were determined using a model comparison approach (Motulsky, H., and A. Christopoulos (2004)). The $K_L$ determined for each modified TrCel6A cellulase was divided by the $K_L$ determined for TrCel6A-S413P in order to calculate a relative $K_L$. Similarly, the specific activity of each modified TrCel6A was divided by the specific activity of TrCel6A-S413P in order to calculate a relative specific activity. Modified TrCel6A cellulases with a $K_L$ significantly higher (P<0.05, Student's t-test) than TrCel6A-S413P are shown in Table 4. A scatter plot of the relative $K_L$ and relative specific activity of each lignin-resistant modified TrCel6A cellulase and TrCel6A-S413P is shown in FIG. 7.

TABLE 4

$$E + L \underset{}{\overset{K_L}{\rightleftharpoons}} EL \overset{k_L}{\rightarrow} EL^* \quad \text{Equation 1}$$

Lignin inactivation constants ($K_L$) for modified TrCel6A cellulases

| TrCel6A | Relative $K_L$ | Standard Error | P-value | Relative Specific Activity |
|---|---|---|---|---|
| TrCel6A-K129E-S413P | 2.1 | 0.11 | <0.001 | 1.09 |
| TrCel6A-S186T-S413P | 2.3 | 0.07 | <0.001 | 0.99 |
| TrCel6A-A322D-S413P | 3.1 | 0.15 | <0.001 | 1.10 |
| TrCel6A-Q363E-S413P | 2.9 | 0.16 | <0.001 | 1.03 |
| TrCel6A-R410G-S413P | 1.6 | 0.20 | 0.009 | 0.75 |
| TrCel6A-R410Q-S413P | 1.3 | 0.04 | 0.02 | 0.84 |
| TrCel6A-S413P | 1.0 | 0.09 | — | 1.00 |

This assay demonstrated that six modified TrCel6A cellulases had significantly higher $K_L$ values and therefore were more resistant to lignin inactivation, compared to TrCel6A-S413P.

Figure 10:
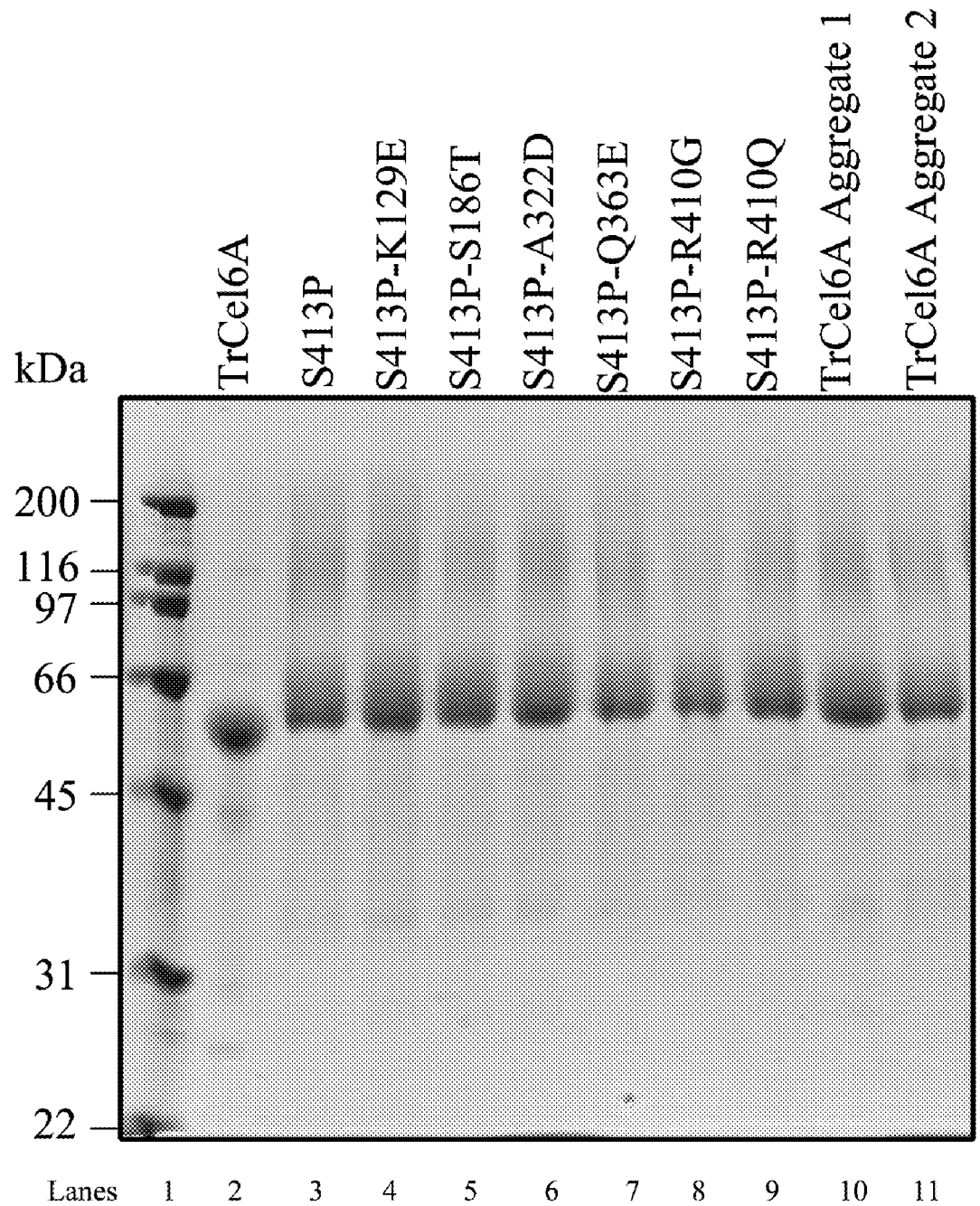
FIG. 10 shows a 10% SDS-PAGE gel of the purified parental and modified TrCel6A enzymes. Purified TrCel6A cellulases (5 μg each) were separated by 10% SDS-PAGE and the gel stained with Coomassie Brilliant Blue R250. In this figure, TrCel6A Aggregate 1 (lane 10) and TrCel6A Aggregate 2 (lane 11) refer to TrCel6A-K129E-S 186T-A322D-Q363E-S413P and TrCel6A-K129E-S186T-A322D-Q363E-R410Q-S413P, respectively. TrCel6A purified from *Trichoderma* cellulase (lane 2) and molecular mass standards (lane 1) are shown for reference.

The purified TrCel6A enzymes, parental and modified, were separated by 10% SDS-PAGE and visualized by Coomassie blue staining (FIG. 10). This gel demonstrates that the relative purity of the modified TrCel6A enzymes (lanes 4-11) were similar to TrCel6A-S413P (lane 3). The major band observed for modified and parental TrCel6A enzymes had an apparent molecular mass of about 60 kDa. In this figure, TrCel6A Aggregate 1 (lane 10) and TrCel6A Aggregate 2 (lane 11) refer to TrCel6A-K129E-S186T-A322D-Q363E-S413P and TrCel6A-K129E-S186T-A322D-Q363E-R410Q-S413P, respectively. TrCel6A purified from *Trichoderma* cellulase (lane 2) and molecular mass standards (lane 1) are shown for reference.

REFERENCES

Altschul et al. (1990) Basic local alignment search tool. *J. Mol. Biol.* 215:403-10

Berlin, A., Balakshin, M., Gilkes, N., Kadla, J., Maximenko, V., Kubo, S. and Saddler, J. (2005) Inhibition of cellulase, xylanase and beta-glucosidase activities by softwood lignin preparations. *Journal of Biotechnology*, 125(2): 198-209.

Berlin, A., Gilkes, N., Kurabi, A., Bura, R., Tu, Maobing, Kilburn, D. and Saddler, J. (2005) Weak Lignin-Binding Enzymes. *Applied Biochemistry and Biotechnology*, Spring (121-124):163-170.

Burton, J., Wood, S. G., Pedyczak, A. and Siemion, I. Z. (1989) Conformational preferences of sequential fragments of the hinge region of human IgA1 immunoglobulin molecule: II. *Biophysical Chemistry*, 33(1):39-45.

Bushuev, V. N., Gudkov, A. T., Liljas, A. and Sepetov, N. F. (1989) The flexible region of protein L12 from bacterial ribosomes studied by proton nuclear magnetic resonance. *Journal of Biological Chemistry*, 264(8):4498-4505.

Butler, T. and Alcalde, M. (2003) In Methods in Molecular Biology, vol. 231: (F. H. Arnold and G. Georgiou, editors), Humana Press Inc. Totowa (N.J.), pages 17-22.

Carrard, G. and Linder, M. (1999) Widely different off rates of two closely related cellulose-binding domains from *Trichoderma reesei*. *European Journal of Biochemistry*, 262(3):637-43.

Chernoglazov, V. M., Ermolova, O. V. and Klyosov, A. A. (1988) Adsorption of high-purity endo-1,4-beta-glucanases from *Trichoderma reesei* on components of lignocellulosic materials: Cellulose, lignin, and xylan, *Enzyme and Microbial Technology*, 10(8):503-507.

Davies, G. J., Brzozowski, A. M., Dauter, M., Varrot, A. and Schilein, M. (2000) Structure and function of *Humicola insolens* family 6 cellulases: structure of the endoglucanase, Cel6B, at 1.6 A resolution. *Biochemical Journal*, 348 Pt 1:201-207.

Eijsink, V. G., Gåseidnes, S., Borchert, T. V. and van den Burg, B. (2005) Directed evolution of enzyme stability. *Biomolecular Engineering*, 22(1-3):21-30.

Escoffier, G., Toussaint, B. and Vignon, M. R. (1991) Saccharification of steam-exploded poplarwood. *Biotechnology and Bioengineering*, 38(11):1308-1317.

Fagerstam, L. G., Pettersson, G. and Engstrom, J. A. (1984) The primary structure of a 1,4-β-glucan cellobiohydrolase from the fungus *Trichoderma reesei* QM 9414. *FEBS Letters*, 167:309-315.

Gietz, R. D. and Woods, R. A. (2002) Transformation of yeast by the Liac/ss carrier DNA/PEG method. *In Methods in Enzymology*, 350:87-96.

Gilkes, N. R., Henrissat, B., Kilburn, D. G., Miller, R. C. Jr. and Warren R. A. (1991) Domains in microbial beta-1,4-glycanases: sequence conservation, function, and enzyme families. *Microbiology Reviews*, 55(2):303-315.

Gilkes, N. R., Jervis, E., Henrissat, B., Tekant, B., Miller, R. C. Jr., Warren, R. A. and Kilburn, D. G. (1992) The adsorption of a bacterial cellulase and its two isolated domains to crystalline cellulose. *Journal of Biological Chemistry,* 267 (10):6743-6749.

Goto, M. (2007) Protein O-glycosylation in fungi: diverse structures and multiple functions. *Bioscience, Biotechnology and Biochemistry,* 71(6):1415-1427.

Holtzapple, M. T., Jun, J., Ashok, G., Patibanadala, S. L and Dale, B. E. (1991) The ammonia freeze explosion (AFEX) process: A practical lignocellulosic pretreatment. *Applied Biochemistry and Biotechnology,* 28/29:59-74.

Kaya, F., Heitmann, J. A. and Joyce, T. W. (2000) Influence of lignin and its degradation products on enzymatic hydrolysis of xylan. *Journal of Biotechnology,* 80(3):241-247.

Kong, F., Engler, C. R. and Soltes, E. J. (1992) Effects of cell-wall acetate, xylan backbone, and lignin on enzymatic hydrolysis of aspen. *Applied Biochemistry and Biotechnology,* 34/35:23-25.

Kraulis, J., Clore, G. M., Nilges, M., Jones, T. A., Pettersson, G., Knowles, J. and Gronenborn, A. M. (1989) Determination of the three-dimensional solution structure of the C-terminal domain of cellobiohydrolase I from *Trichoderma reesei.* A study using nuclear magnetic resonance and hybrid distance geometry-dynamical simulated annealing. *Biochemistry,* 28:7241-7257.

Linder, M., Mattinen, M. L., Kontteli, M., Lindeberg, G., Stahlberg, J., Drakenberg, T., Reinikainen, T., Pettersson, G. and Annila, A. (1995) Identification of functionally important amino acids in the cellulose-binding domain of *Trichoderma reesei* cellobiohydrolase I. *Protein Science,* 4(6):1056-1064.

Mattinen, M. L., Linder, M., Teleman, A. and Annila, A. (1997) Interaction between cellohexaose and cellulose binding domains from *Trichoderma reesei* cellulases. *FEBS Letters,* 407(3):291-296.

Meunier-Goddik, L. and Penner, M. H. (1999) Enzyme-catalyzed saccharification of model celluloses in the presence of lignacious residues. *Journal of Agricultural and Food Chemistry,* 47(1):346-351.

Mooney, C. A., Mansfield, S. D., Touhy, M. G. and Saddler, J. N. (1998) The effect of initial pore volume and lignin content on the enzymatic hydrolysis of softwoods. *Bioresource Technology,* 64:113-119.

Motulsky, H., and A. Christopoulos (2004) Fitting Models to Biological Data Using Linear and Nonlinear Regression: A Practical Guide to Curve Fitting. Oxford University Press, Inc., New York. 351 pp.

Palonen, H., Tjemeld, F., Zacchi, G. and Tenkanen, M. (2004) Adsorption of *Trichoderma reesei* CBH I and EG II and their catalytic domains on steam pretreated softwood and isolated lignin. *Journal of Biotechnology,* 107:65-72.

Piyachomkwan, K., Gable, K. P. and Penner, M. H. (1997) p-Aminophenyl 1-thio-beta-D-cellobioside: Synthesis and application in affinity chromatography of exo-type cellulases. *Carbohydrate Research,* 303:255-259.

Reinikainen, T., Ruohonen, L., Nevanen, T., Laaksonen, L., Kraulis, P., Jones, T. A., Knowles, J. K. and Teeri, T. T. (1992) Investigation of the function of mutated cellulose-binding domains of *Trichoderma reesei* cellobiohydrolase I. *Proteins,* 14(4):475-482.

Rouvinen, J et al. (1990) Three-dimensional structure of cellobiohydrolase II from *Trichoderma reesei. Science,* 249 (4967):380-386.

Spezio, M, Wilson, D. B. and Karplus, P. A. (1993) Crystal structure of the catalytic domain of a thermophilic endocellulase. *Biochemistry,* 32(38):9906-9916.

Srisodsuk, M., Reinikainen, T., Penttila, M. and Teeri, T. T. (1993) Role of the interdomain linker peptide of *Trichoderma reesei* cellobiohydrolase I in its interaction with crystalline cellulose. *Journal of Biological Chemistry,* 268 (28):20756-20761.

Srisodsuk, M., Lehtio, J., Linder, M., Margolles-Clark, E., Reinikainen, T. and Teeri, T. T. (1997) *Trichoderma reesei* cellobiohydrolase I with an endoglucanase cellulose-binding domain: action on bacterial microcrystalline cellulose. *Journal of Biotechnology,* 57(1-3):49-57.

Tomme, P., Van Tilbeurgh, H., Pettersson, G., Van Damme, J., Vandekerckhove, J., Knowles, J., Teeri, T. and Claeyssens, M. (1988) Studies of the cellulolytic system of *Trichoderma reesei* QM 9414. Analysis of domain function in two cellobiohydrolases by limited proteolysis. *European Journal of Biochemistry,* 170(3):575-581.

Trinder, P. (1969) Determination of glucose in blood using glucose oxidase with an alternative oxygen accepter. *Annals of Clinical Biochemistry,* 6:24-27.

Tu, M., Chandra, R. P. and Saddler, J. N. (2007) Evaluating the distribution of cellulases and the recycling of free cellulases during the hydrolysis of lignocellulosic substrates. *Biotechnology Progress,* 23(2):398-406.

Varrot, A, Schilein, M and Davies, G. J. (1999) Structural changes of the active site tunnel of *Humicola insolens* cellobiohydrolase, Cel6A, upon oligosaccharide binding. *Biochemistry,* 38(28):8884-8891.

Varrot, A., Leydier, S., Pell, G., Macdonald, J. M., Stick, R. V., Henrissat, B., Gilbert, H. J. and Davies, G. J. (2005) strains possess functional cellulases. *Journal of Biological Chemistry,* 280(21):20181-20184.

Viikari, L., Alapuranen, M., Puranen, T., Vehmaanperä, J. and Siika-Aho, M. (2007) Thermostable enzymes in lignocellulose hydrolysis. *Advances in Biochemical Engineering/Biotechnology,* 108:121-145.

Weil, J., Sarikaya, A., Rau, S., Goetz, J, Ladisch, C., Brewer, M., Hendrickson, R. and Ladisch, M. (1997) Preteatment of yellow poplar sawdust by pressure cooking in water. *Applied Biochemistry and Biotechnology,* 68(1-2):21-40.

Yang, B. and Wyman, C. E. (2006) BSA treatment to enhance enzymatic hydrolysis of cellulose in lignin containing substrates. *Biotechnology and Bioengineering,* 94(4):61

The embodiments of the invention in which an exclusive property or privilege is claimed are defined as follows:

1. An isolated modified *Trichoderma reesei* Family 6 (TrCel6A) cellulase comprising one or more amino acid substitutions selected from the group consisting of:
   substitution of a basic amino acid at position 129 by a charge-neutral or an acidic amino acid;
   substitution of a charge neutral amino acid at one or more of positions 322 and 363 by an acidic amino acid; and
   substitution of an amino acid at position 186 by a threonine;
   wherein amino acids 83-447 of the modified TrCel6A are from about 90% to about 99% identical to amino acids 83-447 of SEQ ID NO: 1 and wherein the modified TrCel6A cellulase exhibits at least a 15% reduction in the extent of deactivation by lignin relative to that of a parental TrCel6A cellulase.

2. The modified TrCel6A cellulase of claim 1, wherein amino acids 83-447 of the modified TrCel6A cellulase are from about 95% to about 99.9% identical to amino acids 83-447 of SEQ ID NO: 1.

3. The modified TrCel6A cellulase of claim 1, wherein the amino acid substitutions are selected from the group consisting of K129E, S186T, A322D and Q363E.

4. The modified TrCel6A cellulase of claim 1, further comprising one or more amino acid substitutions selected from the group consisting of Y103H, Y103K, Y103R, Y103A, Y103V, Y103L, Y103P, L136V, L136I, R410G, R410Q and S413P.

5. An isolated genetic construct comprising a nucleic acid sequence encoding the modified TrCel6A cellulase of claim 1.

6. An isolated genetically modified microbe comprising the genetic construct of claim 5.

7. The isolated genetically modified microbe of claim 6, wherein the microbe is a yeast or filamentous fungus.

8. The isolated genetically modified microbe of claim 7, wherein the microbe is *Saccharomyces cerevisiae* or *Trichoderma reesei*.

9. A process for producing a modified TrCel6A cellulase comprising the steps of growing the genetically modified microbe of claim 6 in a culture medium under conditions that induce expression and secretion of the modified TrCel6A cellulase, and recovering the modified TrCel6A cellulase from the culture medium.

10. A process for hydrolyzing a cellulose substrate, comprising the steps of contacting the substrate with the modified TrCel6A cellulase of claim 1 in the presence of lignin.

11. The process of claim 10, wherein the cellulose substrate is a pretreated lignocellulosic feedstock and wherein the enzymatic hydrolysis produces fermentable sugars.

12. The process of claim 11, wherein the pretreated lignocellulose feedstock is selected from the group consisting of corn stover, wheat straw, barley straw, rice straw, oat straw, canola straw, soybean stover, corn fiber, sugar beet pulp, pulp mill fines and rejects, sugar cane bagasse, hardwood, softwood, sawdust, switch grass, miscanthus, cord grass and reed canary grass.

13. A process for producing a modified TrCel6A cellulase, comprising the steps of:
   (i) transforming fungal host cells with a genetic construct as defined in claim 6 to produce recombinant fungal strains;
   (ii) selecting the recombinant fungal strains expressing the modified TrCel6A cellulase; and
   (iii) culturing the recombinant fungal strains selected in step (ii) in submerged liquid fermentations under conditions that induce expression of the modified TrCel6A cellulase.

14. An isolated Family 6 TrCel6A cellulase comprising SEQ ID NO: 43.

15. An isolated Family 6 TrCel6A cellulase consisting SEQ ID NO: 43.

* * * * *

UNITED STATES PATENT AND TRADEMARK OFFICE
CERTIFICATE OF CORRECTION

| | |
|---|---|
| PATENT NO. | : 8,110,389 B2 |
| APPLICATION NO. | : 12/512403 |
| DATED | : February 7, 2012 |
| INVENTOR(S) | : James A. Lavigne et al. |

It is certified that error appears in the above-identified patent and that said Letters Patent is hereby corrected as shown below:

ON THE TITLE PAGE ITEM [56] REFERENCES CITED:

Other Publications, "Sen et al., --- 212-223.*" should begin a new line;
under Birren, et al., "NCBIIXP_001210279 (2008)." should read
--NCBIXP_001210279 (2008).--;
under Birren, et al., "okayamam" should be italicized;
under Davies, et al., "Humicola insolens" should be italicized; and
under Varrot, et al., "Humicola insolens" should be italicized.

ON THE TITLE PAGE AT (ITEM) PRIMARY EXAMINER

"Ganapathirama" should read --Ganapathiram--.

ON THE TITLE PAGET ITEM [57] ABSTRACT:

Line 7, "display" should read --displays--.

COLUMN 2:

Line 33, "has" should read --have--.

COLUMN 3:

Line 28, "acid" should read --acids--.

COLUMN 6:

Line 46, "encoding for" should read --encoding--.

Signed and Sealed this
Fifteenth Day of May, 2012

David J. Kappos
*Director of the United States Patent and Trademark Office*

CERTIFICATE OF CORRECTION (continued)
U.S. Pat. No. 8,110,389 B2

COLUMN 8:

Line 62, "is" should read --are--.

COLUMN 18:

Line 38, "were" should read --was--.

COLUMN 23:

Line 44, "S 186T" should read --S186T--.

COLUMN 28:

Line 54, "94(4):61" should read --94(4):61.--.

COLUMN 121:

Line 59, "99%" should read --99.9%--.

COLUMN 124:

Line 14, "consisting" should read --consisting of--.

SEQUENCE LISTING

<160> NUMBER OF SEQ ID NOS: 58

<210> SEQ ID NO 1
<211> LENGTH: 447
<212> TYPE: PRT
<213> ORGANISM: Trichoderma reesei

<400> SEQUENCE: 1

```
Gln Ala Cys Ser Ser Val Trp Gly Gln Cys Gly Gly Gln Asn Trp Ser
1               5                   10                  15
Gly Pro Thr Cys Cys Ala Ser Gly Ser Thr Cys Val Tyr Ser Asn Asp
            20                  25                  30
Tyr Tyr Ser Gln Cys Leu Pro Gly Ala Ser Ser Ser Ser Ser Ser Thr
            35                  40                  45
Arg Ala Ala Ser Thr Thr Ser Arg Val Ser Pro Thr Thr Ser Arg Ser
50                  55                  60
Ser Ser Ala Thr Pro Pro Gly Ser Thr Thr Thr Arg Val Pro Pro
65              70                  75                  80
Val Gly Ser Gly Thr Ala Thr Tyr Ser Gly Asn Pro Phe Val Gly Val
                85                  90                  95
Thr Pro Trp Ala Asn Ala Tyr Tyr Ala Ser Glu Val Ser Ser Leu Ala
            100                 105                 110
Ile Pro Ser Leu Thr Gly Ala Met Ala Thr Ala Ala Ala Val Ala
            115                 120                 125
Lys Val Pro Ser Phe Met Trp Leu Asp Thr Leu Asp Lys Thr Pro Leu
        130                 135                 140
Met Glu Gln Thr Leu Ala Asp Ile Arg Thr Ala Asn Lys Asn Gly Gly
145                 150                 155                 160
Asn Tyr Ala Gly Gln Phe Val Val Tyr Asp Leu Pro Asp Arg Asp Cys
                165                 170                 175
Ala Ala Leu Ala Ser Asn Gly Glu Tyr Ser Ile Ala Asp Gly Gly Val
            180                 185                 190
Ala Lys Tyr Lys Asn Tyr Ile Asp Thr Ile Arg Gln Ile Val Val Glu
        195                 200                 205
Tyr Ser Asp Ile Arg Thr Leu Leu Val Ile Glu Pro Asp Ser Leu Ala
210                 215                 220
Asn Leu Val Thr Asn Leu Gly Thr Pro Lys Cys Ala Asn Ala Gln Ser
225                 230                 235                 240
Ala Tyr Leu Glu Cys Ile Asn Tyr Ala Val Thr Gln Leu Asn Leu Pro
                245                 250                 255
Asn Val Ala Met Tyr Leu Asp Ala Gly His Ala Gly Trp Leu Gly Trp
            260                 265                 270
Pro Ala Asn Gln Asp Pro Ala Ala Gln Leu Phe Ala Asn Val Tyr Lys
            275                 280                 285
Asn Ala Ser Ser Pro Arg Ala Leu Arg Gly Leu Ala Thr Asn Val Ala
        290                 295                 300
Asn Tyr Asn Gly Trp Asn Ile Thr Ser Pro Pro Ser Tyr Thr Gln Gly
305                 310                 315                 320
Asn Ala Val Tyr Asn Glu Lys Leu Tyr Ile His Ala Ile Gly Pro Leu
                325                 330                 335
Leu Ala Asn His Gly Trp Ser Asn Ala Phe Phe Ile Thr Asp Gln Gly
            340                 345                 350
Arg Ser Gly Lys Gln Pro Thr Gly Gln Gln Gln Trp Gly Asp Trp Cys
        355                 360                 365
Asn Val Ile Gly Thr Gly Phe Gly Ile Arg Pro Ser Ala Asn Thr Gly
        370                 375                 380
Asp Ser Leu Leu Asp Ser Phe Val Trp Val Lys Pro Gly Gly Glu Cys
385                 390                 395                 400
Asp Gly Thr Ser Asp Ser Ser Ala Pro Arg Phe Asp Ser His Cys Ala
            405                 410                 415
Leu Pro Asp Ala Leu Gln Pro Ala Pro Gln Ala Gly Ala Trp Phe Gln
            420                 425                 430
```

-continued

Ala Tyr Phe Val Gln Leu Leu Thr Asn Ala Asn Pro Ser Phe Leu
        435                 440                 445

<210> SEQ ID NO 2
<211> LENGTH: 362
<212> TYPE: PRT
<213> ORGANISM: Hypocrea koningii

<400> SEQUENCE: 2

Ala Thr Tyr Ser Gly Asn Pro Phe Val Gly Val Thr Pro Trp Ala Asn
1               5                   10                  15

Ala Tyr Tyr Ala Ser Glu Val Ser Leu Ala Ile Pro Ser Leu
            20                  25                  30      Thr

Gly Ala Met Ala Thr Ala Ala Ala Val Ala Lys Val Pro Ser Phe
            35                  40                  45

Met Trp Leu Asp Thr Leu Asp Lys Thr Pro Leu Met Glu Gln Thr Leu
    50                  55                  60

Ala Asp Ile Arg Thr Ala Asn Lys Asn Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Ala Lys Tyr Lys Asn
            100                 105                 110

Tyr Ile Asp Thr Ile Arg Gln Ile Val Val Glu Tyr Ser Asp Ile Arg
        115                 120                 125

Thr Leu Leu Val Ile Glu Pro Asp Ser Leu Ala Asn Leu Val Thr Asn
130                 135                 140

Leu Gly Thr Pro Lys Cys Ala Asn Ala Gln Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Gly Trp
    210                 215                 220

Asn Ile Thr Ser Pro Pro Ser Tyr Thr Gln Gly Asn Ala Val Tyr Asn
225                 230                 235                 240

Glu Lys Leu Tyr Ile His Ala Ile Gly Arg Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
        275                 280                 285

Gly Phe Gly Ile Arg Pro Ser Ala Asn Thr Gly Asp Ser Leu Leu Asp
    290                 295                 300

Ser Phe Val Trp Val Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
        355                 360

<210> SEQ ID NO 3
<211> LENGTH: 362
<212> TYPE: PRT
<213> ORGANISM: Trichoderma viride CICC 13038

<400> SEQUENCE: 3

```
Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
            20                  25                  30

Gly Ala Met Ala Thr Ala Ala Ala Val Ala Lys Val Pro Ser Phe
        35                  40                  45

Met Trp Leu Asp Thr Leu Asp Lys Thr Pro Leu Met Glu Gln Thr Leu
50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Ala Lys Tyr Lys Asn
            100                 105                 110

Tyr Ile Asp Thr Ile Arg Gln Ile Val Val Glu Tyr Ser Asp Ile Arg
        115                 120                 125

Thr Leu Leu Val Ile Glu Pro Asp Ser Leu Ala Asn Leu Val Thr Asn
130                 135                 140

Leu Gly Thr Pro Lys Cys Ala Asn Ala Pro Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Gly Trp
210                 215                 220

Asn Ile Thr Ser Pro Pro Ser Tyr Thr Gln Gly Asn Ala Val Tyr Asn
225                 230                 235                 240

Glu Lys Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
        275                 280                 285

Gly Phe Gly Ile Arg Pro Ser Ala Asn Thr Gly Asp Ser Leu Leu Asp
290                 295                 300

Ser Phe Val Trp Val Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
        355                 360
```

<210> SEQ ID NO 4

<211> LENGTH: 362
<212> TYPE: PRT
<213> ORGANISM: Hypocrea koningii 3.2774

<400> SEQUENCE: 4

```
Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
            20                  25                  30

Gly Ala Met Ala Thr Ala Ala Ala Val Ala Lys Val Pro Ser Phe
        35                  40                  45

Met Trp Leu Asp Thr Phe Asp Lys Thr Pro Leu Met Glu Gln Thr Leu
50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Asp Lys Tyr Lys Asn
            100                 105                 110

Tyr Ile Asp Thr Ile Arg Gln Ile Val Val Glu Tyr Ser Asp Ile Arg
        115                 120                 125

Thr Leu Leu Val Ile Glu Pro Asp Ser Leu Ala Asn Leu Val Thr Asn
130                 135                 140

Leu Gly Thr Pro Lys Cys Ala Asn Ala Gln Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Gly Trp
210                 215                 220

Asn Ile Thr Ser Pro Pro Ser Tyr Thr Gln Gly Asn Ala Val Tyr Asn
225                 230                 235                 240

Glu Gln Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
        275                 280                 285

Gly Phe Gly Ile Arg Pro Ser Ala Asn Thr Gly Asp Ser Leu Leu Asp
290                 295                 300

Ser Phe Val Trp Ile Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
        355                 360
```

<210> SEQ ID NO 5
<211> LENGTH: 362
<212> TYPE: PRT
<213> ORGANISM: Hypocrea koningii AS3.2774

<400> SEQUENCE: 5

```
Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
            20                  25                  30

Gly Ala Met Ala Thr Ala Ala Ala Val Ala Lys Val Pro Ser Ser
        35                  40                  45

Met Trp Leu Asp Thr Phe Asp Lys Thr Pro Leu Met Glu Gln Thr Leu
    50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Val Asp Lys Tyr Lys Asn
            100                 105                 110

Tyr Ile Asp Thr Ile Arg Gln Ile Val Val Glu Tyr Ser Asp Ile Arg
                115                 120                 125

Thr Leu Leu Val Ile Glu Pro Asp Ser Leu Ala Asn Leu Val Thr Asn
    130                 135                 140

Leu Gly Thr Pro Lys Cys Ala Asn Ala Gln Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Gly Trp
210                 215                 220

Asn Ile Thr Ser Pro Pro Ser Tyr Thr Gln Gly Asn Ala Val Tyr Asn
225                 230                 235                 240

Glu Gln Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
        275                 280                 285

Gly Phe Gly Ile Arg Pro Ser Ala Asn Thr Gly Asp Ser Leu Leu Asp
290                 295                 300

Ser Phe Val Trp Ile Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
        355                 360
```

<210> SEQ ID NO 6
<211> LENGTH: 362
<212> TYPE: PRT
<213> ORGANISM: Trichoderma parceramosum

<400> SEQUENCE: 6

```
Ala Thr Tyr Ser Gly Asn Pro Phe Val Gly Val Thr Pro Trp Ala Asn
 1               5                   10                  15

Ala Tyr Tyr Ala Ser Glu Val Ser Ser Leu Ala Ile Pro Ser Leu Thr
                20                  25                  30

Gly Ala Met Ala Thr Ala Ala Ala Val Ala Lys Val Pro Ser Phe
            35                  40                  45

Met Trp Leu Asp Thr Leu Asp Lys Thr Pro Leu Met Glu Gln Thr Leu
    50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Ala Lys Tyr Lys Asn
                100                 105                 110

Tyr Ile Asp Thr Ile Arg Gln Ile Val Val Glu Tyr Ser Asp Ile Arg
                115                 120                 125

Thr Ile Leu Val Ile Glu Pro Asp Ser Leu Ala Asn Leu Val Thr Asn
    130                 135                 140

Leu Gly Thr Pro Lys Cys Ala Asn Ala Gln Ser Ala Tyr Leu Glu Cys
145                 150                 155                 160

Ile Asn Tyr Ala Ile Thr Gln Leu Asn Leu Pro Asn Ile Ala Met Tyr
                165                 170                 175

Leu Asp Ala Gly His Ala Gly Trp Leu Gly Trp Pro Ala Asn Gln Asp
                180                 185                 190

Pro Ala Ala Gln Leu Phe Ala Asn Val Tyr Lys Asn Ala Ser Ser Pro
                195                 200                 205

Ser Ala Leu Arg Gly Leu Ala Thr Asn Val Ala Asn Tyr Asn Gly Trp
210                 215                 220

Asn Ile Thr Ser Pro Pro Ser Tyr Thr Gln Gly Asn Ala Val Tyr Asn
225                 230                 235                 240

Glu Lys Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
                260                 265                 270

Pro Thr Gly Gln Gln Gln Trp Gly Asp Trp Cys Asn Val Ile Gly Thr
                275                 280                 285

Gly Phe Gly Ile Arg Pro Ser Ser Asn Thr Gly Asp Ser Leu Leu Asp
                290                 295                 300

Ser Phe Val Trp Val Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
                340                 345                 350

Leu Leu Thr Asn Ala Asn Pro Ser Phe Leu
                355                 360

<210> SEQ ID NO 7
<211> LENGTH: 365
<212> TYPE: PRT
<213> ORGANISM: Aspergillus nidulans FGSC A4

<400> SEQUENCE: 7

Ala Thr Ala Ser Gly Asn Pro Phe Ser Gly Tyr Gln Leu Tyr Val Asn
 1               5                   10                  15
```

```
Pro Tyr Tyr Ser Ser Glu Val Gln Ser Ile Ala Ile Pro Ser Leu Thr
            20                  25                  30

Gly Thr Leu Ser Ser Leu Ala Pro Ala Ala Thr Ala Ala Ala Lys Val
        35                  40                  45

Pro Ser Phe Val Trp Leu Asp Val Ala Ala Lys Val Pro Thr Met Ala
 50                  55                  60

Thr Tyr Leu Ala Asp Ile Arg Ser Gln Asn Ala Ala Gly Ala Asn Pro
 65                  70                  75                  80

Pro Ile Ala Gly Gln Phe Val Val Tyr Asp Leu Pro Asp Arg Asp Cys
                 85                  90                  95

Ala Ala Leu Ala Ser Asn Gly Glu Phe Ala Ile Ser Asp Gly Gly Val
            100                 105                 110

Gln His Tyr Lys Asp Tyr Ile Asp Ser Ile Arg Glu Ile Leu Val Glu
        115                 120                 125

Tyr Ser Asp Val His Val Ile Leu Val Ile Glu Pro Asp Ser Leu Ala
130                 135                 140

Asn Leu Val Thr Asn Leu Asn Val Ala Lys Cys Ala Asn Ala Gln Ser
145                 150                 155                 160

Ala Tyr Leu Glu Cys Thr Asn Tyr Ala Val Thr Gln Leu Asn Leu Pro
                165                 170                 175

Asn Val Ala Met Tyr Leu Asp Ala Gly His Ala Gly Trp Leu Gly Trp
            180                 185                 190

Pro Ala Asn Leu Gln Pro Ala Ala Asn Leu Tyr Ala Gly Val Tyr Ser
        195                 200                 205

Asp Ala Gly Ser Pro Ala Ala Leu Arg Gly Leu Ala Thr Asn Val Ala
210                 215                 220

Asn Tyr Asn Ala Trp Ala Ile Asp Thr Cys Pro Ser Tyr Thr Gln Gly
225                 230                 235                 240

Asn Ser Val Cys Asp Glu Lys Asp Tyr Ile Asn Ala Leu Ala Pro Leu
                245                 250                 255

Leu Arg Ala Gln Gly Phe Asp Ala His Phe Ile Thr Asp Thr Gly Arg
            260                 265                 270

Asn Gly Lys Gln Pro Thr Gly Gln Gln Ala Trp Gly Asp Trp Cys Asn
        275                 280                 285

Val Ile Gly Thr Gly Phe Gly Ala Arg Pro Ser Thr Asn Thr Gly Asp
290                 295                 300

Ser Leu Leu Asp Ala Phe Val Trp Val Lys Pro Gly Gly Glu Ser Asp
305                 310                 315                 320

Gly Thr Ser Asp Thr Ser Ala Ala Arg Tyr Asp Ala His Cys Gly Tyr
                325                 330                 335

Ser Asp Ala Leu Gln Pro Ala Pro Glu Ala Gly Thr Trp Phe Gln Ala
            340                 345                 350

Tyr Phe Val Gln Leu Leu Gln Asn Ala Asn Pro Ser Phe
        355                 360                 365

<210> SEQ ID NO 8
<211> LENGTH: 365
<212> TYPE: PRT
<213> ORGANISM: Aspergillus niger CBS 513.88

<400> SEQUENCE: 8

Ala Ser Ala Ser Gly Asn Pro Phe Ser Gly Tyr Gln Leu Tyr Val Asn
 1               5                  10                  15

Pro Tyr Tyr Ser Ser Glu Val Ala Ser Leu Ala Ile Pro Ser Leu Thr
            20                  25                  30
```

Gly Ser Leu Ser Ser Leu Gln Ala Ala Thr Ala Ala Ala Lys Val
            35                  40                  45

Pro Ser Phe Val Trp Leu Asp Thr Ala Ala Lys Val Pro Thr Met Gly
 50                  55                  60

Asp Tyr Leu Ala Asp Ile Gln Ser Gln Asn Ala Ala Gly Ala Asn Pro
 65                  70                  75                  80

Pro Ile Ala Gly Gln Phe Val Val Tyr Asp Leu Pro Asp Arg Asp Cys
                 85                  90                  95

Ala Ala Leu Ala Ser Asn Gly Glu Tyr Ser Ile Ala Asp Asn Gly Val
            100                 105                 110

Glu His Tyr Lys Ser Tyr Ile Asp Ser Ile Arg Glu Ile Leu Val Gln
            115                 120                 125

Tyr Ser Asp Val His Thr Leu Leu Val Ile Glu Pro Asp Ser Leu Ala
130                 135                 140

Asn Leu Val Thr Asn Leu Asn Val Ala Lys Cys Ala Asn Ala Glu Ser
145                 150                 155                 160

Ala Tyr Leu Glu Cys Thr Asn Tyr Ala Leu Thr Gln Leu Asn Leu Pro
                165                 170                 175

Asn Val Ala Met Tyr Leu Asp Ala Gly His Ala Gly Trp Leu Gly Trp
            180                 185                 190

Pro Ala Asn Gln Gln Pro Ala Ala Asp Leu Phe Ala Ser Val Tyr Lys
            195                 200                 205

Asn Ala Ser Ser Pro Ala Ala Val Arg Gly Leu Ala Thr Asn Val Ala
            210                 215                 220

Asn Tyr Asn Ala Trp Thr Ile Ser Ser Cys Pro Ser Tyr Thr Gln Gly
225                 230                 235                 240

Asn Ser Val Cys Asp Glu Gln Gln Tyr Ile Asn Ala Ile Ala Pro Leu
                245                 250                 255

Leu Gln Ala Gln Gly Phe Asp Ala His Phe Ile Val Asp Thr Gly Arg
            260                 265                 270

Asn Gly Lys Gln Pro Thr Gly Gln Gln Ala Trp Gly Asp Trp Cys Asn
            275                 280                 285

Val Ile Asn Thr Gly Phe Gly Glu Arg Pro Thr Thr Asp Thr Gly Asp
290                 295                 300

Ala Leu Val Asp Ala Phe Val Trp Val Lys Pro Gly Gly Glu Ser Asp
305                 310                 315                 320

Gly Thr Ser Asp Ser Ser Ala Thr Arg Tyr Asp Ala His Cys Gly Tyr
                325                 330                 335

Ser Asp Ala Leu Gln Pro Ala Pro Glu Ala Gly Thr Trp Phe Gln Ala
            340                 345                 350

Tyr Phe Val Gln Leu Leu Thr Asn Ala Asn Pro Ala Phe
            355                 360                 365

<210> SEQ ID NO 9
<211> LENGTH: 362
<212> TYPE: PRT
<213> ORGANISM: Aspergillus oryzae RIB 40

<400> SEQUENCE: 9

Ala Thr Ala Gly Gly Asn Pro Phe Glu Gly Tyr Asp Leu Tyr Val Asn
 1               5                  10                  15

Pro Tyr Tyr Lys Ser Glu Val Glu Ser Leu Ala Ile Pro Ser Met Thr
                 20                  25                  30

Gly Ser Leu Ala Glu Lys Ala Ser Ala Ala Asn Val Pro Ser Phe
            35                  40                  45

-continued

His Trp Leu Asp Thr Thr Asp Lys Val Pro Gln Met Gly Glu Phe Leu
    50                  55                  60

Glu Asp Ile Lys Thr Lys Asn Ala Ala Gly Ala Asn Pro Pro Thr Ala
65                  70                  75                  80

Gly Ile Phe Val Val Tyr Asp Leu Pro Asp Arg Asp Cys Ala Ala Leu
                85                  90                  95

Ala Ser Asn Gly Glu Phe Leu Ile Ser Asp Gly Val Glu Lys Tyr
            100                 105                 110

Lys Ala Tyr Ile Asp Ser Ile Arg Glu Gln Val Glu Lys Tyr Ser Asp
            115                 120                 125

Thr Gln Ile Ile Leu Val Ile Glu Pro Asp Ser Leu Ala Asn Leu Val
    130                 135                 140

Thr Asn Leu Asn Val Gln Lys Cys Ala Asn Ala Gln Asp Ala Tyr Leu
145                 150                 155                 160

Glu Cys Thr Asn Tyr Ala Leu Thr Gln Leu Asn Leu Pro Asn Val Ala
                165                 170                 175

Met Tyr Leu Asp Ala Gly His Ala Gly Trp Leu Gly Trp Pro Ala Asn
            180                 185                 190

Ile Gly Pro Ala Ala Glu Leu Tyr Ala Ser Val Tyr Lys Asn Ala Ser
            195                 200                 205

Ser Pro Ala Ala Val Arg Gly Leu Ala Thr Asn Val Ala Asn Tyr Asn
    210                 215                 220

Ala Phe Ser Ile Asp Ser Cys Pro Ser Tyr Thr Gln Gly Ser Thr Val
225                 230                 235                 240

Cys Asp Glu Lys Thr Tyr Ile Asn Asn Phe Ala Pro Gln Leu Lys Ser
                245                 250                 255

Ala Gly Phe Asp Ala His Phe Ile Val Asp Thr Gly Arg Asn Gly Asn
            260                 265                 270

Gln Pro Thr Gly Gln Ser Gln Trp Gly Asp Trp Cys Asn Val Lys Asn
    275                 280                 285

Thr Gly Phe Gly Val Arg Pro Thr Thr Asp Thr Gly Asp Glu Leu Val
    290                 295                 300

Asp Ala Phe Val Trp Val Lys Pro Gly Gly Glu Ser Asp Gly Thr Ser
305                 310                 315                 320

Asp Thr Ser Ala Glu Arg Tyr Asp Ala His Cys Gly Tyr Ala Asp Ala
                325                 330                 335

Leu Thr Pro Ala Pro Glu Ala Gly Thr Trp Phe Gln Ala Tyr Phe Glu
            340                 345                 350

Gln Leu Val Glu Asn Ala Asn Pro Ser Leu
    355                 360

<210> SEQ ID NO 10
<211> LENGTH: 363
<212> TYPE: PRT
<213> ORGANISM: Aspergillus niger CBS 513.88

<400> SEQUENCE: 10

Ala Ser Ala Thr Gly Asn Pro Phe Glu Gly Tyr Gln Leu Tyr Ala Asn
1               5                   10                  15

Pro Tyr Tyr Lys Ser Gln Val Glu Ser Ser Ala Ile Pro Ser Leu Ser
                20                  25                  30

Ala Ser Ser Leu Val Ala Gln Ala Ser Ala Ala Asp Val Pro Ser
            35                  40                  45

Phe Tyr Trp Leu Asp Thr Ala Asp Lys Val Pro Thr Met Gly Glu Tyr
    50                  55                  60

```
Leu Glu Asp Ile Gln Thr Gln Asn Ala Ala Gly Ala Ser Pro Pro Ile
 65                  70                  75                  80

Ala Gly Ile Phe Val Val Tyr Asp Leu Pro Asp Arg Asp Cys Ser Ala
                 85                  90                  95

Leu Ala Ser Asn Gly Glu Tyr Ser Ile Ser Asp Gly Gly Val Glu Lys
            100                 105                 110

Tyr Lys Ala Tyr Ile Asp Ser Ile Arg Glu Gln Val Glu Thr Tyr Ser
        115                 120                 125

Asp Val Gln Thr Ile Leu Ile Ile Glu Pro Asp Ser Leu Ala Asn Leu
    130                 135                 140

Val Thr Asn Leu Asp Val Ala Lys Cys Ala Asn Ala Glu Ser Ala Tyr
145                 150                 155                 160

Leu Glu Cys Thr Asn Tyr Ala Leu Glu Gln Leu Asn Leu Pro Asn Val
                165                 170                 175

Ala Met Tyr Leu Asp Ala Gly His Ala Gly Trp Leu Gly Trp Pro Ala
            180                 185                 190

Asn Ile Gly Pro Ala Ala Gln Leu Tyr Ala Ser Val Tyr Lys Asn Ala
        195                 200                 205

Ser Ser Pro Ala Ala Val Arg Gly Leu Ala Thr Asn Val Ala Asn Phe
210                 215                 220

Asn Ala Trp Ser Ile Asp Ser Cys Pro Ser Tyr Thr Ser Gly Asn Asp
225                 230                 235                 240

Val Cys Asp Glu Lys Ser Tyr Ile Asn Ala Ile Ala Pro Glu Leu Ser
                245                 250                 255

Ser Ala Gly Phe Asp Ala His Phe Ile Thr Asp Thr Gly Arg Asn Gly
            260                 265                 270

Lys Gln Pro Thr Gly Gln Ser Ala Trp Gly Asp Trp Cys Asn Val Lys
        275                 280                 285

Asp Thr Gly Phe Gly Ala Gln Pro Thr Thr Thr Gly Asp Glu Leu
    290                 295                 300

Ala Asp Ala Phe Val Trp Val Lys Pro Gly Gly Glu Ser Asp Gly Thr
305                 310                 315                 320

Ser Asp Thr Ser Ser Arg Tyr Asp Ala His Cys Gly Tyr Ser Asp
                325                 330                 335

Ala Leu Gln Pro Ala Pro Glu Ala Gly Thr Trp Phe Gln Ala Tyr Phe
            340                 345                 350

Glu Gln Leu Leu Thr Asn Ala Asn Pro Ser Leu
        355                 360

<210> SEQ ID NO 11
<211> LENGTH: 364
<212> TYPE: PRT
<213> ORGANISM: Acremonium cellulolyticus Y-94

<400> SEQUENCE: 11

Ala Ala Ala Ser Gly Asn Pro Phe Ser Gly Tyr Gln Leu Tyr Ala Asn
 1               5                  10                  15

Pro Tyr Tyr Ser Ser Glu Val His Thr Leu Ala Ile Pro Ser Leu Thr
             20                  25                  30

Gly Ser Leu Ala Ala Ala Ala Thr Lys Ala Ala Glu Ile Pro Ser Phe
         35                  40                  45

Val Trp Leu Asp Thr Ala Ala Lys Val Pro Thr Met Gly Thr Tyr Leu
     50                  55                  60

Ala Asn Ile Glu Ala Ala Asn Lys Ala Gly Ala Ser Pro Pro Ile Ala
 65                  70                  75                  80
```

```
Gly Ile Phe Val Val Tyr Asp Leu Pro Asp Arg Asp Cys Ala Ala Ala
                85                  90                  95

Ala Ser Asn Gly Glu Tyr Thr Val Ala Asn Asn Gly Val Ala Asn Tyr
            100                 105                 110

Lys Ala Tyr Ile Asp Ser Ile Val Ala Gln Leu Lys Ala Tyr Pro Asp
        115                 120                 125

Val His Thr Ile Leu Ile Ile Glu Pro Asp Ser Leu Ala Asn Met Val
    130                 135                 140

Thr Asn Leu Ser Thr Ala Lys Cys Ala Glu Ala Gln Ser Ala Tyr Tyr
145                 150                 155                 160

Glu Cys Val Asn Tyr Ala Leu Ile Asn Leu Asn Leu Ala Asn Val Ala
                165                 170                 175

Met Tyr Ile Asp Ala Gly His Ala Gly Trp Leu Gly Trp Ser Ala Asn
            180                 185                 190

Leu Ser Pro Ala Ala Gln Leu Phe Ala Thr Val Tyr Lys Asn Ala Ser
        195                 200                 205

Ala Pro Ala Ser Leu Arg Gly Leu Ala Thr Asn Val Ala Asn Tyr Asn
    210                 215                 220

Ala Trp Ser Ile Ser Ser Pro Ser Tyr Thr Ser Gly Asp Ser Asn
225                 230                 235                 240

Tyr Asp Glu Lys Leu Tyr Ile Asn Ala Leu Ser Pro Leu Leu Thr Ser
                245                 250                 255

Asn Gly Trp Pro Asn Ala His Phe Ile Met Asp Thr Ser Arg Asn Gly
            260                 265                 270

Val Gln Pro Thr Lys Gln Ala Trp Gly Asp Trp Cys Asn Val Ile
        275                 280                 285

Gly Thr Gly Phe Gly Val Gln Pro Thr Thr Asn Thr Gly Asp Pro Leu
    290                 295                 300

Glu Asp Ala Phe Val Trp Val Lys Pro Gly Gly Glu Ser Asp Gly Thr
305                 310                 315                 320

Ser Asn Ser Ser Ala Thr Arg Tyr Asp Phe His Cys Gly Tyr Ser Asp
                325                 330                 335

Ala Leu Gln Pro Ala Pro Glu Ala Gly Thr Trp Phe Gln Ala Tyr Phe
            340                 345                 350

Val Gln Leu Leu Thr Asn Ala Asn Pro Ala Leu Val
        355                 360

<210> SEQ ID NO 12
<211> LENGTH: 362
<212> TYPE: PRT
<213> ORGANISM: Talaromyces emersonii

<400> SEQUENCE: 12

Ala Ser Ala Ser Gly Asn Pro Phe Glu Gly Tyr Gln Leu Tyr Ala Asn
1               5                   10                  15

Pro Tyr Tyr Ala Ser Glu Val Ile Ser Leu Ala Ile Pro Ser Leu Ser
            20                  25                  30

Ser Glu Leu Val Pro Lys Ala Ser Glu Val Ala Lys Val Pro Ser Phe
        35                  40                  45

Val Trp Leu Asp Gln Ala Ala Lys Val Pro Ser Met Gly Asp Tyr Leu
    50                  55                  60

Lys Asp Ile Gln Ser Gln Asn Ala Ala Gly Ala Asp Pro Pro Ile Ala
65                  70                  75                  80

Gly Ile Phe Val Val Tyr Asp Leu Pro Asp Arg Asp Cys Ala Ala Ala
                85                  90                  95
```

```
Ala Ser Asn Gly Glu Phe Ser Ile Ala Asn Asn Gly Val Ala Leu Tyr
            100                 105                 110

Lys Gln Tyr Ile Asp Ser Ile Arg Glu Gln Leu Thr Thr Tyr Ser Asp
        115                 120                 125

Val His Thr Ile Leu Val Ile Glu Pro Asp Ser Leu Ala Asn Val Val
    130                 135                 140

Thr Asn Leu Asn Val Pro Lys Cys Ala Asn Ala Gln Asp Ala Tyr Leu
145                 150                 155                 160

Glu Cys Ile Asn Tyr Ala Ile Thr Gln Leu Asp Leu Pro Asn Val Ala
                165                 170                 175

Met Tyr Leu Asp Ala Gly His Ala Gly Trp Leu Gly Trp Gln Ala Asn
            180                 185                 190

Leu Ala Pro Ala Ala Gln Leu Phe Ala Ser Val Tyr Lys Asn Ala Ser
        195                 200                 205

Ser Pro Ala Ser Val Arg Gly Leu Ala Thr Asn Val Ala Asn Tyr Asn
    210                 215                 220

Ala Trp Ser Ile Ser Arg Cys Pro Ser Tyr Thr Gln Gly Asp Ala Asn
225                 230                 235                 240

Cys Asp Glu Glu Asp Tyr Val Asn Ala Leu Gly Pro Leu Phe Gln Glu
                245                 250                 255

Gln Gly Phe Pro Ala Tyr Phe Ile Ile Asp Thr Ser Arg Asn Gly Val
            260                 265                 270

Arg Pro Thr Lys Gln Ser Gln Trp Gly Asp Trp Cys Asn Val Ile Gly
        275                 280                 285

Thr Gly Phe Gly Val Arg Pro Thr Thr Asp Thr Gly Asn Pro Leu Glu
    290                 295                 300

Asp Ala Phe Val Trp Val Lys Pro Gly Gly Glu Ser Asp Gly Thr Ser
305                 310                 315                 320

Asn Thr Thr Ser Pro Arg Tyr Asp Tyr His Cys Gly Leu Ser Asp Ala
                325                 330                 335

Leu Gln Pro Ala Pro Glu Ala Gly Thr Trp Phe Gln Ala Tyr Phe Glu
            340                 345                 350

Gln Leu Leu Thr Asn Ala Asn Pro Leu Phe
        355                 360
```

<210> SEQ ID NO 13
<211> LENGTH: 361
<212> TYPE: PRT
<213> ORGANISM: Gibberella zeae K59

<400> SEQUENCE: 13

```
Pro Val Ala Thr Asn Asn Pro Phe Ser Gly Val Asp Leu Trp Ala Asn
1               5                   10                  15

Asn Tyr Tyr Arg Ser Glu Val Ser Thr Leu Ala Ile Pro Lys Leu Ser
            20                  25                  30

Gly Ala Met Ala Thr Ala Ala Ala Lys Val Ala Asp Val Pro Ser Phe
        35                  40                  45

Gln Trp Met Asp Thr Tyr Asp His Ile Ser Phe Met Glu Asp Ser Leu
    50                  55                  60

Ala Asp Ile Arg Lys Ala Asn Lys Ala Gly Gly Asn Tyr Ala Gly Gln
65                  70                  75                  80

Phe Val Val Tyr Asp Leu Pro Asp Arg Asp Cys Ala Ala Ala Ala Ser
                85                  90                  95

Asn Gly Glu Tyr Ser Leu Asp Lys Asp Gly Lys Asn Lys Tyr Lys Ala
            100                 105                 110
```

```
Tyr Ile Ala Asp Gln Gly Ile Leu Gln Asp Tyr Ser Asp Thr Arg Ile
        115                 120                 125

Ile Leu Val Ile Glu Pro Asp Ser Leu Ala Asn Met Val Thr Asn Met
130                 135                 140

Asn Val Pro Lys Cys Ala Asn Ala Ala Ser Ala Tyr Lys Glu Leu Thr
145                 150                 155                 160

Ile His Ala Leu Lys Glu Leu Asn Leu Pro Asn Val Ser Met Tyr Ile
                165                 170                 175

Asp Ala Gly His Gly Gly Trp Leu Gly Trp Pro Ala Asn Leu Pro Pro
            180                 185                 190

Ala Ala Gln Leu Tyr Gly Gln Leu Tyr Lys Asp Ala Gly Lys Pro Ser
        195                 200                 205

Arg Leu Arg Gly Leu Val Thr Asn Val Ser Asn Tyr Asn Ala Trp Lys
210                 215                 220

Leu Ser Ser Lys Pro Asp Tyr Thr Glu Ser Asn Pro Asn Tyr Asp Glu
225                 230                 235                 240

Gln Lys Tyr Ile His Ala Leu Ser Pro Leu Leu Gln Glu Gly Trp
                245                 250                 255

Pro Gly Ala Lys Phe Ile Val Asp Gln Gly Arg Ser Gly Lys Gln Pro
            260                 265                 270

Thr Gly Gln Lys Ala Trp Gly Asp Trp Cys Asn Ala Pro Gly Thr Gly
        275                 280                 285

Phe Gly Leu Arg Pro Ser Ala Asn Thr Gly Asp Ala Leu Val Asp Ala
        290                 295                 300

Phe Val Trp Val Lys Pro Gly Gly Glu Ser Asp Gly Ser Thr Ser Asp Thr
305                 310                 315                 320

Ser Ala Ala Arg Tyr Asp Tyr His Cys Gly Ile Asp Gly Ala Val Lys
                325                 330                 335

Pro Ala Pro Glu Ala Gly Thr Trp Phe Gln Ala Tyr Phe Glu Gln Leu
            340                 345                 350

Leu Lys Asn Ala Asn Pro Ser Phe Leu
        355                 360

<210> SEQ ID NO 14
<211> LENGTH: 362
<212> TYPE: PRT
<213> ORGANISM: Fusarium oxysporum

<400> SEQUENCE: 14

Pro Ala Ala Ser Asp Asn Pro Tyr Ala Gly Val Asp Leu Trp Ala Asn
1               5                   10                  15

Asn Tyr Tyr Arg Ser Glu Val Met Asn Leu Ala Val Pro Lys Leu Ser
            20                  25                  30

Gly Ala Lys Ala Thr Ala Ala Lys Val Ala Asp Val Pro Ser Phe
        35                  40                  45

Gln Trp Met Asp Thr Tyr Asp His Ile Ser Leu Met Glu Asp Thr Leu
    50                  55                  60

Ala Asp Ile Arg Lys Ala Asn Lys Ala Gly Gly Lys Tyr Ala Gly Gln
65                  70                  75                  80

Phe Val Val Tyr Asp Leu Pro Asn Arg Asp Cys Ala Ala Ala Ser
                85                  90                  95

Asn Gly Glu Tyr Ser Leu Asp Lys Asp Gly Ala Asn Lys Tyr Lys Ala
            100                 105                 110

Tyr Ile Ala Lys Ile Lys Gly Ile Leu Gln Asn Tyr Ser Asp Thr Lys
        115                 120                 125
```

```
Val Ile Leu Val Ile Glu Pro Asp Ser Leu Ala Asn Leu Val Thr Asn
            130                 135                 140

Leu Asn Val Asp Lys Cys Ala Lys Ala Glu Ser Ala Tyr Lys Glu Leu
145                 150                 155                 160

Thr Val Tyr Ala Ile Lys Glu Leu Asn Leu Pro Asn Val Ser Met Tyr
                165                 170                 175

Leu Asp Ala Gly His Gly Gly Trp Leu Gly Trp Pro Ala Asn Ile Gly
            180                 185                 190

Pro Ala Ala Lys Leu Tyr Ala Gln Ile Tyr Lys Asp Ala Gly Lys Pro
        195                 200                 205

Ser Arg Val Arg Gly Leu Val Thr Asn Val Ser Asn Tyr Asn Gly Trp
    210                 215                 220

Lys Leu Ser Thr Lys Pro Asp Tyr Thr Glu Ser Asn Pro Asn Tyr Asp
225                 230                 235                 240

Glu Gln Arg Tyr Ile Asn Ala Phe Ala Pro Leu Leu Ala Gln Glu Gly
                245                 250                 255

Trp Ser Asn Val Lys Phe Ile Val Asp Gln Gly Arg Ser Gly Lys Gln
            260                 265                 270

Pro Thr Gly Gln Lys Ala Gln Gly Asp Trp Cys Asn Ala Lys Gly Thr
        275                 280                 285

Gly Phe Gly Leu Arg Pro Ser Thr Asn Thr Gly Asp Ala Leu Ala Asp
    290                 295                 300

Ala Phe Val Trp Val Lys Pro Gly Gly Glu Ser Asp Gly Thr Ser Asp
305                 310                 315                 320

Thr Ser Ala Ala Arg Tyr Asp Tyr His Cys Gly Leu Asp Asp Ala Leu
                325                 330                 335

Lys Pro Ala Pro Glu Ala Gly Thr Trp Phe Gln Ala Tyr Phe Glu Gln
            340                 345                 350

Leu Leu Asp Asn Ala Asn Pro Ser Phe Leu
        355                 360

<210> SEQ ID NO 15
<211> LENGTH: 363
<212> TYPE: PRT
<213> ORGANISM: Neurospora crassa OR74A

<400> SEQUENCE: 15

Ala Ser Phe Thr Gly Asn Pro Phe Leu Gly Val Gln Gly Trp Ala Asn
1               5                   10                  15

Ser Tyr Tyr Ser Ser Glu Ile Tyr Asn His Ala Ile Pro Ser Met Thr
            20                  25                  30

Gly Ser Leu Ala Ala Gln Ala Ser Ala Val Lys Val Pro Thr Phe
        35                  40                  45

Gln Trp Leu Asp Arg Asn Val Thr Val Asp Thr Leu Met Lys Ser Thr
    50                  55                  60

Leu Glu Glu Ile Arg Ala Ala Asn Lys Ala Gly Ala Asn Pro Pro Tyr
65                  70                  75                  80

Ala Ala His Phe Val Val Tyr Asp Leu Pro Asp Arg Asp Cys Ala Ala
                85                  90                  95

Ala Ala Ser Asn Gly Glu Phe Ser Ile Ala Asn Gly Gly Val Ala Asn
            100                 105                 110

Tyr Lys Thr Tyr Ile Asn Ala Ile Arg Lys Leu Leu Ile Glu Tyr Ser
        115                 120                 125

Asp Ile Arg Thr Ile Leu Val Ile Glu Pro Asp Ser Leu Ala Asn Leu
    130                 135                 140
```

Val Thr Asn Thr Asn Val Ala Lys Cys Ala Asn Ala Ser Ala Tyr
145                 150                 155                 160

Arg Glu Cys Thr Asn Tyr Ala Ile Thr Gln Leu Asp Leu Pro His Val
            165                 170                 175

Ala Gln Tyr Leu Asp Ala Gly His Gly Gly Trp Leu Gly Trp Pro Ala
        180                 185                 190

Asn Ile Gln Pro Ala Ala Thr Leu Phe Ala Asp Ile Tyr Lys Ala Ala
    195                 200                 205

Gly Lys Pro Lys Ser Val Arg Gly Leu Val Thr Asn Val Ser Asn Tyr
210                 215                 220

Asn Gly Trp Ser Leu Ser Ser Ala Pro Ser Tyr Thr Thr Pro Asn Pro
225                 230                 235                 240

Asn Tyr Asp Glu Lys Lys Tyr Ile Glu Ala Phe Ser Pro Leu Leu Asn
                245                 250                 255

Ala Ala Gly Phe Pro Ala Gln Phe Ile Val Asp Thr Gly Arg Ser Gly
            260                 265                 270

Lys Gln Pro Thr Gly Gln Ile Glu Gln Gly Asp Trp Cys Asn Ala Ile
        275                 280                 285

Gly Thr Gly Phe Gly Val Arg Pro Thr Thr Asn Thr Gly Ser Ser Leu
290                 295                 300

Ala Asp Ala Phe Val Trp Val Lys Pro Gly Gly Glu Ser Asp Gly Thr
305                 310                 315                 320

Ser Asp Thr Ser Ala Thr Arg Tyr Asp Tyr His Cys Gly Leu Ser Asp
                325                 330                 335

Ala Leu Lys Pro Ala Pro Glu Ala Gly Gln Trp Phe Gln Ala Tyr Phe
            340                 345                 350

Glu Gln Leu Leu Lys Asn Ala Asn Pro Ala Phe
        355                 360

<210> SEQ ID NO 16
<211> LENGTH: 364
<212> TYPE: PRT
<213> ORGANISM: Aspergillus nidulans FGSC A4

<400> SEQUENCE: 16

Val Gln Ala Thr Gly Asn Pro Phe Glu Gly Tyr Gln Leu Tyr Ala Asn
1               5                   10                  15

Pro Tyr Tyr Ser Ser Glu Val Met Thr Leu Ala Val Pro Ser Met Thr
                20                  25                  30

Gly Ser Leu Ala Glu Gln Ala Thr His Ala Ala Glu Ile Pro Ser Phe
            35                  40                  45

His Trp Leu Asp Thr Thr Ala Lys Val Pro Thr Met Gly Glu Tyr Leu
        50                  55                  60

Ala Asp Ile Lys Glu Gln Asn Asp Ala Gly Ala Asn Pro Pro Ile Ala
65                  70                  75                  80

Gly Ile Phe Val Val Tyr Asn Leu Pro Asp Arg Asp Cys Ala Ala Leu
                85                  90                  95

Ala Ser Asn Gly Glu Leu Ser Ile Ala Asp Gly Gly Val Glu Lys Tyr
            100                 105                 110

Lys Glu Tyr Ile Asp Ala Ile Arg Ala His Ala Val Glu Tyr Ser Asp
        115                 120                 125

Thr Asn Ile Ile Leu Ile Ile Glu Pro Asp Ser Leu Ala Asn Leu Val
    130                 135                 140

Thr Asn Leu Asn Val Glu Lys Cys Ala Asn Ala Gln Asp Ala Tyr Leu
145                 150                 155                 160

```
Glu Cys Thr Asn Tyr Ala Ile Thr Gln Leu Asp Leu Pro Asn Val Ser
            165                 170                 175

Met Tyr Leu Asp Ala Gly His Ala Gly Trp Leu Gly Trp Pro Ala Asn
        180                 185                 190

Ile Gly Pro Ala Ala Gln Leu Phe Ala Gly Val Tyr Gln Asp Ala Gly
        195                 200                 205

Ala Pro Ala Ala Leu Arg Gly Leu Ala Thr Asn Val Ala Asn Tyr Asn
    210                 215                 220

Ala Phe Ser Ile Asp Thr Cys Pro Ser Tyr Thr Ser Gln Asn Ala Val
225                 230                 235                 240

Cys Asp Glu Lys Gly Tyr Ile Asn Ser Phe Ala Pro Glu Leu Ser Ala
                245                 250                 255

Ala Gly Trp Asp Ala His Phe Ile Val Asp Thr Gly Arg Asn Gly Lys
            260                 265                 270

Gln Pro Thr Gly Gln Ile Glu Trp Gly Asp Trp Cys Asn Val Lys Gly
        275                 280                 285

Thr Gly Phe Gly Val Arg Pro Thr Thr Asp Thr Gly Asp Glu Leu Val
        290                 295                 300

Asp Ala Phe Val Trp Val Lys Pro Gly Gly Glu Ser Asp Gly Thr Ser
305                 310                 315                 320

Asp Gln Ser Ala Glu Arg Tyr Asp Ala His Cys Gly Ala Ala Ala Ala
                325                 330                 335

Leu Gln Pro Ala Pro Glu Ala Gly Thr Trp Phe Gln Ala Tyr Phe Glu
            340                 345                 350

Gln Leu Val Ala Asn Ala Asn Pro Pro Leu Ser Ser
                355                 360

<210> SEQ ID NO 17
<211> LENGTH: 363
<212> TYPE: PRT
<213> ORGANISM: Aspergillus tubingensis
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid

<400> SEQUENCE: 17

Ala Ser Ala Thr Gly Asn Pro Phe Glu Gly Tyr Gln Leu Tyr Val Asn
1               5                   10                  15

Pro Tyr Tyr Lys Ser Gln Val Glu Ser Ser Ala Ile Pro Ser Leu Ser
                20                  25                  30

Ala Ser Ser Leu Val Ala Gln Ala Ser Ala Ala Asp Val Pro Ser
            35                  40                  45

Phe Tyr Trp Leu Asp Thr Ala Asp Lys Val Pro Thr Met Gly Glu Tyr
        50                  55                  60

Leu Asp Asp Ile Gln Thr Gln Asn Ala Gly Ala Asn Pro Pro Ile
65                  70                  75                  80

Ala Gly Ile Phe Val Val Tyr Asp Leu Pro Asp Arg Asp Cys Ala Ala
                85                  90                  95

Leu Ala Ser Asn Gly Glu Tyr Ala Ile Ser Asp Gly Gly Val Glu Lys
            100                 105                 110
```

-continued

```
Tyr Lys Ala Tyr Ile Asp Ser Ile Arg Glu Gln Val Glu Thr Tyr Ser
            115                 120                 125

Asp Val Gln Thr Ile Leu Ile Glu Pro Asp Ser Leu Ala Asn Leu
130                 135                 140

Val Thr Asn Leu Asp Val Ala Lys Cys Ala Asn Ala Gln Ser Ala Tyr
145                 150                 155                 160

Leu Glu Cys Thr Asn Tyr Ala Leu Glu Gln Leu Asn Leu Pro Asn Val
                165                 170                 175

Ala Met Tyr Leu Asp Ala Gly His Ala Gly Trp Leu Gly Trp Pro Ala
                180                 185                 190

Asn Ile Gly Pro Ala Ala Glu Leu Tyr Ala Ser Val Tyr Lys Asn Ala
                195                 200                 205

Ser Ser Pro Ala Ala Val Arg Gly Leu Ala Thr Asx Val Ala Asn Phe
210                 215                 220

Asn Ala Trp Ser Ile Asp Thr Cys Pro Ser Tyr Thr Ser Gly Asn Asp
225                 230                 235                 240

Val Cys Asp Glu Lys Ser Tyr Ile Asn Ala Phe Ala Pro Glu Leu Ser
                245                 250                 255

Xaa Ala Gly Phe Asp Ala His Phe Ile Thr Asp Thr Gly Arg Asn Gly
                260                 265                 270

Lys Gln Pro Thr Gly Gln Ser Ala Trp Gly Asp Trp Gly Asn Val Lys
                275                 280                 285

Asp Thr Gly Phe Gly Ala Xaa Pro Thr Thr Thr Gly Asn Glu Leu
290                 295                 300

Ala Asp Ala Phe Val Trp Xaa Asn Pro Gly Gly Lys Ser Asp Gly Thr
305                 310                 315                 320

Ser Asp Thr Ser Ser Arg Tyr Asp Ala His Cys Gly Tyr Ser Asp
                325                 330                 335

Ala Leu Gln Pro Ala Pro Glu Ala Gly Thr Trp Phe Gln Ala Tyr Phe
                340                 345                 350

Glu Gln Leu Leu Thr Asn Ala Asn Pro Ser Leu
                355                 360

<210> SEQ ID NO 18
<211> LENGTH: 362
<212> TYPE: PRT
<213> ORGANISM: Magnaporthe grisea 70-15

<400> SEQUENCE: 18

Ala Ser Phe Thr Gly Asn Pro Phe Ala Gly Val Asn Leu Phe Pro Asn
1               5                   10                  15

Lys Phe Tyr Ser Ser Glu Val His Thr Leu Ala Ile Pro Ser Leu Thr
                20                  25                  30

Gly Ser Leu Val Ala Lys Ala Ser Ala Val Ala Gln Val Pro Ser Phe
            35                  40                  45

Gln Trp Leu Asp Ile Ala Ala Lys Val Glu Thr Leu Met Pro Gly Ala
        50                  55                  60

Leu Ala Asp Val Arg Ala Ala Asn Ala Ala Gly Gly Asn Tyr Ala Ala
65                  70                  75                  80

Gln Leu Val Val Tyr Asp Leu Pro Asp Arg Asp Cys Ala Ala Ala Ala
                85                  90                  95

Ser Asn Gly Glu Phe Ser Ile Ala Asp Gly Gly Val Val Lys Tyr Lys
                100                 105                 110

Ala Tyr Ile Asp Ala Ile Arg Lys Gln Leu Leu Ala Tyr Ser Asp Val
            115                 120                 125
```

Arg Thr Ile Leu Val Ile Glu Pro Asp Ser Leu Ala Asn Met Val Thr
130                 135                 140

Asn Met Gly Val Pro Lys Cys Ala Gly Ala Lys Asp Ala Tyr Leu Glu
145                 150                 155                 160

Cys Thr Ile Tyr Ala Val Lys Gln Leu Asn Leu Pro His Val Ala Met
                165                 170                 175

Tyr Leu Asp Gly Gly His Ala Gly Trp Leu Gly Trp Pro Ala Asn Leu
            180                 185                 190

Gln Pro Ala Ala Asp Leu Phe Gly Lys Leu Tyr Ala Asp Ala Gly Lys
        195                 200                 205

Pro Ser Gln Leu Arg Gly Met Ala Thr Asn Val Ala Asn Tyr Asn Ala
    210                 215                 220

Trp Asp Leu Thr Thr Ala Pro Ser Tyr Thr Thr Pro Asn Pro Asn Phe
225                 230                 235                 240

Asp Glu Lys Lys Tyr Ile Ser Ala Phe Ala Pro Leu Leu Ala Ala Lys
                245                 250                 255

Gly Trp Ser Ala His Phe Ile Ile Asp Gln Gly Arg Ser Gly Lys Gln
            260                 265                 270

Pro Thr Gly Gln Lys Glu Trp Gly His Trp Cys Asn Gln Gln Gly Val
        275                 280                 285

Gly Phe Gly Arg Arg Pro Ser Ala Asn Thr Gly Ser Glu Leu Ala Asp
    290                 295                 300

Ala Phe Val Trp Ile Lys Pro Gly Gly Glu Cys Asp Gly Val Ser Asp
305                 310                 315                 320

Pro Thr Ala Pro Arg Phe Asp His Phe Cys Gly Thr Tyr Pro Gly Ala
                325                 330                 335

Met Ser Asp Ala Pro Gln Ala Gly Gln Trp Phe Gln Lys Tyr Phe Glu
            340                 345                 350

Met Leu Leu Thr Asn Ala Asn Pro Pro Leu
        355                 360

<210> SEQ ID NO 19
<211> LENGTH: 364
<212> TYPE: PRT
<213> ORGANISM: Chaetomium thermophilum

<400> SEQUENCE: 19

Ala Ser Tyr Asn Gly Asn Pro Phe Ser Gly Val Gln Leu Trp Ala Asn
1               5                   10                  15

Thr Tyr Tyr Ser Ser Glu Val His Thr Leu Ala Ile Pro Ser Leu Ser
                20                  25                  30

Pro Glu Leu Ala Ala Lys Ala Ala Lys Val Ala Glu Val Pro Ser Phe
            35                  40                  45

Gln Trp Leu Asp Arg Asn Val Thr Val Asp Thr Leu Phe Ser Gly Thr
        50                  55                  60

Leu Ala Glu Ile Arg Ala Ala Asn Gln Arg Gly Ala Asn Pro Pro Tyr
65                  70                  75                  80

Ala Gly Ile Phe Val Val Tyr Asp Leu Pro Asp Arg Asp Cys Ala Ala
                85                  90                  95

Ala Ala Ser Asn Gly Glu Trp Ser Ile Ala Asn Asn Gly Ala Asn Asn
            100                 105                 110

Tyr Lys Arg Tyr Ile Asp Arg Ile Arg Glu Leu Leu Ile Gln Tyr Ser
        115                 120                 125

Asp Ile Arg Thr Ile Leu Val Ile Glu Pro Asp Ser Leu Ala Asn Met
    130                 135                 140

```
Val Thr Asn Met Asn Val Gln Lys Cys Ser Asn Ala Ala Ser Thr Tyr
145                 150                 155                 160

Lys Glu Leu Thr Val Tyr Ala Leu Lys Gln Leu Asn Leu Pro His Val
            165                 170                 175

Ala Met Tyr Met Asp Ala Gly His Ala Gly Trp Leu Gly Trp Pro Ala
        180                 185                 190

Asn Ile Gln Pro Ala Ala Glu Leu Phe Ala Gln Ile Tyr Arg Asp Ala
    195                 200                 205

Gly Arg Pro Ala Ala Val Arg Gly Leu Ala Thr Asn Val Ala Asn Tyr
210                 215                 220

Asn Ala Trp Ser Ile Ala Ser Pro Pro Ser Tyr Thr Ser Pro Asn Pro
225                 230                 235                 240

Asn Tyr Asp Glu Lys His Tyr Ile Glu Ala Phe Ala Pro Leu Leu Arg
            245                 250                 255

Asn Gln Gly Phe Asp Ala Lys Phe Ile Val Asp Thr Gly Arg Asn Gly
        260                 265                 270

Lys Gln Pro Thr Gly Gln Leu Glu Trp Gly His Trp Cys Asn Val Lys
    275                 280                 285

Gly Thr Gly Phe Gly Val Arg Pro Thr Ala Asn Thr Gly His Glu Leu
290                 295                 300

Val Asp Ala Phe Val Trp Val Lys Pro Gly Gly Glu Ser Asp Gly Thr
305                 310                 315                 320

Ser Ala Asp Thr Ser Ala Ala Arg Tyr Asp Tyr His Cys Gly Leu Ser
            325                 330                 335

Asp Ala Leu Thr Pro Ala Pro Glu Ala Gly Gln Trp Phe Gln Ala Tyr
        340                 345                 350

Phe Glu Gln Leu Leu Ile Asn Ala Asn Pro Pro Leu
    355                 360

<210> SEQ ID NO 20
<211> LENGTH: 363
<212> TYPE: PRT
<213> ORGANISM: Chaetomium thermophilum CT2

<400> SEQUENCE: 20

Ala Ser Tyr Asn Gly Asn Pro Phe Ser Gly Val Gln Leu Trp Ala Asn
1               5                   10                  15

Thr Tyr Tyr Ser Ser Glu Val His Thr Leu Ala Ile Pro Ser Leu Ser
            20                  25                  30

Pro Glu Leu Ala Ala Lys Ala Ala Lys Val Ala Glu Val Pro Ser Phe
        35                  40                  45

Gln Trp Leu Asp Arg Asn Val Thr Val Asp Thr Leu Phe Ser Gly Thr
    50                  55                  60

Leu Ala Glu Ile Arg Ala Ala Asn Gln Arg Gly Ala Asn Pro Pro Tyr
65                  70                  75                  80

Ala Gly Ile Phe Val Val Tyr Asp Leu Pro Asp Arg Asp Cys Ala Ala
            85                  90                  95

Ala Ala Ser Asn Gly Glu Trp Ser Ile Ala Asn Asn Gly Ala Asn Asn
        100                 105                 110

Leu Gln Arg Tyr Ile Asp Arg Ile Arg Glu Leu Leu Ile Gln Tyr Ser
    115                 120                 125

Asp Ile Arg Thr Ile Leu Val Ile Glu Pro Asp Ser Leu Ala Asn Met
130                 135                 140

Val Thr Asn Met Asn Val Gln Lys Cys Ser Asn Ala Ala Ser Thr Tyr
145                 150                 155                 160
```

```
Lys Glu Leu Thr Val Tyr Ala Leu Lys Gln Leu Asn Leu Pro His Val
                165                 170                 175

Ala Met Tyr Met Asp Ala Gly His Ala Gly Trp Leu Gly Trp Pro Ala
            180                 185                 190

Asn Ile Gln Pro Ala Ala Glu Leu Phe Ala Gln Ile Tyr Arg Asp Ala
        195                 200                 205

Gly Arg Pro Ala Ala Val Arg Gly Leu Ala Thr Asn Val Ala Asn Tyr
    210                 215                 220

Asn Ala Trp Ser Ile Ala Ser Pro Pro Ser Tyr Thr Ser Pro Asn Pro
225                 230                 235                 240

Asn Tyr Asp Glu Lys His Tyr Ile Glu Ala Phe Ala Pro Leu Leu Arg
                245                 250                 255

Asn Gln Gly Phe Asp Ala Lys Phe Ile Val Asp Thr Gly Arg Asn Gly
            260                 265                 270

Lys Gln Pro Thr Gly Gln Leu Glu Trp Gly His Trp Cys Asn Val Lys
        275                 280                 285

Gly Thr Gly Phe Gly Val Arg Pro Thr Ala Asn Thr Gly His Glu Leu
    290                 295                 300

Val Asp Ala Phe Val Trp Val Lys Pro Gly Gly Glu Ser Asp Gly Thr
305                 310                 315                 320

Ser Asp Thr Ser Ala Ala Arg Tyr Asp Tyr His Cys Gly Leu Ser Asp
                325                 330                 335

Ala Leu Thr Pro Ala Pro Glu Ala Gly Gln Trp Phe Gln Ala Tyr Phe
            340                 345                 350

Glu Gln Leu Leu Ile Asn Ala Asn Pro Pro Phe
        355                 360

<210> SEQ ID NO 21
<211> LENGTH: 360
<212> TYPE: PRT
<213> ORGANISM: Stilbella annulata

<400> SEQUENCE: 21

Ala Thr Tyr Thr Gly Asn Pro Phe Leu Gly Val Asn Gln Trp Ala Asn
1               5                   10                  15

Asn Phe Tyr Arg Ser Glu Ile Met Asn Ile Ala Val Pro Ser Leu Ser
            20                  25                  30

Gly Ala Met Ala Thr Ala Ala Lys Val Ala Asp Val Pro Thr Phe
        35                  40                  45

Gln Trp Ile Asp Lys Met Asp Lys Leu Pro Leu Ile Asp Glu Ala Leu
    50                  55                  60

Ala Asp Val Arg Ala Ala Asn Ala Arg Gly Gly Asn Tyr Ala Ser Ile
65                  70                  75                  80

Leu Val Val Tyr Asn Leu Pro Asp Arg Asp Cys Ala Ala Ala Ser
                85                  90                  95

Asn Gly Glu Phe Ala Ile Ala Asp Gly Gly Val Ala Lys Tyr Lys Asn
            100                 105                 110

Tyr Ile Asp Glu Ile Arg Lys Leu Val Ile Lys Tyr Asn Asp Leu Arg
        115                 120                 125

Ile Ile Leu Val Ile Glu Pro Asp Ser Leu Ala Asn Met Val Thr Asn
    130                 135                 140

Met Asn Val Ala Lys Cys Gln Asn Ala Ala Ser Ala Tyr Arg Glu Cys
145                 150                 155                 160

Thr Asn Tyr Ala Leu Thr Asn Leu Asp Leu Pro Asn Val Ala Gln Tyr
                165                 170                 175
```

```
Met Asp Ala Gly His Ala Gly Trp Leu Gly Trp Pro Ala Asn Ile Thr
            180                 185                 190
Pro Ala Ala Gln Leu Phe Ala Glu Val Tyr Lys Gln Ala Gly Ser Pro
            195                 200                 205
Lys Ser Val Arg Gly Leu Ala Ile Asn Val Ser Asn Tyr Asn Ala Trp
210                 215                 220
Ser Val Ser Ser Pro Pro Tyr Thr Ser Pro Asn Pro Asn Tyr Asp
225                 230                 235                 240
Glu Arg His Phe Val Glu Ala Phe Ala Pro Leu Leu Arg Gln Asn Gly
            245                 250                 255
Trp Asp Ala Lys Phe Ile Val Asp Gln Gly Arg Ser Gly Arg Gln Pro
            260                 265                 270
Thr Gly Gln Gln Glu Trp Gly His Trp Cys Asn Ala Ile Gly Thr Gly
            275                 280                 285
Phe Gly Gln Arg Pro Thr Ser Asn Thr Gly His Ala Asp Val Asp Ala
            290                 295                 300
Phe Val Trp Ile Lys Pro Gly Gly Glu Cys Asp Gly Thr Ser Asp Thr
305                 310                 315                 320
Ser Ala Ala Arg Tyr Asp His Phe Cys Gly Asn Pro Asp Ala Leu Lys
            325                 330                 335
Pro Ala Pro Glu Ala Gly Glu Trp Phe Gln Ala Tyr Phe Glu Gln Leu
            340                 345                 350
Leu Arg Asn Ala Asn Pro Ala Phe
            355                 360

<210> SEQ ID NO 22
<211> LENGTH: 453
<212> TYPE: PRT
<213> ORGANISM: Humicola insolens

<400> SEQUENCE: 22

Ala Ser Cys Ala Pro Thr Trp Gly Gln Cys Gly Gly Ile Gly Phe Asn
1               5                   10                  15
Gly Pro Thr Cys Cys Gln Ser Gly Ser Thr Cys Val Lys Gln Asn Asp
            20                  25                  30
Trp Tyr Ser Gln Cys Leu Pro Gly Ser Gln Val Thr Thr Thr Ser Thr
            35                  40                  45
Thr Ser Thr Ser Ser Ser Ser Thr Ser Arg Ala Thr Ser Thr Thr
50                  55                  60
Arg Thr Gly Gly Val Thr Ser Ile Thr Thr Ala Pro Thr Arg Thr Val
65                  70                  75                  80
Thr Ile Pro Gly Gly Ala Thr Thr Thr Ala Ser Tyr Asn Gly Asn Pro
            85                  90                  95
Phe Glu Gly Val Gln Leu Trp Ala Asn Asn Tyr Tyr Arg Ser Glu Val
            100                 105                 110
His Thr Leu Ala Ile Pro Gln Ile Thr Asp Pro Ala Leu Arg Ala Ala
            115                 120                 125
Ala Ser Ala Val Ala Glu Val Pro Ser Phe Gln Trp Leu Asp Arg Asn
130                 135                 140
Val Thr Val Asp Thr Leu Leu Val Glu Thr Leu Ser Glu Ile Arg Ala
145                 150                 155                 160
Ala Asn Gln Ala Gly Ala Asn Pro Pro Tyr Ala Ala Gln Ile Val Val
            165                 170                 175
Tyr Asp Leu Pro Asp Arg Asp Cys Ala Ala Ala Ser Asn Gly Glu
            180                 185                 190
```

```
Trp Ala Ile Ala Asn Asn Gly Ala Asn Asn Tyr Lys Gly Tyr Ile Asn
            195                 200                 205

Arg Ile Arg Glu Ile Leu Ile Ser Phe Ser Asp Val Arg Thr Ile Leu
210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
            245                 250                 255

Ala Leu Lys Gln Leu Asp Leu Pro His Val Ala Met Tyr Met Asp Ala
            260                 265                 270

Gly His Ala Gly Trp Leu Gly Trp Pro Ala Asn Ile Gln Pro Ala Ala
            275                 280                 285

Glu Leu Phe Ala Lys Ile Tyr Glu Asp Ala Gly Lys Pro Arg Ala Val
            290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                    325                 330                 335

Tyr Ile Glu Ala Phe Arg Pro Leu Leu Glu Ala Arg Gly Phe Pro Ala
            340                 345                 350

Gln Phe Ile Val Asp Gln Gly Arg Ser Gly Lys Gln Pro Thr Gly Gln
            355                 360                 365

Lys Glu Trp Gly His Trp Cys Asn Ala Ile Gly Thr Gly Phe Gly Met
            370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                    405                 410                 415

Arg Tyr Asp Tyr His Cys Gly Leu Glu Asp Ala Leu Lys Pro Ala Pro
                    420                 425                 430

Glu Ala Gly Gln Trp Phe Gln Ala Tyr Phe Glu Gln Leu Leu Arg Asn
            435                 440                 445

Ala Asn Pro Pro Phe
    450

<210> SEQ ID NO 23
<211> LENGTH: 360
<212> TYPE: PRT
<213> ORGANISM: Humicola insolens

<400> SEQUENCE: 23

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ala Ser Ala Val Ala Glu Val Pro Ser Phe Gln Trp Leu
            35                  40                  45

Asp Arg Asn Val Thr Val Asp Thr Leu Leu Val Gln Thr Leu Ser Glu
        50                  55                  60

Ile Arg Glu Ala Asn Gln Ala Gly Ala Asn Pro Gln Tyr Ala Ala Gln
65              70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110
```

-continued

```
Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
        130                 135                 140

Met Asn Val Pro Lys Cys Ser Gly Ala Ala Ser Thr Tyr Arg Glu Leu
145                 150                 155                 160

Thr Ile Tyr Ala Leu Lys Gln Leu Asp Leu Pro His Val Ala Met Tyr
            165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
                195                 200                 205

Arg Ala Val Arg Gly Leu Ala Thr Asn Val Ala Asn Tyr Asn Ala Trp
210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Ala Gln Phe Ile Val Asp Gln Gly Arg Ser Gly Lys Gln Pro
                260                 265                 270

Thr Gly Gln Lys Glu Trp Gly His Trp Cys Asn Ala Ile Gly Thr Gly
            275                 280                 285

Phe Gly Met Arg Pro Thr Ala Asn Thr Gly His Gln Tyr Val Asp Ala
            290                 295                 300

Phe Val Trp Val Lys Pro Gly Gly Glu Cys Asp Gly Thr Ser Asp Thr
305                 310                 315                 320

Thr Ala Ala Arg Tyr Asp Tyr His Cys Gly Leu Glu Asp Ala Leu Lys
                325                 330                 335

Pro Ala Pro Glu Ala Gly Gln Trp Phe Asn Glu Tyr Phe Ile Gln Leu
                340                 345                 350

Leu Arg Asn Ala Asn Pro Pro Phe
            355                 360

<210> SEQ ID NO 24
<211> LENGTH: 362
<212> TYPE: PRT
<213> ORGANISM: Cochliobolus heterostrophus C4

<400> SEQUENCE: 24

Ala Ala Pro Ser Gly Asn Pro Phe Ala Gly Lys Asn Phe Tyr Ala Asn
1               5                   10                  15

Pro Tyr Tyr Ser Ser Glu Val His Thr Leu Ala Met Pro Ser Leu Pro
            20                  25                  30

Ala Ser Leu Lys Pro Ala Ala Thr Ala Val Ala Lys Val Gly Ser Phe
        35                  40                  45

Val Trp Met Asp Thr Met Ala Lys Val Pro Leu Met Asp Thr Tyr Leu
    50                  55                  60

Ala Asp Ile Lys Ala Lys Asn Ala Ala Gly Ala Asn Leu Met Gly Thr
65                  70                  75                  80

Phe Val Val Tyr Asp Leu Pro Asp Arg Asp Cys Ala Ala Leu Ala Ser
                85                  90                  95

Asn Gly Glu Leu Lys Ile Asp Glu Gly Gly Val Glu Lys Tyr Lys Thr
            100                 105                 110

Gln Tyr Ile Asp Lys Ile Ala Ala Ile Lys Lys Tyr Pro Asp Val
        115                 120                 125
```

Lys Ile Asn Leu Ala Ile Glu Pro Asp Ser Leu Ala Asn Met Val Thr
130                 135                 140

Asn Met Gly Val Gln Lys Cys Ser Arg Ala Ala Pro Tyr Tyr Lys Glu
145                 150                 155                 160

Leu Thr Ala Tyr Ala Leu Lys Thr Leu Asn Phe Asn Asn Val Asp Met
                165                 170                 175

Tyr Met Asp Gly Gly His Ala Gly Trp Leu Gly Trp Asp Ala Asn Ile
            180                 185                 190

Gly Pro Thr Ala Lys Leu Phe Ala Glu Val Tyr Lys Ala Ala Gly Ser
        195                 200                 205

Pro Arg Gly Val Arg Gly Ile Val Thr Asn Val Ser Asn Tyr Asn Ala
210                 215                 220

Leu Arg Val Ser Ser Cys Pro Ser Ile Thr Gln Gly Asn Lys Asn Cys
225                 230                 235                 240

Asp Glu Glu Arg Tyr Ile Asn Ala Leu Ala Pro Leu Leu Lys Asn Glu
                245                 250                 255

Gly Phe Pro Ala His Phe Ile Val Asp Gln Gly Arg Ser Gly Lys Val
            260                 265                 270

Pro Thr Asn Gln Gln Glu Trp Gly Asp Trp Cys Asn Val Ser Gly Ala
        275                 280                 285

Gly Phe Gly Thr Arg Pro Thr Thr Asn Thr Gly Asn Ala Leu Ile Asp
290                 295                 300

Ala Ile Val Trp Val Lys Pro Gly Gly Glu Ser Asp Gly Thr Ser Asp
305                 310                 315                 320

Thr Ser Ala Ala Arg Tyr Asp Ala His Cys Gly Arg Asn Ser Ala Phe
                325                 330                 335

Lys Pro Ala Pro Glu Ala Gly Thr Trp Phe Gln Ala Tyr Phe Glu Met
            340                 345                 350

Leu Leu Lys Asn Ala Asn Pro Ala Leu Ala
        355                 360

<210> SEQ ID NO 25
<211> LENGTH: 351
<212> TYPE: PRT
<213> ORGANISM: Agaricus bisporus D649

<400> SEQUENCE: 25

Ala Gly Asn Pro Tyr Thr Gly Lys Thr Val Trp Leu Ser Pro Phe Tyr
1               5                   10                  15

Ala Asp Glu Val Ala Gln Ala Ala Asp Ile Ser Asn Pro Ser Leu
            20                  25                  30

Ala Thr Lys Ala Ala Ser Val Ala Lys Ile Pro Thr Phe Val Trp Phe
        35                  40                  45

Asp Thr Val Ala Lys Val Pro Asp Leu Gly Gly Tyr Leu Ala Asp Ala
50                  55                  60

Arg Ser Lys Asn Gln Leu Val Gln Ile Val Tyr Asp Leu Pro Asp
65                  70                  75                  80

Arg Asp Cys Ala Ala Leu Ala Ser Asn Gly Glu Phe Ser Leu Ala Asn
                85                  90                  95

Asp Gly Leu Asn Lys Tyr Lys Asn Tyr Val Asp Gln Ile Ala Ala Gln
            100                 105                 110

Ile Lys Gln Phe Pro Asp Val Ser Val Ala Val Ile Glu Pro Asp
        115                 120                 125

Ser Leu Ala Asn Leu Val Thr Asn Leu Asn Val Gln Lys Cys Ala Asn
130                 135                 140

```
Ala Gln Ser Ala Tyr Lys Glu Gly Val Ile Tyr Ala Val Gln Lys Leu
145                 150                 155                 160

Asn Ala Val Gly Val Thr Met Tyr Ile Asp Ala Gly His Ala Gly Trp
                165                 170                 175

Leu Gly Trp Pro Ala Asn Leu Ser Pro Ala Ala Gln Leu Phe Ala Gln
            180                 185                 190

Ile Tyr Arg Asp Ala Gly Ser Pro Arg Asn Leu Arg Gly Ile Ala Thr
        195                 200                 205

Asn Val Ala Asn Phe Asn Ala Leu Arg Ala Ser Ser Pro Asp Pro Ile
210                 215                 220

Thr Gln Gly Asn Ser Asn Tyr Asp Glu Ile His Tyr Ile Glu Ala Leu
225                 230                 235                 240

Ala Pro Met Leu Ser Asn Ala Gly Phe Pro Ala His Phe Ile Val Asp
                245                 250                 255

Gln Gly Arg Ser Gly Val Gln Asn Ile Arg Asp Gln Trp Gly Asp Trp
            260                 265                 270

Cys Asn Val Lys Gly Ala Gly Phe Gly Gln Arg Pro Thr Thr Asn Thr
        275                 280                 285

Gly Ser Ser Leu Ile Asp Ala Ile Val Trp Val Lys Pro Gly Gly Glu
290                 295                 300

Cys Asp Gly Thr Ser Asp Asn Ser Ser Pro Arg Phe Asp Ser His Cys
305                 310                 315                 320

Ser Leu Ser Asp Ala His Gln Pro Ala Pro Glu Ala Gly Thr Trp Phe
                325                 330                 335

Gln Ala Tyr Phe Glu Thr Leu Val Ala Asn Ala Asn Pro Ala Leu
            340                 345                 350

<210> SEQ ID NO 26
<211> LENGTH: 360
<212> TYPE: PRT
<213> ORGANISM: Polyporus arcularius 69B-8

<400> SEQUENCE: 26

Thr Pro Ala Ala Gly Asn Pro Phe Val Gly Val Thr Pro Phe Leu Ser
1               5                   10                  15

Pro Tyr Tyr Ala Ala Glu Val Ala Ala Ala Asp Ala Ile Thr Asp Asp
                20                  25                  30

Ser Thr Leu Lys Ala Lys Ala Ala Ser Val Ala Lys Ile Pro Thr Phe
            35                  40                  45

Thr Trp Leu Asp Ser Val Ala Lys Val Pro Asp Leu Gly Thr Tyr Leu
        50                  55                  60

Ala Asp Ala Ser Ala Leu Gln Lys Ser Ser Gly Gln Pro Gln Val Val
65                  70                  75                  80

Gln Ile Val Val Tyr Asp Leu Pro Asp Arg Asp Cys Ala Ala Lys Ala
                85                  90                  95

Ser Asn Gly Glu Phe Ser Ile Ala Asp Gly Gly Gln Ala Lys Tyr Tyr
                100                 105                 110

Asp Tyr Ile Asp Gln Ile Val Ala Gln Ile Lys Lys Phe Pro Asp Val
            115                 120                 125

Arg Val Ile Ala Val Ile Glu Pro Asp Ser Leu Ala Asn Leu Val Thr
        130                 135                 140

Asn Leu Asn Val Gln Lys Cys Ala Asn Ala Gln Thr Thr Tyr Lys Ala
145                 150                 155                 160

Cys Val Thr Tyr Ala Leu Asn Gln Leu Ala Ser Val Gly Val Tyr Gln
                165                 170                 175
```

```
Tyr Met Asp Ala Gly His Ala Gly Trp Leu Gly Trp Pro Ala Asn Ile
            180                 185                 190

Gln Pro Ala Ala Gln Leu Phe Ala Asp Met Phe Lys Ser Ala Asn Ser
        195                 200                 205

Ser Lys Phe Val Arg Gly Leu Ala Thr Asn Val Ala Asn Tyr Asn Ala
    210                 215                 220

Leu Ser Ala Ala Ser Pro Asp Pro Ile Thr Gln Gly Asp Pro Asn Tyr
225                 230                 235                 240

Asp Glu Leu His Tyr Ile Asn Ala Leu Gly Pro Met Leu Ala Gln Gln
                245                 250                 255

Gly Phe Pro Ala Gln Phe Val Val Asp Gln Gly Arg Ser Gly Gln Gln
            260                 265                 270

Asn Leu Arg Gln Gln Trp Gly Asp Trp Cys Asn Ile Lys Gly Ala Gly
        275                 280                 285

Phe Gly Thr Arg Pro Thr Thr Asn Thr Gly Ser Ser Leu Ile Asp Ala
    290                 295                 300

Ile Val Trp Val Lys Pro Gly Gly Glu Ser Asp Gly Thr Ser Asn Ser
305                 310                 315                 320

Ser Ser Pro Arg Phe Asp Ser Thr Cys Ser Leu Ser Asp Ala Thr Gln
                325                 330                 335

Pro Ala Pro Glu Ala Gly Thr Trp Phe Gln Thr Tyr Phe Glu Thr Leu
            340                 345                 350

Val Ser Lys Ala Asn Pro Pro Leu
        355                 360

<210> SEQ ID NO 27
<211> LENGTH: 358
<212> TYPE: PRT
<213> ORGANISM: Lentinula edodes Stamets CS-2

<400> SEQUENCE: 27

Thr Pro Ala Ala Gly Asn Pro Phe Thr Gly Tyr Glu Ile Tyr Leu Ser
1               5                   10                  15

Pro Tyr Tyr Ala Asn Glu Ile Ala Ala Ala Val Thr Gln Ile Ser Asp
            20                  25                  30

Pro Thr Thr Ala Ala Ala Ala Lys Val Ala Asn Ile Pro Thr Phe
        35                  40                  45

Ile Trp Leu Asp Gln Val Ala Lys Val Pro Asp Leu Gly Thr Tyr Leu
    50                  55                  60

Ala Asp Ala Ser Ala Lys Gln Lys Ser Glu Gly Lys Asn Tyr Leu Val
65                  70                  75                  80

Gln Ile Val Val Tyr Asp Leu Pro Asp Arg Asp Cys Ala Ala Leu Ala
                85                  90                  95

Ser Asn Gly Glu Phe Thr Ile Ala Asp Asn Gly Glu Ala Asn Tyr His
            100                 105                 110

Asp Tyr Ile Asp Gln Ile Val Ala Gln Ile Lys Gln Tyr Pro Asp Val
        115                 120                 125

His Val Val Ala Val Ile Glu Pro Asp Ser Leu Ala Asn Leu Val Thr
    130                 135                 140

Asn Leu Ser Val Ala Lys Cys Ala Asn Ala Gln Thr Thr Tyr Leu Glu
145                 150                 155                 160

Cys Val Thr Tyr Ala Met Gln Gln Leu Ser Ala Val Gly Val Thr Met
                165                 170                 175

Tyr Leu Asp Ala Gly His Ala Gly Trp Leu Gly Trp Pro Ala Asn Leu
            180                 185                 190
```

```
Ser Pro Ala Ala Gln Leu Phe Thr Ser Leu Tyr Ser Asn Ala Gly Ser
    195                 200                 205

Pro Ser Gly Val Arg Gly Leu Ala Thr Asn Val Ala Asn Tyr Asn Ala
    210                 215                 220

Leu Val Ala Thr Thr Pro Asp Pro Ile Thr Gln Gly Asp Pro Asn Tyr
225                 230                 235                 240

Asp Glu Met Leu Tyr Ile Glu Ala Leu Ala Pro Leu Leu Gly Ser Phe
                245                 250                 255

Pro Ala His Phe Ile Val Asp Gln Gly Arg Ser Gly Val Gln Asp Ile
            260                 265                 270

Arg Gln Gln Trp Gly Asp Trp Cys Asn Val Leu Gly Ala Gly Phe Gly
        275                 280                 285

Thr Gln Pro Thr Thr Asn Thr Gly Ser Ser Leu Ile Asp Ser Ile Val
    290                 295                 300

Trp Val Lys Pro Gly Gly Glu Cys Asp Gly Thr Ser Asn Thr Ser Ser
305                 310                 315                 320

Pro Arg Tyr Asp Ala His Cys Gly Leu Pro Asp Ala Thr Pro Asn Ala
                325                 330                 335

Pro Glu Ala Gly Thr Trp Phe Gln Ala Tyr Phe Glu Thr Leu Val Glu
            340                 345                 350

Lys Ala Asn Pro Pro Leu
            355

<210> SEQ ID NO 28
<211> LENGTH: 357
<212> TYPE: PRT
<213> ORGANISM: Lentinula edodes L54

<400> SEQUENCE: 28

Thr Pro Ala Ala Gly Asn Pro Phe Thr Glu Gln Ile Tyr Leu Ser Pro
1               5                   10                  15

Tyr Tyr Ala Asn Glu Ile Ala Ala Val Thr Gln Ile Ser Asp Pro
            20                  25                  30

Thr Thr Ala Ala Ala Ala Lys Val Ala Asn Ile Pro Thr Phe Ile
        35                  40                  45

Trp Leu Asp Gln Val Ala Lys Val Pro Asp Leu Gly Thr Tyr Leu Ala
50                  55                  60

Asp Ala Ser Ala Lys Gln Lys Ser Glu Gly Lys Asn Tyr Leu Val Gln
65                  70                  75                  80

Ile Val Val Tyr Asp Leu Pro Asp Arg Asp Cys Ala Ala Leu Ala Ser
                85                  90                  95

Asn Gly Glu Phe Thr Ile Ala Asp Asn Gly Glu Ala Asn Tyr His Asp
            100                 105                 110

Tyr Ile Asp Gln Ile Val Ala Gln Ile Lys Gln Tyr Pro Asp Val His
        115                 120                 125

Val Val Ala Val Ile Glu Pro Asp Ser Leu Ala Asn Leu Val Thr Asn
    130                 135                 140

Leu Ser Val Ala Lys Cys Ala Asn Ala Gln Thr Thr Tyr Leu Glu Cys
145                 150                 155                 160

Val Thr Tyr Ala Met Gln Gln Leu Ser Ala Val Gly Val Thr Met Tyr
                165                 170                 175

Leu Asp Ala Gly His Ala Gly Trp Leu Gly Trp Pro Ala Asn Leu Ser
            180                 185                 190

Pro Ala Ala Gln Leu Phe Thr Ser Leu Tyr Ser Asn Ala Gly Ser Pro
        195                 200                 205
```

```
Ser Gly Val Arg Gly Leu Ala Thr Asn Val Ala Asn Tyr Asn Ala Leu
    210                 215                 220

Val Ala Thr Thr Pro Asp Pro Ile Thr Gln Gly Asp Pro Asn Tyr Asp
225                 230                 235                 240

Glu Met Leu Tyr Ile Glu Ala Leu Ala Pro Leu Leu Gly Ser Phe Pro
                245                 250                 255

Ala His Phe Ile Val Asp Gln Gly Arg Ser Gly Val Gln Asp Ile Arg
                260                 265                 270

Gln Gln Trp Gly Asp Trp Cys Asn Val Leu Gly Ala Gly Phe Gly Thr
            275                 280                 285

Gln Pro Thr Thr Asn Thr Gly Ser Ser Leu Ile Asp Ser Ile Val Trp
            290                 295                 300

Val Lys Pro Gly Gly Glu Cys Asp Gly Thr Ser Asn Thr Ser Ser Pro
305                 310                 315                 320

Arg Tyr Asp Ala His Cys Gly Leu Pro Asp Ala Thr Pro Asn Ala Pro
                325                 330                 335

Glu Ala Gly Thr Trp Phe Gln Ala Tyr Phe Glu Thr Leu Val Glu Lys
                340                 345                 350

Ala Asn Pro Pro Leu
            355

<210> SEQ ID NO 29
<211> LENGTH: 365
<212> TYPE: PRT
<213> ORGANISM: Malbranchea cinnamomea

<400> SEQUENCE: 29

Gln Ala Asn Ser Ser Asn Pro Phe Ala Gly His Thr Ile Tyr Pro Asn
1               5                   10                  15

Pro Tyr Tyr Ser Asn Glu Ile Asp Glu Phe Ala Ile Pro Ala Leu Gln
                20                  25                  30

Glu Thr Asp Pro Ala Leu Val Glu Lys Ala Ala Leu Val Lys Glu Val
            35                  40                  45

Gly Thr Phe Phe Trp Ile Asp Val Val Ala Lys Val Pro Asp Ile Gly
        50                  55                  60

Pro Tyr Leu Gln Gly Ile Gln Glu Ala Asn Ala Ala Gly Gln Asn Pro
65              70                  75                  80

Pro Tyr Ile Gly Ala Ile Val Tyr Asp Leu Pro Asn Arg Asp Cys
                85                  90                  95

Ala Ala Ala Ala Ser Asn Gly Glu Phe Ser Leu Glu Asp Gly Gly Glu
                100                 105                 110

Glu Lys Tyr Arg Gly Tyr Ile Asp Gly Ile Arg Glu Gln Ile Glu Lys
            115                 120                 125

Tyr Pro Asp Val Arg Val Ala Leu Val Ile Glu Pro Asp Ser Leu Ala
        130                 135                 140

Asn Met Val Thr Asn Leu Asn Val Pro Lys Cys Ala Glu Ser Glu Gln
145                 150                 155                 160

Ala Tyr Arg Asp Gly Val Ala Tyr Ala Leu Lys Gln Leu Asp Leu Pro
                165                 170                 175

Asn Val Trp Thr Tyr Ile Asp Ala Gly His Ser Gly Trp Leu Gly Trp
            180                 185                 190

Pro Ala Asn Ile Glu Pro Ala Ala Glu Ile Phe Val Glu Val Trp Asn
        195                 200                 205

Ala Ala Gly Arg Pro Lys Ser Thr Arg Gly Phe Ala Thr Asn Val Ser
    210                 215                 220
```

```
Asn Tyr Asn Gly Tyr Ser Leu Ser Thr Ala Pro Pro Tyr Thr Glu Pro
225                 230                 235                 240

Asn Pro Asn Phe Asp Glu Val Arg Tyr Ile Asn Ala Phe Arg Pro Leu
            245                 250                 255

Leu Glu Ala Arg Gly Phe Pro Ala Tyr Phe Ile Val Asp Gln Gly Arg
        260                 265                 270

Ser Gly Val Gln Pro Thr Ala Gln Ile Glu Gln Gly His Trp Cys Asn
        275                 280                 285

Val Ile Asp Thr Gly Phe Gly Thr Arg Pro Thr Thr Asp Thr Gly Asn
    290                 295                 300

Glu Tyr Val Asp Ser Ile Val Trp Val Lys Pro Gly Gly Glu Ser Asp
305                 310                 315                 320

Gly Thr Ser Asp Thr Ser Ala Glu Arg Tyr Asp Tyr His Cys Gly Leu
                325                 330                 335

Glu Asp Ala Leu Lys Pro Ala Pro Glu Ala Gly Gln Trp Phe Gln Ala
            340                 345                 350

Tyr Phe Glu Gln Leu Leu Arg Asn Ala Asn Pro Phe
        355                 360                 365
```

<210> SEQ ID NO 30
<211> LENGTH: 440
<212> TYPE: PRT
<213> ORGANISM: Phanerochaete chrysosporium

<400> SEQUENCE: 30

```
Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
            20                  25                  30

Ser Gln Cys Leu Pro Gly Ser Ala Val Thr Thr Ser Val Ile Thr
        35                  40                  45

Ser His Ser Ser Ser Val Ser Val Ser Ser His Ser Gly Ser Ser
    50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
            85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240
```

```
Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
        260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
        290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
            355                 360                 365

Phe Gly Thr Arg Pro Thr Thr Asn Thr Gly Ser Gln Phe Ile Asp Ser
        370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
            435                 440

<210> SEQ ID NO 31
<211> LENGTH: 360
<212> TYPE: PRT
<213> ORGANISM: Volvariella volvacea

<400> SEQUENCE: 31

Val Pro Ala Ala Gly Asn Pro Tyr Thr Gly Tyr Glu Ile Tyr Leu Ser
1               5                   10                  15

Pro Tyr Tyr Ala Ala Glu Ala Gln Ala Ala Ala Gln Ile Ser Asp
            20                  25                  30

Ala Thr Gln Lys Ala Lys Ala Leu Lys Val Ala Gln Ile Pro Thr Phe
            35                  40                  45

Thr Trp Phe Asp Val Ile Ala Lys Thr Ser Thr Leu Gly Asp Tyr Leu
    50                  55                  60

Ala Glu Ala Ser Ala Leu Gly Lys Ser Ser Gly Lys Lys Tyr Leu Val
65                  70                  75                  80

Gln Ile Val Val Tyr Asp Leu Pro Asp Arg Asp Cys Ala Ala Leu Ala
                85                  90                  95

Ser Asn Gly Glu Phe Ser Ile Ala Asn Asn Gly Leu Asn Asn Tyr Lys
            100                 105                 110

Gly Tyr Ile Asp Gln Leu Val Ala Gln Ile Lys Lys Tyr Pro Asp Val
        115                 120                 125

Arg Val Val Ala Val Ile Glu Pro Asp Ser Leu Ala Asn Leu Val Thr
        130                 135                 140

Asn Leu Asn Val Ser Lys Cys Ala Asn Ala Gln Thr Ala Tyr Lys Ala
145                 150                 155                 160

Gly Val Thr Tyr Ala Leu Gln Gln Leu Asn Ser Val Gly Val Tyr Met
                165                 170                 175
```

Tyr Leu Asp Ala Gly His Ala Gly Trp Leu Gly Trp Pro Ala Asn Leu
            180                 185                 190

Asn Pro Ala Ala Gln Leu Phe Ser Gln Leu Tyr Arg Asp Ala Gly Ser
            195                 200                 205

Pro Gln Tyr Val Arg Gly Leu Ala Thr Asn Val Ala Asn Tyr Asn Ala
            210                 215                 220

Leu Ser Ala Ser Ser Pro Asp Pro Val Thr Gln Gly Asn Pro Asn Tyr
225                 230                 235                 240

Asp Glu Leu His Tyr Ile Asn Ala Leu Ala Pro Ala Leu Gln Ser Gly
                245                 250                 255

Gly Phe Pro Ala His Phe Ile Val Asp Gln Gly Arg Ser Gly Val Gln
            260                 265                 270

Asn Ile Arg Gln Gln Trp Gly Asp Trp Cys Asn Val Lys Gly Ala Gly
            275                 280                 285

Phe Gly Gln Arg Pro Thr Leu Ser Thr Gly Ser Ser Leu Ile Asp Ala
            290                 295                 300

Ile Val Trp Ile Lys Pro Gly Gly Glu Cys Asp Gly Thr Thr Asn Thr
305                 310                 315                 320

Ser Ser Pro Arg Tyr Asp Ser His Cys Gly Leu Ser Asp Ala Thr Pro
                325                 330                 335

Asn Ala Pro Glu Ala Gly Gln Trp Phe Gln Ala Tyr Phe Glu Thr Leu
            340                 345                 350

Val Arg Asn Ala Ser Pro Pro Leu
            355                 360

<210> SEQ ID NO 32
<211> LENGTH: 356
<212> TYPE: PRT
<213> ORGANISM: Chrysosporium lucknowense

<400> SEQUENCE: 32

Leu Asp Ala Ser Thr Asn Val Phe Gln Gln Tyr Thr Leu His Pro Asn
1               5                   10                  15

Asn Phe Tyr Arg Ala Glu Val Glu Ala Ala Ala Glu Ala Ile Ser Asp
            20                  25                  30

Ser Ala Leu Ala Glu Lys Ala Arg Lys Val Ala Asp Val Gly Thr Phe
        35                  40                  45

Leu Trp Leu Asp Thr Ile Glu Asn Ile Gly Arg Leu Glu Pro Ala Leu
50                  55                  60

Glu Asp Val Pro Cys Glu Asn Ile Val Gly Leu Val Ile Tyr Asp Leu
65                  70                  75                  80

Pro Gly Arg Asp Cys Ala Ala Lys Ala Ser Asn Gly Glu Leu Lys Val
                85                  90                  95

Gly Glu Leu Asp Arg Tyr Lys Thr Glu Tyr Ile Asp Lys Ile Ala Glu
            100                 105                 110

Ile Leu Lys Ala His Ser Asn Thr Ala Phe Ala Leu Val Ile Glu Pro
        115                 120                 125

Asp Ser Leu Pro Asn Leu Val Thr Asn Ser Asp Leu Gln Thr Cys Gln
130                 135                 140

Gln Ser Ala Ser Gly Tyr Arg Glu Gly Val Ala Tyr Ala Leu Lys Gln
145                 150                 155                 160

Leu Asn Leu Pro Asn Val Val Met Tyr Ile Asp Ala Gly His Gly Gly
                165                 170                 175

Trp Leu Gly Trp Asp Ala Asn Leu Lys Pro Gly Ala Gln Glu Leu Ala
            180                 185                 190

```
Ser Val Tyr Lys Ser Ala Gly Ser Pro Ser Gln Val Arg Gly Ile Ser
    195                 200                 205

Thr Asn Val Ala Gly Trp Asn Ala Trp Asp Gln Glu Pro Gly Glu Phe
    210                 215                 220

Ser Asp Ala Ser Asp Ala Gln Tyr Asn Lys Cys Gln Asn Glu Lys Ile
225                 230                 235                 240

Tyr Ile Asn Thr Phe Gly Ala Glu Leu Lys Ser Ala Gly Met Pro Asn
                245                 250                 255

His Ala Ile Ile Asp Thr Gly Arg Asn Gly Val Thr Gly Leu Arg Asp
                260                 265                 270

Glu Trp Gly Asp Trp Cys Asn Val Asn Gly Ala Gly Phe Gly Val Arg
            275                 280                 285

Pro Thr Ala Asn Thr Gly Asp Glu Leu Ala Asp Ala Phe Val Trp Val
        290                 295                 300

Lys Pro Gly Gly Glu Ser Asp Gly Thr Ser Asp Ser Ser Ala Ala Arg
305                 310                 315                 320

Tyr Asp Ser Phe Cys Gly Lys Pro Asp Ala Phe Lys Pro Ser Pro Glu
                325                 330                 335

Ala Gly Thr Trp Asn Gln Ala Tyr Phe Glu Met Leu Leu Lys Asn Ala
                340                 345                 350

Asn Pro Ser Phe
            355

<210> SEQ ID NO 33
<211> LENGTH: 409
<212> TYPE: PRT
<213> ORGANISM: Pleurotus sajor-caju

<400> SEQUENCE: 33

Thr Pro Asp Ala Gly Asn Pro Tyr Ile Gly Tyr Asp Val Ser His Val
1               5                   10                  15

Leu Trp Cys Gln Ile Tyr Leu Ser Pro Tyr Ala Asp Glu Val Ala
            20                  25                  30

Ala Ala Val Ser Ala Ile Ser Asn Pro Ala Leu Ala Ala Lys Ala Ala
        35                  40                  45

Ser Val Ala Asn Ile Pro Thr Phe Ile Trp Phe Asp Val Val Ala Lys
    50                  55                  60

Val Pro Thr Leu Gly Thr Tyr Leu Ala Asp Ala Leu Ser Ile Gln Gln
65                  70                  75                  80

Ser Thr Gly Arg Asn Gln Leu Val Gln Ile Val Val Tyr Asp Leu Pro
                85                  90                  95

Asp Arg Asp Cys Ala Ala Leu Ala Ser Asn Gly Glu Phe Ser Ile Ala
            100                 105                 110

Asn Asn Gly Leu Ala Asn Tyr Lys Asn Tyr Val Asp Gln Ile Val Ala
        115                 120                 125

Gln Ile Ala Arg Thr Cys Cys Pro Leu Val Thr Ser Ala Ile Thr Asp
    130                 135                 140

Leu Ala Cys Leu Ser Glu Tyr Pro Gln Ile Arg Val Val Ala Val Val
145                 150                 155                 160

Glu Pro Asp Ser Leu Ala Asn Met Val Thr Asn Leu Asn Val Pro Lys
                165                 170                 175

Cys Ala Gly Ala Gln Ala Ala Tyr Thr Glu Gly Val Thr Tyr Ala Leu
            180                 185                 190

Gln Lys Leu Asn Thr Val Gly Val Tyr Ser Tyr Val Asp Ala Gly His
        195                 200                 205
```

-continued

Ala Gly Trp Leu Gly Trp Pro Ala Asn Leu Gly Pro Ala Ala Gln Leu
    210                 215                 220

Phe Ala Asn Leu Tyr Thr Asn Ala Gly Ser Pro Ser Phe Phe Arg Gly
225                 230                 235                 240

Leu Ala Thr Asn Val Ala Asn Tyr Asn Leu Leu Asn Ala Pro Ser Pro
                245                 250                 255

Asp Pro Val Thr Ser Pro Asn Ala Asn Tyr Asp Glu Ile His Tyr Ile
            260                 265                 270

Asn Val Ser Asp Cys Phe Val Leu Ile Trp Thr Ser Leu Thr Ile Cys
        275                 280                 285

Ile Ile Ala Leu Ala Pro Glu Leu Ser Ser Arg Gly Phe Pro Ala His
    290                 295                 300

Phe Ile Val Asp Gln Gly Arg Ser Ala Val Gln Gly Ile Arg Gly Ala
305                 310                 315                 320

Trp Gly Asp Trp Cys Asn Val Asp Asn Ala Gly Phe Gly Thr Arg Pro
                325                 330                 335

Thr Thr Ser Thr Gly Ser Ser Leu Ile Asp Ala Ile Val Trp Val Lys
            340                 345                 350

Pro Gly Gly Glu Ser Asp Gly Thr Ser Asp Thr Ser Ala Val Arg Tyr
        355                 360                 365

Asp Gly His Cys Gly Leu Ala Ser Ala Lys Lys Pro Ala Pro Glu Ala
    370                 375                 380

Met Ala Ser Val Tyr Ser His Ser Ser Phe Gln Ala Tyr Phe Glu Met
385                 390                 395                 400

Leu Val Ala Asn Ala Val Pro Ala Leu
                405

<210> SEQ ID NO 34
<211> LENGTH: 359
<212> TYPE: PRT
<213> ORGANISM: Trametes versicolor

<400> SEQUENCE: 34

Thr Pro Ala Ala Gly Asn Pro Phe Thr Gly Phe Gln Val Tyr Leu Ser
1               5                   10                  15

Pro Tyr Tyr Ser Ala Glu Ile Ala Ser Ala Ala Ala Val Thr Asp Asp
            20                  25                  30

Ser Ser Leu Lys Ala Lys Ala Ala Ser Val Ala Asn Ile Pro Thr Phe
        35                  40                  45

Thr Trp Leu Asp Ser Val Ala Lys Val Pro Asp Leu Gly Thr Tyr Leu
    50                  55                  60

Ala Asp Ala Ser Ser Ile Gln Thr Lys Thr Gly Gln Lys Gln Leu Val
65                  70                  75                  80

Pro Ile Val Val Tyr Glu Leu Pro Asp Arg Asp Cys Ala Ala Lys Ala
                85                  90                  95

Ser Asn Gly Glu Phe Ser Ile Ala Asp Ala Gly Ala Glu Asn Tyr Lys
            100                 105                 110

Asp Tyr Ile Asp Gln Ile Val Pro Gln Ile Lys Gln Phe Pro Asp Val
        115                 120                 125

Arg Val Val Ala Val Ile Glu Pro Asp Ser Leu Ala Asn Leu Val Thr
    130                 135                 140

Asn Leu Asn Val Gln Lys Cys Ala Asn Gly Gly Thr Tyr Lys Ala Ser
145                 150                 155                 160

Val Thr Tyr Ala Leu Gln Gln Leu Ser Ser Val Gly Val Thr Met Tyr
                165                 170                 175

```
Met Asp Ala Gly His Ala Gly Trp Leu Gly Trp Pro Ala Asn Ile Gln
            180                 185                 190

Pro Gly Ser Glu Val Phe Ala Glu Met Phe Lys Ser Ala Asp Phe Val
        195                 200                 205

Ala Phe Val Arg Ala Phe Ala Thr Asn Val Arg Glu Tyr Asn Ala Leu
    210                 215                 220

Thr Ala Ala Phe Pro Arg Pro Ile Thr Gln Gly Asn Pro Asn Tyr Asp
225                 230                 235                 240

Glu Phe Pro Tyr Ile Gln Arg Val Arg Pro Met Leu Lys Ser Pro Gly
                245                 250                 255

Phe Pro Ala Gln Phe Val Val Asp Gln Gly Arg Ala Gly Gln Gln Asn
            260                 265                 270

Phe Arg Gln Gln Trp Gly Asp Trp Cys Asn Ile Lys Gly Ala Gly Phe
        275                 280                 285

Gly Thr Arg Pro Thr Thr Ser Thr Gly Asn Pro Leu Ile Asp Ala Ile
    290                 295                 300

Ile Trp Val Lys Pro Gly Glu Ser Asp Gly Thr Ser Asn Ser Ser
305                 310                 315                 320

Ser Pro Arg Tyr Asp Ser Thr Leu Leu Ser Val Arg Arg Asp Asp Pro
                325                 330                 335

Ala Pro Glu Ala Gly Thr Trp Phe Gln Ala Tyr Phe Glu Thr Leu Val
            340                 345                 350

Ser Lys Pro Thr Arg Pro Leu
        355

<210> SEQ ID NO 35
<211> LENGTH: 356
<212> TYPE: PRT
<213> ORGANISM: Neurospora crassa OR74A

<400> SEQUENCE: 35

Leu Asp Ala Ser Thr Asn Val Trp Lys Lys Tyr Thr Leu His Ala Asn
1               5                   10                  15

Lys Phe Tyr Arg Thr Glu Val Glu Ala Ala Val Ala Ala Ile Ser Asp
            20                  25                  30

Ser Ser Leu Ala Ala Lys Ala Ala Lys Val Ala Asn Val Gly Ser Phe
        35                  40                  45

Leu Trp Leu Asp Ser Ile Glu Asn Ile Gly Lys Leu Glu Pro Ala Leu
    50                  55                  60

Glu Asp Val Pro Cys Asp His Ile Leu Gly Leu Val Ile Tyr Asp Leu
65                  70                  75                  80

Pro Gly Arg Asp Cys Ala Ala Lys Ala Ser Asn Gly Glu Leu Ala Val
                85                  90                  95

Gly Glu Leu Ser Arg Tyr Lys Thr Glu Tyr Ile Asp Ala Ile Val Lys
            100                 105                 110

Ile Leu Lys Ala His Pro Lys Thr Ala Phe Ala Leu Val Ile Glu Pro
        115                 120                 125

Asp Ser Leu Pro Asn Leu Val Thr Asn Ser Asp Leu Gln Thr Cys Lys
    130                 135                 140

Asp Ser Ala Ser Gly Tyr Arg Asp Gly Val Ala Tyr Ala Leu Arg Asn
145                 150                 155                 160

Leu Asn Leu Pro Asn Val Val Met Tyr Ile Asp Ala Gly His Gly Gly
                165                 170                 175

Trp Leu Gly Trp Asp Ala Asn Leu Lys Pro Gly Ala Gln Glu Leu Ala
            180                 185                 190
```

```
Lys Ala Tyr Lys Ala Ala Gly Ser Pro Lys Gln Val Arg Gly Ile Ala
            195                 200                 205

Thr Asn Val Ala Gly Trp Asn Gln Trp Asp Leu Thr Pro Gly Glu Phe
            210                 215                 220

Ser Lys Ala Ser Asp Ala Lys Tyr Asn Lys Cys Gln Asn Glu Lys Leu
225                 230                 235                 240

Tyr Leu Asp Asn Phe Gly Pro Ala Leu Lys Ser Ala Gly Met Pro Asn
            245                 250                 255

His Ala Ile Val Asp Thr Gly Arg Asn Gly Val Ser Gly Leu Arg Gln
            260                 265                 270

Glu Trp Gly Asn Trp Cys Asn Val Asn Gly Ala Gly Phe Gly Val Arg
            275                 280                 285

Pro Thr Ser Ser Thr Gly His Asp Leu Ala Asp Ala Phe Val Trp Val
            290                 295                 300

Lys Pro Gly Gly Glu Ser Asp Gly Thr Ser Asp Ser Ser Ala Thr Arg
305                 310                 315                 320

Tyr Asp Ser Phe Cys Gly Lys Ser Asp Ala Tyr Gln Pro Ser Pro Glu
            325                 330                 335

Ala Gly Ser Trp Asn Gln Asp Tyr Phe Glu Met Leu Val Lys Asn Ala
            340                 345                 350

Lys Pro Ser Phe
            355

<210> SEQ ID NO 36
<211> LENGTH: 356
<212> TYPE: PRT
<213> ORGANISM: Magnaporthe grisea 70-15

<400> SEQUENCE: 36

Leu Asp Ala Ser Thr Asn Val Phe Ser Lys Tyr Thr Leu His Pro Asn
1               5                   10                  15

Ser Phe Tyr Arg Ala Glu Val Glu Ala Ala Glu Ala Ile Ser Asp
            20                  25                  30

Ser Thr Leu Lys Ala Gln Ala Leu Lys Val Ala Asp Val Gly Ser Phe
            35                  40                  45

Leu Trp Ile Asp Thr Ile Ser Ala Ile Ser Arg Ile Glu Pro Gly Val
    50                  55                  60

Ser Asp Gln Pro Cys Asp His Ile Leu Gly Leu Val Ile Tyr Asp Leu
65                  70                  75                  80

Pro Gly Arg Asp Cys Ala Ala Lys Ala Ser Asn Gly Glu Leu Lys Val
            85                  90                  95

Gly Glu Leu Ala Lys Tyr Lys Ser Gln Tyr Ile Asp Pro Ile Ala Ala
            100                 105                 110

Leu Leu Lys Lys Tyr Asn Asn His Ala Phe Ala Leu Leu Ile Glu Pro
        115                 120                 125

Asp Ser Leu Pro Asn Leu Val Thr Asn Ser Asp Leu Ser Ala Cys Gln
            130                 135                 140

Gln Ser Ala Ala Gly Tyr Arg Asp Gly Val Ala Tyr Ala Leu Lys Thr
145                 150                 155                 160

Leu Asn Leu Pro Asn Val Val Met Tyr Ile Asp Ala Gly His Gly Gly
            165                 170                 175

Trp Leu Gly Trp Asn Asp Asn Leu Lys Pro Gly Ala Glu Glu Leu Ala
            180                 185                 190

Lys Ala Tyr Lys Ala Ala Gly Ser Pro Lys Gln Phe Arg Gly Phe Ala
            195                 200                 205
```

```
Thr Asn Val Ala Gly Trp Asn Ala Trp Asp Leu Thr Pro Gly Glu Phe
    210                 215                 220

Ser Ser Ala Ser Asp Ala Gln Trp Asn Lys Cys Gln Asn Glu Lys Ile
225                 230                 235                 240

Tyr Val Glu Thr Phe Gly Pro Leu Leu Lys Asn Ala Gly Met Pro Asn
                245                 250                 255

His Ala Ile Val Asp Val Gly Arg Asn Ala Val Gln Gly Leu Arg Glu
                260                 265                 270

Glu Trp Gly His Trp Cys Asn Val Asn Gly Ala Gly Phe Gly Val Arg
            275                 280                 285

Pro Thr Thr Ser Thr Gly Ser Ser Leu Thr Asp Ala Leu Leu Trp Val
    290                 295                 300

Lys Pro Gly Gly Glu Ser Asp Gly Thr Ser Asp Thr Ser Ala Thr Arg
305                 310                 315                 320

Tyr Asp Ser Phe Cys Gly Met Ser Asp Ala Tyr Lys Pro Ser Pro Glu
                325                 330                 335

Ala Gly Gln Trp Asn Gln Asp Tyr Phe Glu Met Leu Leu Arg Asn Ala
            340                 345                 350

Lys Pro Gln Phe
        355

<210> SEQ ID NO 37
<211> LENGTH: 447
<212> TYPE: PRT
<213> ORGANISM: Trichoderma reesei

<400> SEQUENCE: 37

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
                115                 120                 125

Glu Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
    195                 200                 205

Tyr Ser Asp Ile Arg Thr Leu Leu Val Ile Glu Pro Asp Ser Leu Ala
    210                 215                 220
```

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
    275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
        340                 345                 350

Arg Ser Gly Lys Gln Pro Thr Gly Gln Gln Gln Trp Gly Asp Trp Cys
    355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
        420                 425                 430

Ala Tyr Phe Val Gln Leu Leu Thr Asn Ala Asn Pro Ser Phe Leu
    435                 440                 445

<210> SEQ ID NO 38
<211> LENGTH: 447
<212> TYPE: PRT
<213> ORGANISM: Trichoderma reesei

<400> SEQUENCE: 38

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
        100                 105                 110

Ile Pro Ser Leu Thr Gly Ala Met Ala Thr Ala Ala Ala Ala Val Ala
    115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

-continued

Asn Tyr Ala Gly Gln Phe Val Val Tyr Asp Leu Pro Asp Arg Asp Cys
            165                 170                 175

Ala Ala Leu Ala Ser Asn Gly Glu Tyr Thr Ile Ala Asp Gly Gly Val
        180                 185                 190

Ala Lys Tyr Lys Asn Tyr Ile Asp Thr Ile Arg Gln Ile Val Val Glu
    195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
    275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
        340                 345                 350

Arg Ser Gly Lys Gln Pro Thr Gly Gln Gln Trp Gly Asp Trp Cys
    355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
        420                 425                 430

Ala Tyr Phe Val Gln Leu Leu Thr Asn Ala Asn Pro Ser Phe Leu
    435                 440                 445

<210> SEQ ID NO 39
<211> LENGTH: 447
<212> TYPE: PRT
<213> ORGANISM: Trichoderma reesei

<400> SEQUENCE: 39

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
            85                  90                  95

```
Thr Pro Trp Ala Asn Ala Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130             135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Asp Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 40
<211> LENGTH: 447
<212> TYPE: PRT
<213> ORGANISM: Trichoderma reesei

<400> SEQUENCE: 40

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30
```

-continued

Tyr Tyr Ser Gln Cys Leu Pro Gly Ala Ala Ser Ser Ser Ser Thr
        35              40                  45

Arg Ala Ala Ser Thr Thr Ser Arg Val Ser Pro Thr Thr Ser Arg Ser
 50                      55                  60

Ser Ser Ala Thr Pro Pro Pro Gly Ser Thr Thr Thr Arg Val Pro Pro
 65              70                  75                      80

Val Gly Ser Gly Thr Ala Thr Tyr Ser Gly Asn Pro Phe Val Gly Val
                 85                  90                  95

Thr Pro Trp Ala Asn Ala Tyr Tyr Ala Ser Glu Val Ser Ser Leu Ala
             100                 105                 110

Ile Pro Ser Leu Thr Gly Ala Met Ala Thr Ala Ala Ala Val Ala
             115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                 165                 170                 175

Ala Ala Leu Ala Ser Asn Gly Glu Tyr Ser Ile Ala Asp Gly Gly Val
             180                 185                 190

Ala Lys Tyr Lys Asn Tyr Ile Asp Thr Ile Arg Gln Ile Val Val Glu
             195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                 245                 250                 255

Asn Val Ala Met Tyr Leu Asp Ala Gly His Ala Gly Trp Leu Gly Trp
             260                 265                 270

Pro Ala Asn Gln Asp Pro Ala Ala Gln Leu Phe Ala Asn Val Tyr Lys
             275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                 325                 330                 335

Leu Ala Asn His Gly Trp Ser Asn Ala Phe Phe Ile Thr Asp Gln Gly
             340                 345                 350

Arg Ser Gly Lys Gln Pro Thr Gly Gln Gln Glu Trp Gly Asp Trp Cys
             355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                 405                 410                 415

Leu Pro Asp Ala Leu Gln Pro Ala Pro Gln Ala Gly Ala Trp Phe Gln
             420                 425                 430

Ala Tyr Phe Val Gln Leu Leu Thr Asn Ala Asn Pro Ser Phe Leu
             435                 440                 445

<210> SEQ ID NO 41

```
<211> LENGTH: 447
<212> TYPE: PRT
<213> ORGANISM: Trichoderma reesei

<400> SEQUENCE: 41
```

| | | | | | | | | | | | | | | |
|---|---|---|---|---|---|---|---|---|---|---|---|---|---|---|
| Gln | Ala | Cys | Ser | Ser | Val | Trp | Gly | Gln | Cys | Gly | Gly | Gln | Asn | Trp Ser |
| 1 | | | | 5 | | | | | 10 | | | | | 15 |
| Gly | Pro | Thr | Cys | Cys | Ala | Ser | Gly | Ser | Thr | Cys | Val | Tyr | Ser | Asn Asp |
| | | | 20 | | | | | 25 | | | | | 30 | |
| Tyr | Tyr | Ser | Gln | Cys | Leu | Pro | Gly | Ala | Ala | Ser | Ser | Ser | Ser | Thr |
| | | 35 | | | | | 40 | | | | | 45 | | |
| Arg | Ala | Ala | Ser | Thr | Thr | Ser | Arg | Val | Ser | Pro | Thr | Thr | Ser | Arg Ser |
| | 50 | | | | | 55 | | | | | 60 | | | |
| Ser | Ser | Ala | Thr | Pro | Pro | Pro | Gly | Ser | Thr | Thr | Thr | Arg | Val | Pro Pro |
| 65 | | | | | 70 | | | | | 75 | | | | 80 |
| Val | Gly | Ser | Gly | Thr | Ala | Thr | Tyr | Ser | Gly | Asn | Pro | Phe | Val | Gly Val |
| | | | | 85 | | | | | 90 | | | | | 95 |
| Thr | Pro | Trp | Ala | Asn | Ala | Tyr | Tyr | Ala | Ser | Glu | Val | Ser | Ser | Leu Ala |
| | | | 100 | | | | | 105 | | | | | 110 | |
| Ile | Pro | Ser | Leu | Thr | Gly | Ala | Met | Ala | Thr | Ala | Ala | Ala | Val | Ala |
| | | 115 | | | | | 120 | | | | | 125 | | |
| Lys | Val | Pro | Ser | Phe | Met | Trp | Leu | Asp | Thr | Leu | Asp | Lys | Thr | Pro Leu |
| | 130 | | | | | 135 | | | | | 140 | | | |
| Met | Glu | Gln | Thr | Leu | Ala | Asp | Ile | Arg | Thr | Ala | Asn | Lys | Asn | Gly Gly |
| 145 | | | | | 150 | | | | | 155 | | | | 160 |
| Asn | Tyr | Ala | Gly | Gln | Phe | Val | Val | Tyr | Asp | Leu | Pro | Asp | Arg | Asp Cys |
| | | | | 165 | | | | | 170 | | | | | 175 |
| Ala | Ala | Leu | Ala | Ser | Asn | Gly | Glu | Tyr | Ser | Ile | Ala | Asp | Gly | Gly Val |
| | | | 180 | | | | | 185 | | | | | 190 | |
| Ala | Lys | Tyr | Lys | Asn | Tyr | Ile | Asp | Thr | Ile | Arg | Gln | Ile | Val | Val Glu |
| | | 195 | | | | | 200 | | | | | 205 | | |
| Tyr | Ser | Asp | Ile | Arg | Thr | Leu | Leu | Val | Ile | Glu | Pro | Asp | Ser | Leu Ala |
| | 210 | | | | | 215 | | | | | 220 | | | |
| Asn | Leu | Val | Thr | Asn | Leu | Gly | Thr | Pro | Lys | Cys | Ala | Asn | Ala | Gln Ser |
| 225 | | | | | 230 | | | | | 235 | | | | 240 |
| Ala | Tyr | Leu | Glu | Cys | Ile | Asn | Tyr | Ala | Val | Thr | Gln | Leu | Asn | Leu Pro |
| | | | | 245 | | | | | 250 | | | | | 255 |
| Asn | Val | Ala | Met | Tyr | Leu | Asp | Ala | Gly | His | Ala | Gly | Trp | Leu | Gly Trp |
| | | | 260 | | | | | 265 | | | | | 270 | |
| Pro | Ala | Asn | Gln | Asp | Pro | Ala | Ala | Gln | Leu | Phe | Ala | Asn | Val | Tyr Lys |
| | | 275 | | | | | 280 | | | | | 285 | | |
| Asn | Ala | Ser | Ser | Pro | Arg | Ala | Leu | Arg | Gly | Leu | Ala | Thr | Asn | Val Ala |
| | 290 | | | | | 295 | | | | | 300 | | | |
| Asn | Tyr | Asn | Gly | Trp | Asn | Ile | Thr | Ser | Pro | Pro | Ser | Tyr | Thr | Gln Gly |
| 305 | | | | | 310 | | | | | 315 | | | | 320 |
| Asn | Ala | Val | Tyr | Asn | Glu | Lys | Leu | Tyr | Ile | His | Ala | Ile | Gly | Pro Leu |
| | | | | 325 | | | | | 330 | | | | | 335 |
| Leu | Ala | Asn | His | Gly | Trp | Ser | Asn | Ala | Phe | Phe | Ile | Thr | Asp | Gln Gly |
| | | | 340 | | | | | 345 | | | | | 350 | |
| Arg | Ser | Gly | Lys | Gln | Pro | Thr | Gly | Gln | Gln | Gln | Trp | Gly | Asp | Trp Cys |
| | | 355 | | | | | 360 | | | | | 365 | | |
| Asn | Val | Ile | Gly | Thr | Gly | Phe | Gly | Ile | Arg | Pro | Ser | Ala | Asn | Thr Gly |
| | 370 | | | | | 375 | | | | | 380 | | | |
| Asp | Ser | Leu | Leu | Asp | Ser | Phe | Val | Trp | Val | Lys | Pro | Gly | Gly | Glu Cys |
| 385 | | | | | 390 | | | | | 395 | | | | 400 |

```
Asp Gly Thr Ser Asp Ser Ser Ala Pro Gly Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 42
<211> LENGTH: 447
<212> TYPE: PRT
<213> ORGANISM: Trichoderma reesei

<400> SEQUENCE: 42

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
                35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65              70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
                115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
                180                 185                 190

Ala Lys Tyr Lys Asn Tyr Ile Asp Thr Ile Arg Gln Ile Val Val Glu
    195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
    275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335
```

-continued

```
Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 43
<211> LENGTH: 447
<212> TYPE: PRT
<213> ORGANISM: Trichoderma reesei

<400> SEQUENCE: 43

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Glu Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Thr Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270
```

```
Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
            290                 295                 300

Asn Tyr Asn Gly Trp Asn Ile Thr Ser Pro Ser Tyr Thr Gln Gly
305                 310                 315                 320

Asn Asp Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Glu Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 44
<211> LENGTH: 447
<212> TYPE: PRT
<213> ORGANISM: Trichoderma reesei

<400> SEQUENCE: 44

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Glu Val Pro Ser Phe Met Trp Leu Asp Thr Leu Asp Lys Thr Pro Leu
            130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
            165                 170                 175

Ala Ala Leu Ala Ser Asn Gly Glu Tyr Thr Ile Ala Asp Gly Gly Val
            180                 185                 190

Ala Lys Tyr Lys Asn Tyr Ile Asp Thr Ile Arg Gln Ile Val Val Glu
            195                 200                 205
```

```
Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Asp Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Glu Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 45
<211> LENGTH: 21
<212> TYPE: DNA
<213> ORGANISM: Artificial
<220> FEATURE:
<223> OTHER INFORMATION: Primer sequence

<400> SEQUENCE: 45
agcacaaata acgggttatt g                                          21

<210> SEQ ID NO 46
<211> LENGTH: 30
<212> TYPE: DNA
<213> ORGANISM: Artificial
<220> FEATURE:
<223> OTHER INFORMATION: Primer sequence

<400> SEQUENCE: 46
accaaaagat ctatgagatt tccttcaatt                                 30

<210> SEQ ID NO 47
<211> LENGTH: 30
<212> TYPE: DNA
<213> ORGANISM: Artificial
<220> FEATURE:
<223> OTHER INFORMATION: Primer sequence

<400> SEQUENCE: 47
```

```
tgagcagcta gccctttat ccaaagatac                                    30

<210> SEQ ID NO 48
<211> LENGTH: 30
<212> TYPE: DNA
<213> ORGANISM: Artificial
<220> FEATURE:
<223> OTHER INFORMATION: Primer sequence

<400> SEQUENCE: 48
aaaagggcta gctgctcaag cgtctggggc                                   30

<210> SEQ ID NO 49
<211> LENGTH: 36
<212> TYPE: DNA
<213> ORGANISM: Artificial
<220> FEATURE:
<223> OTHER INFORMATION: Primer sequence

<400> SEQUENCE: 49
gagctcagat ctggtacctt acaggaacga tgggtt                            36

<210> SEQ ID NO 50
<211> LENGTH: 47
<212> TYPE: DNA
<213> ORGANISM: Artificial
<220> FEATURE:
<223> OTHER INFORMATION: Primer sequence

<400> SEQUENCE: 50
ggccactgct gcagcagctg tcgcagaagt ccctcttttt atgtggc                47

<210> SEQ ID NO 51
<211> LENGTH: 47
<212> TYPE: DNA
<213> ORGANISM: Artificial
<220> FEATURE:
<223> OTHER INFORMATION: Primer sequence

<400> SEQUENCE: 51
gccacataaa agagggaact tctgcgacag ctgctgcagc agtggcc                47

<210> SEQ ID NO 52
<211> LENGTH: 48
<212> TYPE: DNA
<213> ORGANISM: Artificial
<220> FEATURE:
<223> OTHER INFORMATION: Primer sequence

<400> SEQUENCE: 52
gcccttgcct cgaatggcga atacactatt gccgatggtg gcgtcgcc               48

<210> SEQ ID NO 53
<211> LENGTH: 48
<212> TYPE: DNA
<213> ORGANISM: Artificial
<220> FEATURE:
<223> OTHER INFORMATION: Primer sequence

<400> SEQUENCE: 53
ggcgacgcca ccatcggcaa tagtgtattc gccattcgag gcaagggc               48

<210> SEQ ID NO 54
<211> LENGTH: 33
<212> TYPE: DNA
<213> ORGANISM: Artificial
<220> FEATURE:
```

```
<223> OTHER INFORMATION: Primer sequence

<400> SEQUENCE: 54
tacacgcaag gcaacgatgt ctacaacgag aag                                      33

<210> SEQ ID NO 55
<211> LENGTH: 33
<212> TYPE: DNA
<213> ORGANISM: Artificial
<220> FEATURE:
<223> OTHER INFORMATION: Primer sequence

<400> SEQUENCE: 55
cttctcgttg tagacatcgt tgccttgcgt gta                                      33

<210> SEQ ID NO 56
<211> LENGTH: 23
<212> TYPE: DNA
<213> ORGANISM: Artificial
<220> FEATURE:
<223> OTHER INFORMATION: Primer sequence

<400> SEQUENCE: 56
gcaacacctg gcaattcctt acc                                                 23

<210> SEQ ID NO 57
<211> LENGTH: 33
<212> TYPE: DNA
<213> ORGANISM: Artificial
<220> FEATURE:
<223> OTHER INFORMATION: Primer sequence

<400> SEQUENCE: 57
gacagcagtg cgccacagtt tgaccccac tgt                                       33

<210> SEQ ID NO 58
<211> LENGTH: 33
<212> TYPE: DNA
<213> ORGANISM: Artificial
<220> FEATURE:
<223> OTHER INFORMATION: Primer sequence

<400> SEQUENCE: 58
acagtggggg tcaaactgtg gcgcactgct gtc                                      33
```